US011160936B2

(12) United States Patent
Bache et al.

(10) Patent No.: US 11,160,936 B2
(45) Date of Patent: Nov. 2, 2021

(54) NON-COMBUSTIBLE VAPING DEVICE

(71) Applicant: Altria Client Services LLC, Richmond, VA (US)

(72) Inventors: Terry Bache, Richmond, VA (US); Ryan Newcomb, Richmond, VA (US); Eric A. Hawes, Midlothian, VA (US); Dmitriy Kirzhner, Richmond, VA (US); Raymond Lau, Richmond, VA (US); Danielle Crawford, Richmond, VA (US); Dwight D. Williams, Richmond, VA (US); William Eugene Rabbitt, Chesterland, OH (US); Carl Roy Stevens, Stow, OH (US)

(73) Assignee: Altria Client Services LLC, Richmond, VA (US)

( * ) Notice: Subject to any disclaimer, the term of this patent is extended or adjusted under 35 U.S.C. 154(b) by 983 days.

(21) Appl. No.: 15/631,126

(22) Filed: Jun. 23, 2017

(65) Prior Publication Data
US 2018/0368474 A1    Dec. 27, 2018

(51) Int. Cl.
*A61M 11/04*    (2006.01)
*H05B 1/02*    (2006.01)
(Continued)

(52) U.S. Cl.
CPC .......... *A61M 11/042* (2014.02); *A24F 40/30* (2020.01); *A24F 40/42* (2020.01); *A24F 40/53* (2020.01);
(Continued)

(58) Field of Classification Search
CPC ... A24F 47/008; A61M 11/042; G01N 27/041
(Continued)

(56) References Cited

U.S. PATENT DOCUMENTS 7,185,659 B2 *   3/2007   Sharpe ................. A24F 47/008
                                                          131/194
7,726,320 B2    6/2010   Robinson et al.
(Continued)

FOREIGN PATENT DOCUMENTS

WO    WO-2014/058678 A1    4/2014
WO    WO-2016/005533 A1    1/2016
(Continued)

OTHER PUBLICATIONS

International Search Report and Written Opinion thereof dated Sep. 21, 2018 for correspondinq International Application No. PCT/EP2018/066981.
(Continued)

*Primary Examiner* — Tu B Hoang
*Assistant Examiner* — Thomas J Ward
(74) *Attorney, Agent, or Firm* — Harness, Dickey & Pierce, P.L.C.

(57) ABSTRACT

A vapor cartridge for a non-combustible vaping device may be configured to receive a flavor cartridge, generate a vapor, and direct the generated vapor through the flavor cartridge to provide a flavored vapor. The flavor cartridge may include an instance of electrically conductive material extending at least partially around the flavor cartridge. The vapor cartridge may include an authentication assembly including a set of electrically conductive instruments may independently and directly contact the instance of electrically conductive material of the flavor cartridge inserted into the vapor cartridge, such that the electrically conductive instruments are electrically connected to each other through the instance of electrically conductive material of the flavor cartridge. The vapor cartridge may be coupled with a base that includes a control circuitry configured to control vapor generation by the vapor generator, based on the electrically
(Continued)

conductive instruments being electrically connected to each other through the flavor cartridge.

21 Claims, 14 Drawing Sheets

(51) Int. Cl.
| | |
|---|---|
| *G01N 27/04* | (2006.01) |
| *H01R 13/24* | (2006.01) |
| *A24F 40/30* | (2020.01) |
| *A24F 40/42* | (2020.01) |
| *A24F 40/53* | (2020.01) |
| *A61M 16/00* | (2006.01) |
| *A24F 15/015* | (2020.01) |
| *A24F 40/10* | (2020.01) |
| *A24F 40/20* | (2020.01) |
| *A24F 40/485* | (2020.01) |
| *A24F 40/60* | (2020.01) |

(52) U.S. Cl.
CPC ....... *G01N 27/041* (2013.01); *H01R 13/2421* (2013.01); *H05B 1/0244* (2013.01); *A24F 15/015* (2020.01); *A24F 40/10* (2020.01); *A24F 40/20* (2020.01); *A24F 40/485* (2020.01); *A24F 40/60* (2020.01); *A61M 2016/0024* (2013.01); *A61M 2205/8206* (2013.01)

(58) Field of Classification Search
USPC ......... 392/387, 395, 403; 131/200, 359, 360
See application file for complete search history.

(56) References Cited

U.S. PATENT DOCUMENTS

| | | | |
|---|---|---|---|
| 8,733,346 B2 | 5/2014 | Rinker | |
| 8,881,737 B2 | 11/2014 | Collett et al. | |
| 9,220,302 B2 | 12/2015 | DePiano et al. | |
| 9,247,773 B2 | 2/2016 | Memari et al. | |
| 9,462,830 B2* | 10/2016 | Liu | ........ A24F 47/008 |
| 2014/0196736 A1 | 7/2014 | Fernando et al. | |
| 2014/0202472 A1 | 7/2014 | Levitz et al. | |
| 2015/0020823 A1 | 1/2015 | Lipowicz et al. | |
| 2015/0101625 A1 | 4/2015 | Newton et al. | |
| 2015/0313275 A1 | 11/2015 | Anderson et al. | |
| 2015/0374035 A1 | 12/2015 | Sanchez et al. | |
| 2016/0150828 A1* | 6/2016 | Goldstein | ........ A24F 47/008 |
| | | | 392/387 |
| 2016/0206004 A1 | 7/2016 | Shinkawa et al. | |
| 2016/0206005 A1 | 7/2016 | Yamada et al. | |
| 2016/0262459 A1 | 9/2016 | Monsees et al. | |
| 2016/0302488 A1 | 10/2016 | Fernando et al. | |
| 2016/0309788 A1 | 10/2016 | Hawes et al. | |
| 2016/0324216 A1 | 11/2016 | Li et al. | |
| 2016/0360785 A1 | 12/2016 | Bless et al. | |

FOREIGN PATENT DOCUMENTS

| | | | |
|---|---|---|---|
| WO | WO-2016/005601 A1 | 1/2016 | |
| WO | WO-2016/005602 A1 | 1/2016 | |
| WO | WO-2016/023809 A1 | 2/2016 | |
| WO | WO-2016/171997 A2 | 10/2016 | |
| WO | WO-2016/172023 A1 | 10/2016 | |
| WO | WO-2016/199066 A1 | 12/2016 | |

OTHER PUBLICATIONS

Written Opinion of the International Preliminary Examining Authority dated May 31, 2019 for corresponding International Application No. PCT/EP2018/066981.

* cited by examiner

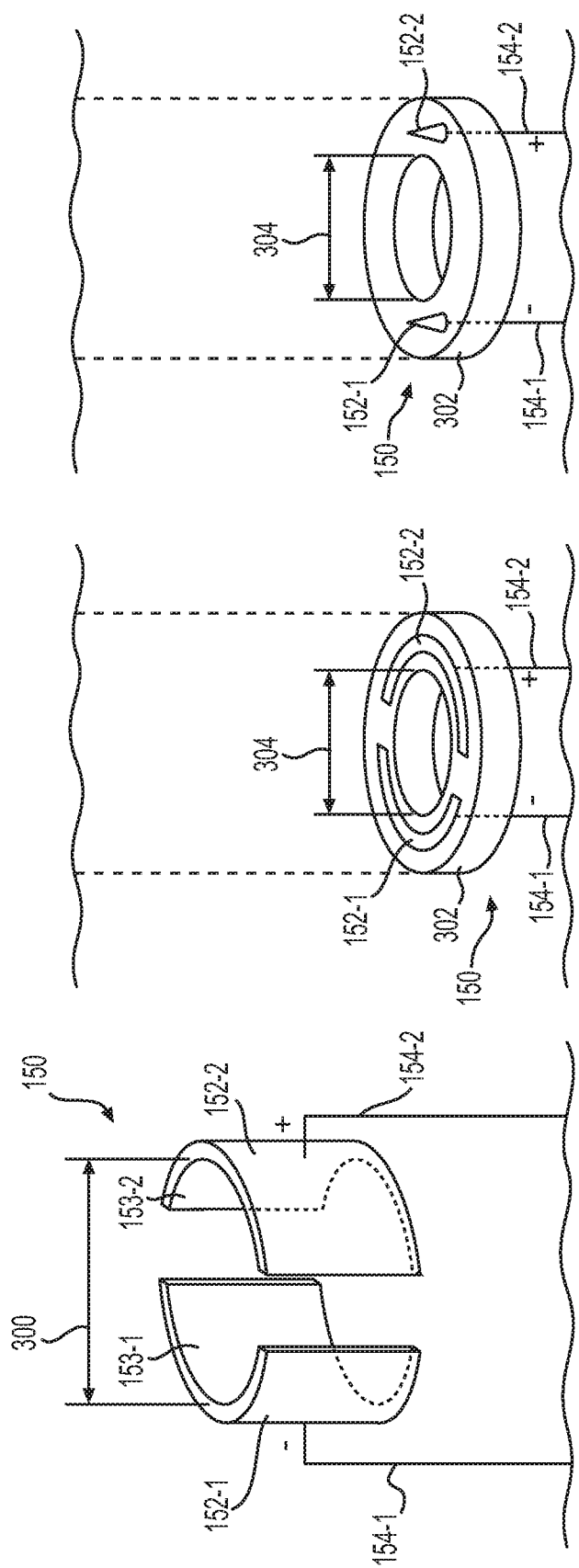

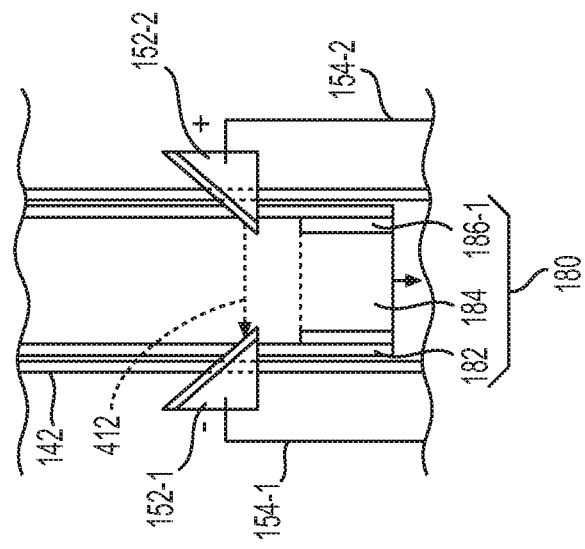
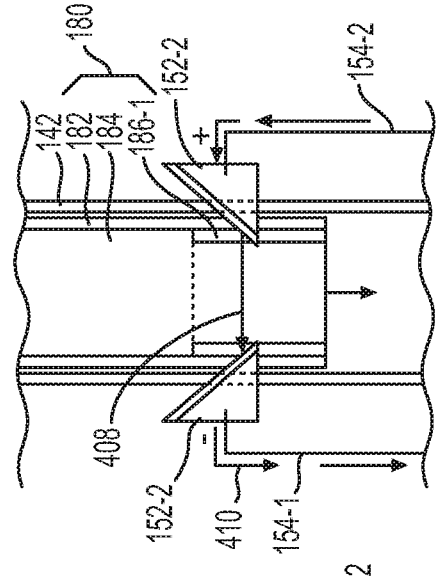
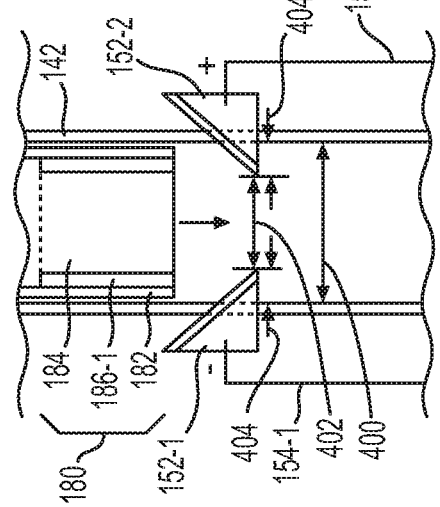

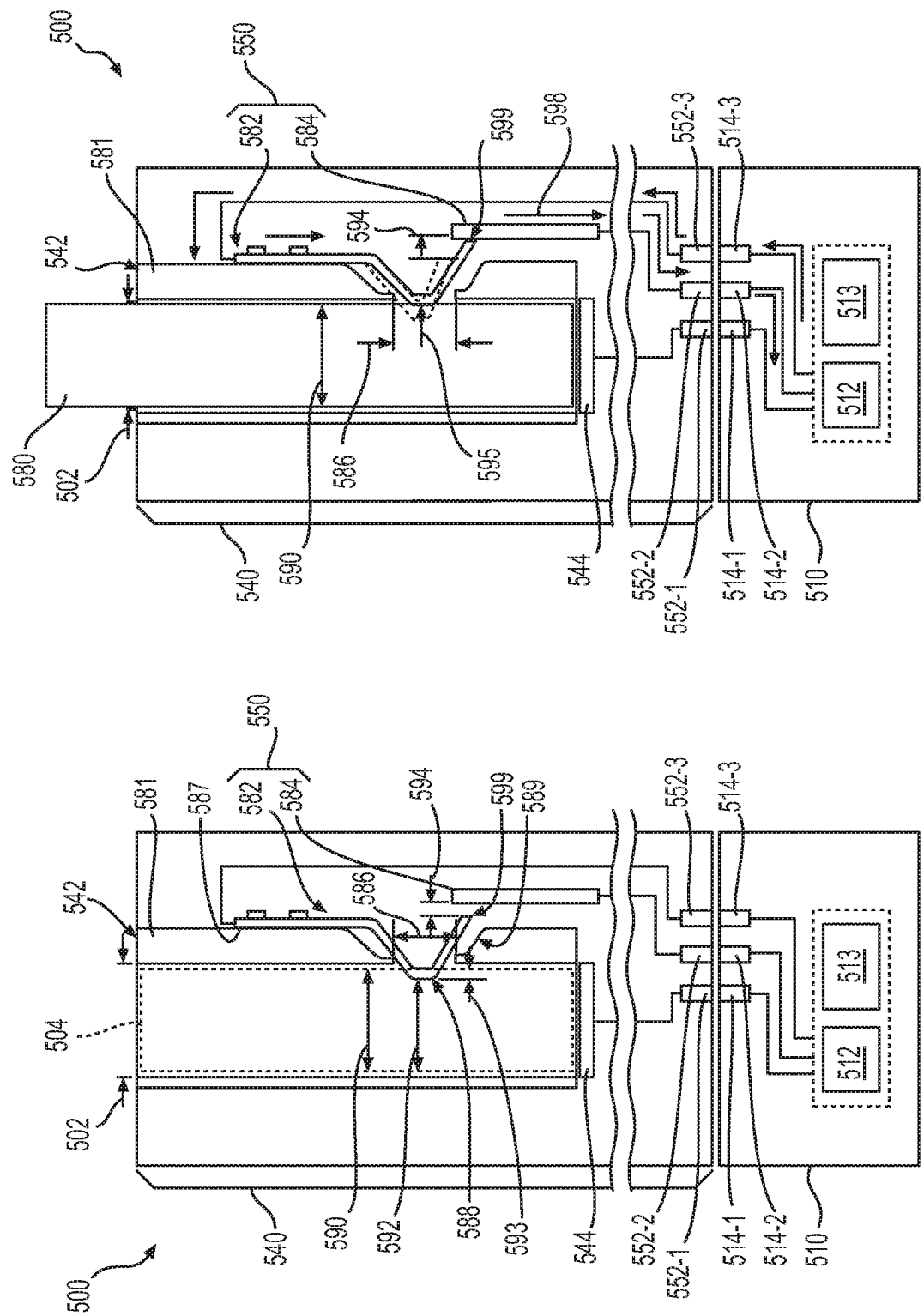

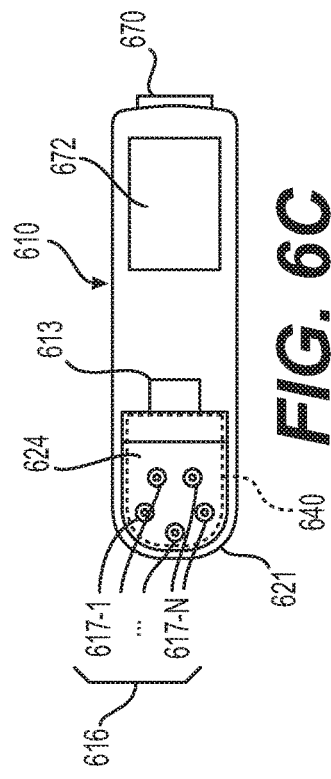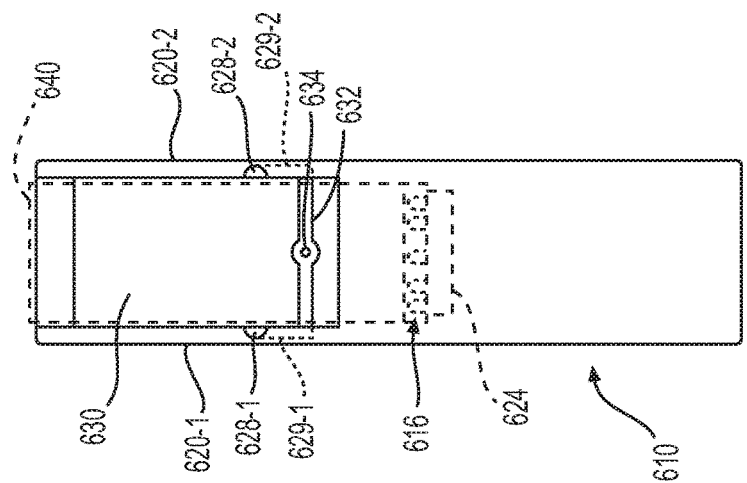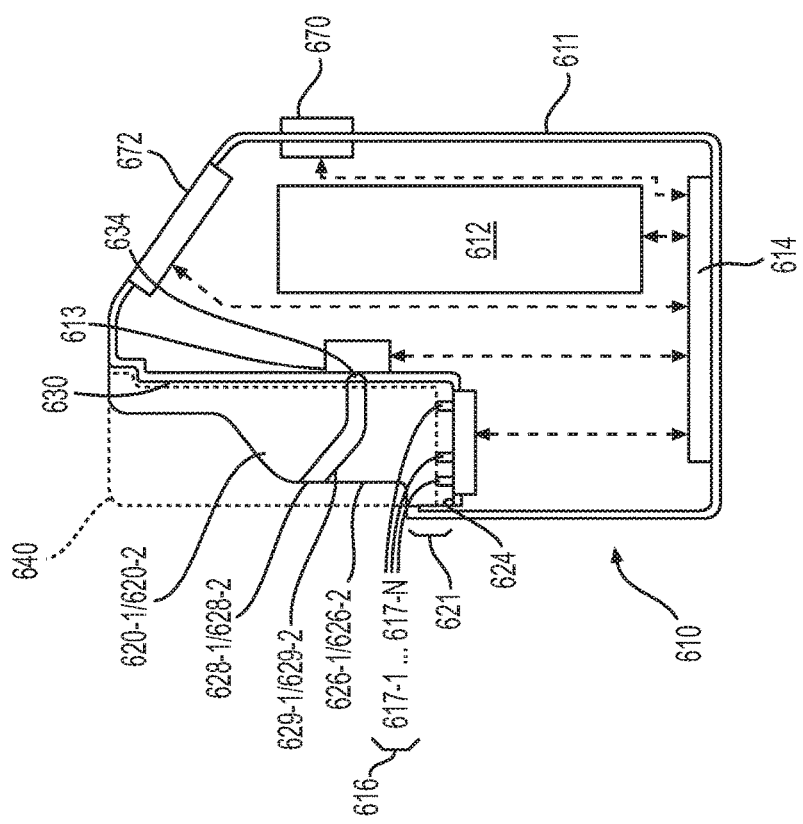

NON-COMBUSTIBLE VAPING DEVICE

BACKGROUND

Field

Example embodiments relate to electronic vaping devices ("e-vaping devices") and/or non-combustible vaping devices.

Description of Related Art

E-vaping devices, also referred to herein as electronic vaping devices (EVDs) may be used by adult vapers for portable vaping. Flavored vapors within an e-vaping device may be used to deliver a flavor along with the vapor that may be produced by the e-vaping device. The flavored vapors may be delivered via a flavor system.

E-vaping devices include a heater which vaporizes pre-vapor formulation to produce a vapor. An e-vaping device may include several e-vaping elements including a power source, a cartridge or e-vaping tank including the heater and along with a reservoir capable of holding the pre-vapor formulation.

SUMMARY

According to some example embodiments, a vapor cartridge for a non-combustible vaping device may include a channel structure, a vapor generator, and a set of electrically conductive instruments. The channel structure may have opposite, first and second ends. The channel structure may at least partially define a channel space extending at least between the first and second ends. The channel structure may be configured to receive a flavor cartridge into the channel space via the first end of the channel structure. The vapor generator may be at the second end of the channel structure. The vapor generator may be configured to heat a pre-vapor formulation to form a generated vapor and provide the generated vapor to the second end of the channel structure. The channel structure may be further configured to receive the flavor cartridge, such that the flavor cartridge is positioned in the channel structure to receive the generated vapor from the vapor generator. The set of electrically conductive instruments may extend into the channel space. The electrically conductive instruments may be configured to independently and directly contact an instance of electrically conductive material of the flavor cartridge, such that the electrically conductive instruments are electrically connected to each other through the instance of electrically conductive material of the flavor cartridge.

At least one electrically conductive instrument of the set of electrically conductive instruments may be configured to directly contact the instance of electrically conductive material based on at least partially impinging into an interior of the flavor cartridge.

The at least one electrically conductive instrument may include an electrically conductive blade. The electrically conductive blade may be configured to cut into at least a portion of the flavor cartridge to directly contact the instance of electrically conductive material of the flavor cartridge.

The set of electrically conductive instruments may include a set of electrically conductive blades that are configured to cut into separate portions of the flavor cartridge to directly contact the instance of electrically conductive material of the flavor cartridge, such that the electrically conductive blades are electrically connected to each other through the instance of electrically conductive material of the flavor cartridge.

At least one electrically conductive instrument of the set of electrically conductive instruments may be an electrically conductive plate configured to establish contact with the instance of electrically conductive material.

At least one electrically conductive instrument of the set of electrically conductive instruments may be a projection instrument configured to puncture at least a portion of the flavor cartridge to directly contact the instance of electrically conductive material of the flavor cartridge.

The vapor cartridge may further include a reservoir refill port in fluid communication with a pre-vapor formulation reservoir of the vapor generator. The reservoir refill port may be configured to enable the pre-vapor formulation reservoir to be filled with the pre-vapor formulation.

According to some example embodiments, a non-combustible vaping device may include a vapor cartridge and a base. The vapor cartridge may include a channel structure, a vapor generator, and a set of electrically conductive instruments. The channel structure may have opposite, first and second ends. The channel structure may at least partially define a channel space extending at least between the first and second ends. The channel structure may be configured to receive a flavor cartridge via the first end of the channel structure. The vapor generator may be at the second end of the channel structure. The vapor generator may be configured to heat a pre-vapor formulation to form a generated vapor and provide the generated vapor to the second end of the channel structure. The channel structure may be further configured to receive the flavor cartridge, such that the flavor cartridge is positioned in the channel structure to receive the generated vapor from the vapor generator. The set of electrically conductive instruments may extend into the channel space. The base may include a power supply that is electrically coupled to the electrically conductive instruments. The electrically conductive instruments may be configured to independently and directly contact an instance of electrically conductive material of the flavor cartridge, such that the electrically conductive instruments establish an electrical circuit that is closed and extends at least between the electrically conductive instruments through the instance of electrically conductive material of the flavor cartridge.

The base may include control circuitry configured to detect that the electrical circuit is closed, determine that the flavor cartridge is in a position that is proximate to the vapor generator, based on the detecting, and control the forming of the generated vapor by the vapor generator, based on the determining.

The control circuitry may be configured to monitor one or more properties of a current in the electrical circuit, determine that the flavor cartridge is associated with a particular flavor cartridge type, of a plurality of flavor cartridge types, based on the monitoring, and selectively control the forming of the generated vapor according to the particular flavor cartridge type.

At least one electrically conductive instrument of the set of electrically conductive instruments may be configured to directly contact the instance of electrically conductive material based on at least partially impinging into an interior of the flavor cartridge.

The at least one electrically conductive instrument may include an electrically conductive blade that is configured to cut into at least a portion of the flavor cartridge to directly contact the instance of electrically conductive material of the flavor cartridge.

The set of electrically conductive instruments may include a set of electrically conductive blades that are configured to cut into separate portions of the flavor cartridge to directly contact the instance of electrically conductive material of the flavor cartridge, such that the electrically conductive blades are electrically connected to each other through the instance of electrically conductive material of the flavor cartridge.

At least one electrically conductive instrument of the set of electrically conductive instruments may be a plate instrument configured to flush contact the instance of electrically conductive material.

At least one electrically conductive instrument of the set of electrically conductive instruments may be a projection instrument configured to puncture at least a portion of the flavor cartridge to directly contact the instance of electrically conductive material of the flavor cartridge.

The vapor cartridge and the base may be configured to be detachably coupled together.

The base may include a plurality of sets of pogo pin connectors, each set of pogo pin connectors configured to couple with a corresponding set of electrical connectors of the vapor cartridge to supply electrical power from the power supply to the vapor cartridge, communicate data between the base and the vapor cartridge, or enable control circuitry of the base to detect the closed electrical circuit to determine that the flavor cartridge is inserted into the vapor cartridge.

The power supply may include a rechargeable battery.

According to some example embodiments, a flavor cartridge configured to be used in a non-combustible vaping device may include a flavor material extending along a longitudinal axis of the flavor cartridge, an outer shell at least partially enclosing the flavor material, the outer shell extending coaxially with the longitudinal axis of the flavor cartridge, and an instance of electrically conductive material extending at least partially around the flavor cartridge.

The instance of electrically conductive material may be between the flavor material and the outer shell.

The flavor material may include a flavor housing and a flavor matrix within the flavor housing, the flavor housing further including a plurality of perforations configured to direct air to flow in fluid communication with the flavor matrix.

The flavor cartridge may further include an outlet-end insert at an outlet end of the flavor cartridge and a tip-end opening at a tip end of the flavor cartridge. The flavor cartridge may be configured to direct air drawn through the tip-end opening to flow in fluid communication with the flavor material and through the outlet-end insert of the flavor cartridge.

The flavor material may be a tobacco rod including a tobacco material.

The instance of electrically conductive material may be a band extending at least partially around an entirety of the flavor material.

The instance of electrically conductive material may be a cylindrical element extending coaxially with the longitudinal axis of the flavor cartridge.

The instance of electrically conductive material may be a cylindrical disc at an end of the flavor material.

The instance of electrically conductive material may include at least one of a conductive ink and aluminum.

According to some example embodiments, a vapor cartridge for a non-combustible vaping device may include a channel structure, a vapor generator, and a set of electrically conductive instruments. The channel structure may have opposite, first and second ends. The channel structure may include an inner surface at least partially defining a channel space extending at least between the first and second ends. The channel structure may be configured to receive a flavor cartridge into the channel space via the first end of the channel structure. The channel structure may further include a portal that defines an opening in the inner surface of the channel structure. The vapor generator may be at the second end of the channel structure. The vapor generator may be configured to heat a pre-vapor formulation to form a generated vapor and provide the generated vapor to the second end of the channel structure. The channel structure may be further configured to direct the flavor cartridge through the channel space towards the second end of the channel structure, such that the flavor cartridge is positioned to receive the generated vapor from the vapor generator. The set of electrically conductive instruments may extend into the channel space. The electrically conductive instruments may include a displaceable instrument configured to extend at least partially through the portal of the channel structure into the channel space. The electrically conductive instruments may be configured to selectively directly contact each other, such that the electrically conductive instruments are electrically connected to each other, based on the displaceable instrument being displaced by the flavor cartridge at least partially through the portal of the channel structure.

The displaceable instrument may include a fixed portion and a displaceable portion. The fixed portion may be fixed to a portion of the vapor cartridge. The displaceable portion may be configured to extend through the portal of the channel structure.

The set of electrically conductive instruments may be configured to selectively establish a closed electrical circuit that includes the vapor generator, based on the displaceable instrument being displaced by the flavor cartridge at least partially through the portal of the channel structure, such that the set of electrically conductive instruments are configured to selectively enable vapor generation by the vapor generator according to whether the flavor cartridge is inserted into the vapor cartridge.

According to some example embodiments, a base for a non-combustible vaping device may include a power supply, a memory storing a program of instructions, and a processor. The processor may be configured to execute the program of instructions to determine that the base is coupled to a vapor cartridge such that the base is configured to supply electrical power from the power supply to the vapor cartridge, the vapor cartridge configured to heat a pre-vapor formulation to implement an instance of vapor generation based on the electrical power, detect a flavor cartridge inserted into the vapor cartridge, based on receiving an electrical signal at the base from an authentication assembly of the vapor cartridge, based on the detecting, selectively enable the supply of electrical power from the power supply to the vapor cartridge to enable vapor generation by the vapor cartridge, determine a remaining count associated with the inserted flavor cartridge, the remaining count being a particular quantity of instances of vapor generation and/or a particular period of elapsed time, successively decrement the remaining count in response to each successive, respective instance of vapor generation by the vapor cartridge, and in response to a determination that the remaining count is less than a particular threshold value, selectively disable the supply of electrical power from the power supply to the vapor cartridge to disable vapor generation by the vapor cartridge.

The processor may be further configured to execute the program of instructions to, in response to a determination that the flavor cartridge is removed from the vapor cartridge, selectively disable the supply of electrical power from the power supply to the vapor cartridge to disable vapor generation by the vapor cartridge.

The base may further include a display interface configured to present one or more graphical displays, wherein the processor may be further configured to execute the program of instructions to generate a power graphical display indicating an amount of power stored in the power supply, generate a vapor cartridge graphical display indicating whether the base is coupled to the vapor cartridge, generate a flavor cartridge graphical display indicating whether the flavor cartridge is inserted into the vapor cartridge, and display the power graphical display, vapor cartridge graphical display, and flavored cartridge graphical display as a sequence of graphical displays via the display interface.

The power graphical display may include a power storage icon indicating a quantity of instances of vapor generation, by the vapor cartridge, that may be supported by the amount of power stored in the power supply.

The vapor cartridge graphical display may indicate whether the vapor cartridge holds at least a threshold amount of pre-vapor formulation, such that the vapor cartridge is configured generate at least one instance of vapor.

The flavor cartridge graphical display may indicate a quantity of instances of vapor generation, associated with the inserted flavor cartridge, remaining until vapor generation by the vapor cartridge is disabled, and/or a magnitude of elapsed time, associated with the inserted flavor cartridge, remaining until vapor generation by the vapor cartridge is disabled.

The base may further include a tactile interface. The processor may be further configured to execute the program of instructions to switch between separate graphical displays of the sequence of graphical displays based on successive command signals received from the tactile interface.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims.

The accompanying drawings are not to be considered as drawn to scale unless explicitly noted. For purposes of clarity, various dimensions of the drawings may have been exaggerated.

FIG. 3A, FIG. 3B, and FIG. 3C are each a perspective view of an authentication assembly according to some example embodiments.

FIG. 4A, FIG. 4B, and FIG. 4C are each a cross-sectional view of a vapor cartridge of a non-combustible vaping device illustrating an insertion of a flavor cartridge through a channel space of the vapor cartridge according to some example embodiments.

FIG. 5A and FIG. 5B are each a cross-sectional view of a vapor cartridge of a non-combustible vaping device illustrating an insertion of a flavor cartridge through a channel space of the vapor cartridge according to some example embodiments.

FIG. 6B is a cross-sectional view of the base of FIG. 6A along line VIB-VIB'.

FIG. 6C is a cross-sectional view of the base of FIG. 6A along line VIC-VIC'.

FIG. 6D is a cross-sectional view of the base of FIG. 6A along line VID-VID'.

DETAILED DESCRIPTION OF EXAMPLE EMBODIMENTS

Figure 1A:
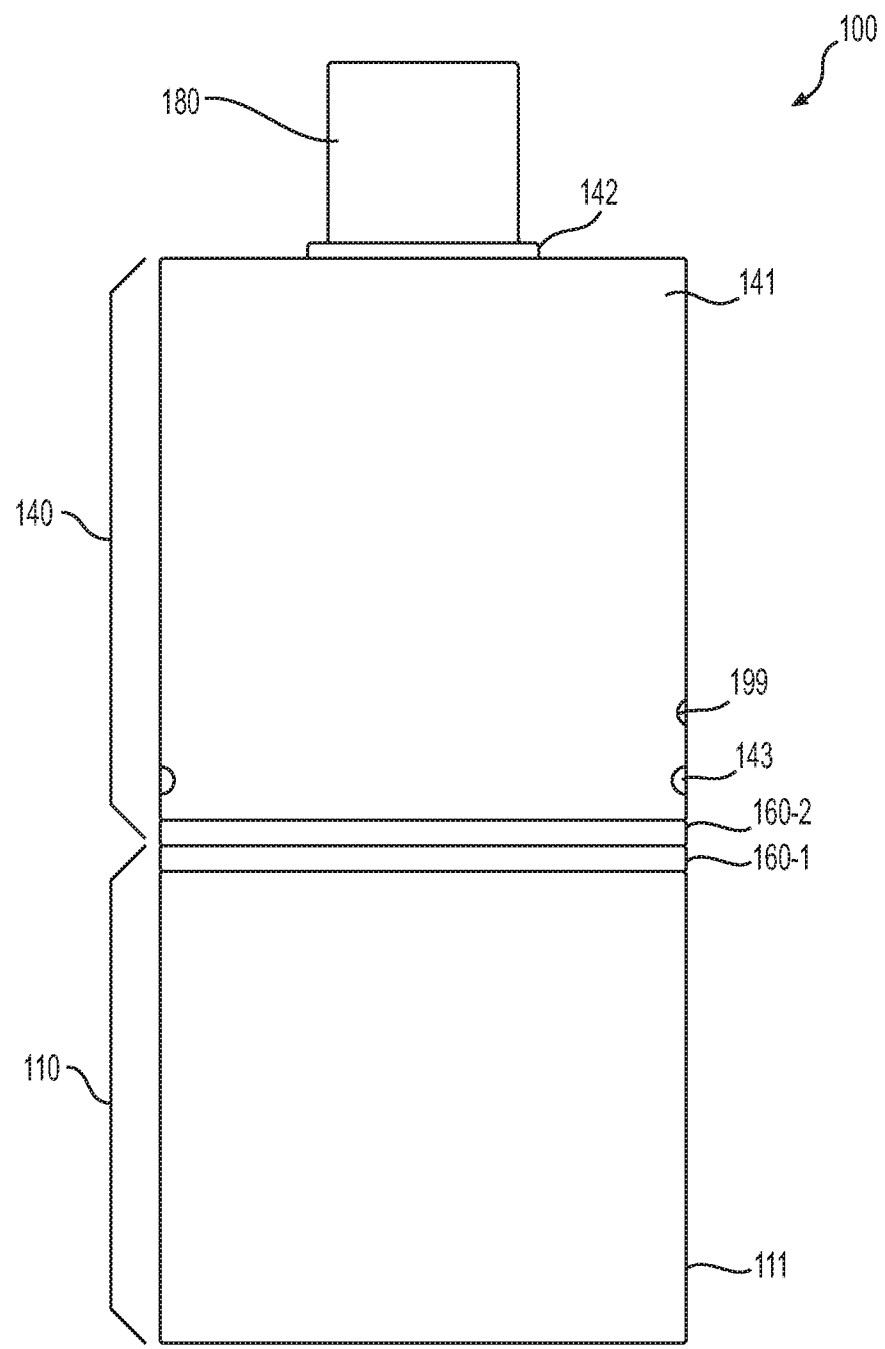
FIG. 1A is a side view of a non-combustible vaping device according to some example embodiments.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, some combination thereof, or the like may be used herein to describe various elements, elements, regions, layers and/or sections, these elements, elements, regions, layers, and/or sections should not be limited by these terms.

These terms are only used to distinguish one element, element, region, layer, or section from another region, layer, or section. Thus, a first element, element, region, layer, or section discussed below could be termed a second element, element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or elements, but do not preclude the presence or addition of one or more other features, integers, steps, operations, elements, elements, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

When the terms "about" or "substantially" are used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages. The expression "up to" includes amounts of zero to the expressed upper limit and all values therebetween.

When ranges are specified, the range includes all values therebetween such as increments of 0.1%. Moreover, when the words "generally" and "substantially" are used in connection with geometric shapes, it is intended that precision of the geometric shape is not required but that latitude for the shape is within the scope of the disclosure. Although the tubular elements of the embodiments may be cylindrical, other tubular cross-sectional forms are contemplated, such as square, rectangular, oval, triangular and others.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

Non-Combustible Vaping Device

Figure 1B:
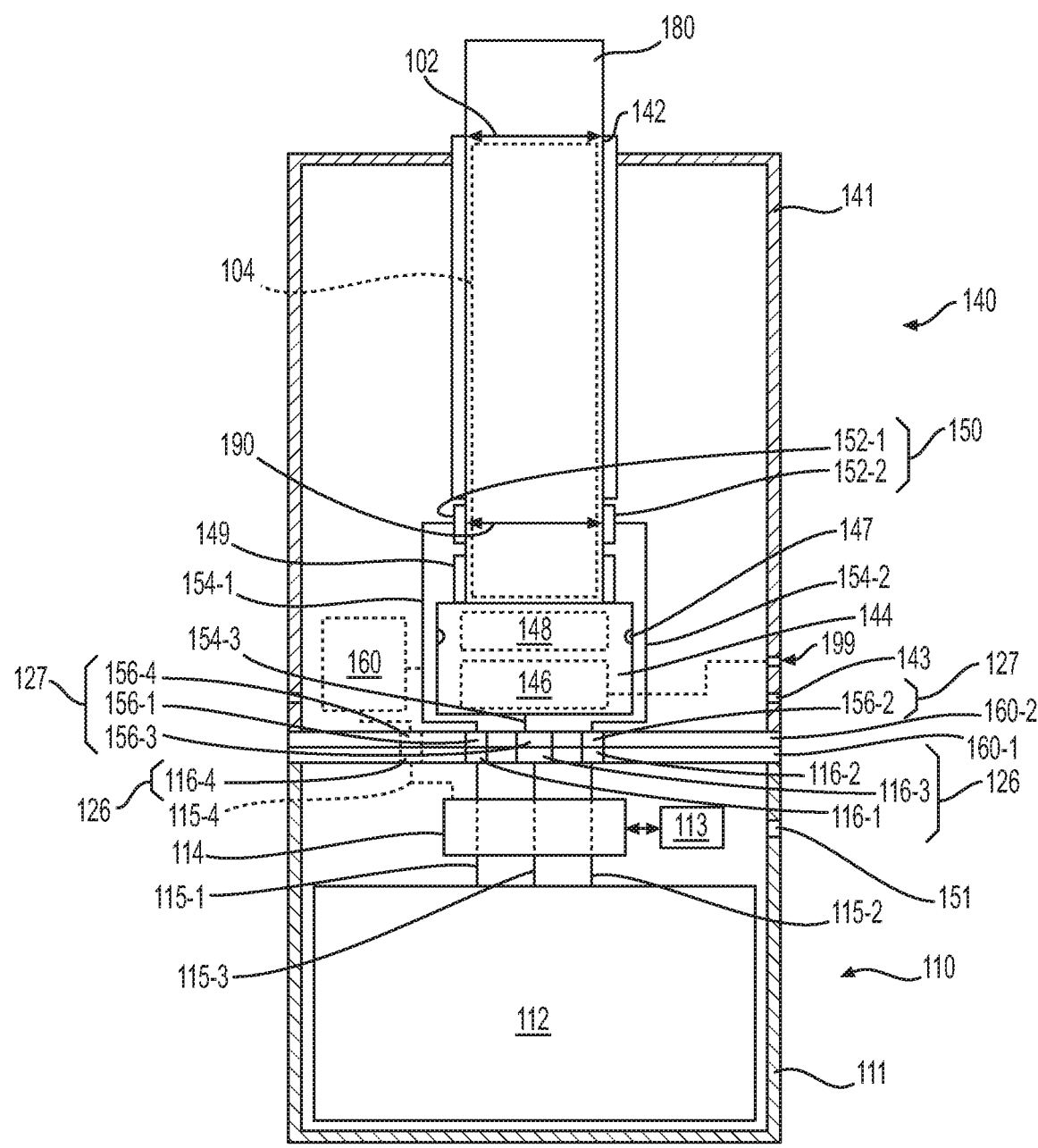
FIG. 1B is a cross-sectional view of the non-combustible vaping device of FIG. 1A.

FIG. 1A is a side view of a non-combustible vaping device according to some example embodiments. FIG. 1B is a cross-sectional view of the non-combustible vaping device of FIG. 1A.

Referring to FIGS. 1A-1B, a non-combustible vaping device 100 includes a first section ("base 110"), a second section ("vapor cartridge 140"), and a flavor cartridge 180. The vapor cartridge 140 is configured to generate a vapor, referred to herein as a "generated vapor." The vapor cartridge 140 is further configured to receive the flavor cartridge 180, such that the flavor cartridge 180 is "inserted" into the vapor cartridge 140, and direct the generated vapor into the flavor cartridge 180.

The flavor cartridge 180 may be configured to generate a flavored vapor, based on directing the generated vapor through an interior of the flavor cartridge 180. The base 110 is configured to at least supply electrical power to the vapor cartridge 140 to enable the vapor cartridge 140 to generate ("form") the generated vapor.

As described further below, the non-combustible vaping device 100 may include an authentication assembly 150, including a set of electrically conductive instruments 152-1 and 152-2, that is configured to establish an electrical connection between the electrically conductive instruments 152-1 and 152-2, through the flavor cartridge 180, based on the flavor cartridge 180 being inserted into a channel space 104 of the non-combustible vaping device 100. Based on such an electrical connection, a determination can be made that the flavor cartridge 180 is inserted into the non-combustible vaping device 100. One or more portions of the non-combustible vaping device 100 may be controlled according to such a determination, including a vapor generator 144.

The base 110 and the vapor cartridge 140 include interfaces 160-1 and 160-2, respectively, and the base 110 and vapor cartridge 140 are configured to be coupled together via the respective interfaces 160-1 and 160-2.

As shown in FIG. 1B, each interface 160-1 and 160-2 may include one or more sets of electrical connectors 126 and 127, respectively. Each set of electrical connectors 126 and 127 may include one or more electrical connectors 116-1 to 116-4 and 156-1 to 156-4, respectively. As described further herein, one or more of the electrical connectors 116-1 to 116-4 and 156-1 to 156-4 may be a pogo pin connector.

The interfaces 160-1 and 160-2 may be configured to be detachably coupled together or permanently coupled together. In some example embodiments, the interfaces 160-1, 160-2 are threaded connectors. It should be appreciated that the coupling of interfaces 160-1, 160-2 may be any type of connector, including, without limitation, a snug-fit, detent, clamp, bayonet, and/or clasp.

In some example embodiments, the vapor cartridge 140 and the base 110 may be integrated into an individual, integral element, such that interfaces 160-1 and 160-2 are absent.

Referring to FIGS. 1A-1B, the vapor cartridge 140 may include a housing 141 and a channel structure 142 that extends at least partially through an interior of the vapor cartridge 140 and at least partially defines the channel space 104. As shown in FIG. 1B, the channel structure 142 may be an at least partially cylindrical element that at least partially defines the channel space 104. The channel structure 142 may have an inner surface that at least partially defines one or more longitudinal boundaries of the channel space 104 (e.g., one or more boundaries extending coaxially with the longitudinal axis of the channel space 104). The channel structure 142 has open first and second ends, where the first end of the channel structure 142 is proximate to the vapor generator 144 and the second end of the channel structure 142 is in fluid communication with an exterior of device 100.

As shown in FIG. 1B, the second end of the channel structure 142 may define an opening 102 in the vapor cartridge 140. As a result, the channel space 104 is open to the exterior of the non-combustible vaping device 100 via the second end of the channel structure 142.

Referring to FIG. 1B, the vapor cartridge 140 may include the vapor generator 144 that is configured to generate a generated vapor. As shown in FIG. 1B, the vapor generator 144 may include a pre-vapor formulation reservoir 146 and a heating element 148.

The heating element 148 is coupled to the pre-vapor formulation reservoir 146 and is configured to generate heat. At least a portion of the vapor generator 144 may include a dispensing interface (not shown in FIG. 1B) that is configured to draw pre-vapor formulation from the pre-vapor formulation reservoir 146, such that the pre-vapor formulation may be vaporized from the dispensing interface based on heating of the dispensing interface by the heating element 148. In some example embodiments, the heating element 148 may include a mesh heater structure.

During vaping, pre-vapor formulation may be transferred from the pre-vapor formulation reservoir 146 and/or storage medium in the proximity of the heating element 148 via capillary action of a dispensing interface. The heating element 148 may at least partially surround a central portion ("trunk") of the dispensing interface such that when the heating element 148 is activated to generate heat, the pre-vapor formulation in the central portion of the dispensing interface may be vaporized by the heating element 148 to form a generated vapor.

The pre-vapor formulation reservoir 146 may include a pre-vapor formulation that is free of flavorants, such that when the heating element 148 vaporizes pre-vapor formulation in the dispensing interface to form a vapor, the vapor, also referred to herein as a "generated vapor," may be substantially absent of flavor. In some example embodiments, the pre-vapor formulation reservoir 146 may include a pre-vapor formulation that includes one or more flavorants.

The vapor generator 144 is proximate to the first end ("tip end") of the channel structure 142, such that the vapor generator 144 is configured to generate a generated vapor that may pass through the channel space 104, via the first end of the channel structure 142, pass through the channel space 104 defined by the channel structure 142 and exit the vapor cartridge 140 via the second end (e.g., opening 102) of the channel structure 142.

The vapor cartridge 140 includes air inlet ports 143 at the housing 141 and air inlet ports 147 at the vapor generator 144. Air inlet ports 143 extend through the housing 141 and enable air to pass into the vapor cartridge 140, through the housing 141, from an external environment ("ambient environment") based on air being drawn through the second end of the channel structure 142. Air inlet ports 147 extend through a housing of the vapor generator 144 and enable air to pass into the vapor generator 144, in fluid communication with the heating element 148, based on air being drawn through the second end of the channel structure 142. A generated vapor that is generated by the vapor generator 144, based on the heating element 148 heating and vaporizing at least a portion of pre-vapor formulation drawn from the pre-vapor formulation reservoir 146, may be entrained in air that is drawn through the vapor generator 144, via air inlet ports 143 and air inlet ports 147, towards the second end of the channel structure 142. Thus, the generated vapor may pass out of the vapor cartridge 140 via the second end of the channel structure 142.

In some example embodiments, the air inlet ports 143, 147 may be drilled with carbide drill bits or other high-precision tools and/or techniques. In some example embodiments, the housing 141 and the outer housing of the vapor generator 144 may be formed of metal or metal alloys such that the size and shape of the air inlet ports 143 and the air inlet ports 147 may not be altered during manufacturing operations, packaging, and vaping. Thus, the air inlet ports 143 and the air inlet ports 147 may provide consistent resistance to draw ("RTD"). In some example embodiments, the air inlet ports 143 and the air inlet ports 147 may be sized and configured such that the non-combustible vaping device 100 has a RTD in the range of from about 60 mm $H_2O$ to about 150 mm $H_2O$.

Still referring to FIGS. 1A-1B, the non-combustible vaping device 100 may include a flavor cartridge 180 that is configured to be coupled to the vapor generator 144 such that the flavor cartridge 180 is positioned, at a first end of the flavor cartridge 180, proximate to the vapor generator 144. Based on the first end of the flavor cartridge 180 being positioned proximate to the vapor generator, the flavor cartridge 180 may be configured to receive a generated vapor that is generated by the vapor generator 144.

As discussed further below with regard to at least FIGS. 2A-2D, the flavor cartridge 180 may include a containment structure enclosing an interior of the flavor cartridge 180. The flavor cartridge 180 may include a flavor material. The flavor material may include one or more flavorants.

As used herein, the term "flavorant" is used to describe a compound or combination of compounds that may provide flavor and/or aroma to an adult vaper. In some example embodiments, a flavorant is configured to interact with at least one adult vaper sensory receptor. A flavorant may be configured to interact with the sensory receptor via at least one of orthonasal stimulation and retronasal stimulation. A flavorant may include one or more volatile flavor substances. The at least one flavorant may include one or more of a natural flavorant or an artificial ("synthetic") flavorant. The at least one flavorant may include one or more plant extract materials. In some example embodiments, the at least one flavorant is one or more of tobacco flavor, menthol, wintergreen, peppermint, herb flavors, fruit flavors, nut flavors, liquor flavors, and combinations thereof. In some example embodiments, the flavorant is included in a botanical material. A botanical material may include material of one or more plants. A botanical material may include one or more herbs, spices, fruits, roots, leaves, grasses, or the like. For example, a botanical material may include orange rind material and sweetgrass material. In another example, a botanical material may include tobacco material. In some example embodiments, a flavorant that is a tobacco flavor (a "tobacco flavorant") includes at least one of a synthetic material and a plant extract material. A plant extract material included in a tobacco flavorant may be an extract from one or more tobacco materials.

In some example embodiments, a tobacco material may include material from any member of the genus *Nicotiana*. In some example embodiments, the tobacco material includes a blend of two or more different tobacco varieties.

Examples of suitable types of tobacco materials that may be used include, but are not limited to, flue-cured tobacco, Burley tobacco, Dark tobacco, Maryland tobacco, Oriental tobacco, rare tobacco, specialty tobacco, blends thereof and the like. The tobacco material may be provided in any suitable form, including, but not limited to, tobacco lamina, processed tobacco materials, such as volume expanded or puffed tobacco, processed tobacco stems, such as cut-rolled or cut-puffed stems, reconstituted tobacco materials, blends thereof, and the like. In some example embodiments, the tobacco material is in the form of a substantially dry tobacco mass.

In some example embodiments, a flavor cartridge 180 that includes a tobacco flavor material is referred to as a tobacco element. In some example embodiments, the flavor cartridge 180 includes a tobacco rod that holds a flavor material that is one or more types of tobacco (also referred to as a tobacco flavor material). A tobacco rod may include one or more of a cigarette, cigar, cigarillo, some combination thereof, or the like. The tobacco rod may include a filter element that is configured to filter one or more instances of particular matter from a vapor. The filter element may be configured to provide structural support to the tobacco rod, provide familiarity to adult vapers with regard to cigarettes, control an amount of vapor directed to an exterior of the non-combustible vaping device 100, and/or offers potentials of introducing additional flavorants to the vapor (e.g., via entrainment of flavor materials included in the filter element into a vapor passing through the filter element).

In some example embodiments, the flavor cartridge 180 may not include any flavor material. Such a flavor cartridge 180 that does not include flavor material may be referred to herein as an "outlet structure." The outlet structure may be a hollow cylindrical structure that is configured to direct a generated vapor, generated by the vapor generator 144, through the channel space 104 to an exterior of the non-combustible vaping device 100. The outlet structure, similarly to flavor cartridge 180 that include flavor material, may be configured to engage the authentication assembly 150. For example, the outlet structure may include a band of electrically conductive material extending at least partially around an outer surface of the outer housing of the outlet structure. The outer housing of the outlet structure may have a substantially similar external size and structure as an outer housing of a flavor cartridge 180 that includes a flavor material. In some example embodiments, if and/or when the flavor cartridge 180 is an outlet structure that does not include any flavor material, the pre-vapor formulation reservoir 146 may hold a pre-vapor formulation that includes one or more flavorants, such that the vapor generator 144 is configured to generate a flavored vapor.

Still referring to FIGS. 1A-1B, the flavor cartridge 180 may be inserted into the vapor cartridge 140, through the channel structure 142 and the channel space 104 at least partially defined thereby, such that the flavor cartridge 180 passes through the channel space 104 towards the vapor generator 144 in the vapor cartridge 140. As shown in FIGS. 1A-1B, a first end of the flavor cartridge 180 may be engaged with an interface 149 on the vapor generator 144, such that the first end of the flavor cartridge 180 is coupled with the vapor generator 144. The interface 149 may include a gasket assembly that is configured to establish a seal with the outer housing of the flavor cartridge 180, such that the seal restricts a flow pathway of the generated vapor generated by the vapor generator 144 to being directed through the flavor cartridge 180. As a result, the interface 149 may direct the generated vapor to passing through the flavor cartridge 180 to be converted to flavored vapor by the flavor cartridge 180.

In some example embodiments, an inner surface of the channel structure 142 that at least partially defines the channel space 104 is configured to establish the seal with the outer housing of the flavor cartridge 180 if and/or when the flavor cartridge 180 is inserted into the channel space 104. For example, in some example embodiments, the diameter of the inner surface of the channel structure 142 may be at least partially constricted such that a diameter of the channel space 104 is at least partially constricted within a portion of the channel space. Thus, the channel structure 142 may define a constricted portion of the channel space 104. If and/or when the flavor cartridge 180 passes through the constricted portion of the channel space 104, the flavor cartridge 180 may engage the inner surface of the channel structure 142 in the constricted portion such that the channel structure 142 establishes a seal with the outer housing of the flavor cartridge 180.

In some example embodiments, the flavor cartridge 180 may be detachably coupled with the interface 149, such that one or more flavor cartridges 180 may be swapped from the non-combustible vaping device 100.

In some example embodiments, at least the vapor generator 144 of the non-combustible vaping device 100 is configured to form at least a generated vapor. The vapor cartridge 140 may direct the generated vapor through the flavor cartridge 180 positioned such that a first end of the flavor cartridge 180 is positioned proximate to the vapor generator 144 such that one or more flavorants are eluted from a flavor material of the flavor cartridge 180 into the generated vapor to form a flavored vapor. The non-combustible vaping device 100 is configured to enable such elution independently of any combustion of the flavor material included in the flavor cartridge 180.

The flavor material included in the flavor cartridge 180 may include a porous structure that includes one or more instances of flavor material. The porous structure may hold a flavorant in flow communication with the vapor generator 144 so that generated vapor formed in the vapor generator 144, received at the first end of the flavor cartridge 180, and passing through the flavor cartridge 180 may pass at least partially through the porous structure and in flow communication with the flavorants held by the porous structure. The generated vapor may act as an eluent, eluting the flavorant from the flavor cartridge 180 and into the generated vapor to form an eluate. The eluate may include the generated vapor and the flavorant. Such an eluate may be referred to as the flavored vapor.

In some example embodiments, the flavorants eluted into the generated vapor are in a particulate phase. A particulate phase may include a liquid phase, solid phase, or the like. In some example embodiments, the flavorants eluted into the generated vapor are in a vapor phase, gas phase, some combination thereof, or the like. A flavorant may include a volatile flavor substance, and the volatile flavor substance may be eluted into the generated vapor. In some example embodiments, a flavorant eluted into the generated vapor includes a nonvolatile flavor substance.

In some example embodiments, the flavor cartridge 180 may be replaced with another flavor cartridge 180 to swap the flavorant included in the non-combustible vaping device 100 as desired by an adult vaper. The flavor cartridge 180 may be replaced with another flavor cartridge 180 to replenish flavorants in the non-combustible vaping device 100 without replacing the vapor cartridge 140 and/or pre-vapor formulation held therein, where the pre-vapor formulation reservoir 146 may include sufficient pre-vapor formulation to support additional vaping. In some example embodiments, the pre-vapor formulation reservoir 146 includes a particular amount of pre-vapor formulation associated with a maximum quantity of instances of vapor generation associated with a particular quantity of flavor cartridges 180, such that the vapor generator 144 is configured to support a quantity of instances of vapor generation that is equal to or less than the maximum quantity of instances of vapor generation that may be supported by the particular quantity of flavor cartridges 180. A maximum quantity of instances of vapor generation that may be associated with a given flavor cartridge 180 is described further below as being associated with an initial "remaining count" associated with the flavor cartridge 180.

Referring to FIG. 1B, the vapor cartridge 140 may include an authentication assembly 150 that is configured to generate an indication, comprising an electrical signal, if and/or when the flavor cartridge 180 is inserted into the vapor cartridge 140. Such an electrical signal, which may include an electrical current, may provide an indication that the flavor cartridge is inserted into the vapor cartridge 140. One or more elements of the vapor cartridge 140, including the vapor generator 144, may be controlled based on the electrical signal, thereby enabling the one or more elements of the vapor cartridge 140 to be controlled based on a determination of whether a flavor cartridge 180 is inserted into the vapor cartridge 140.

In some example embodiments, including the example embodiments shown in FIG. 1B, the authentication assembly 150 may be configured to generate the indication ("electrical signal") indicating that the flavor cartridge 180 is inserted into the vapor cartridge 140 based on an electrical connection being established between at least two electrically conductive instruments 152-1 to 152-2 of the authentication assembly 150, where the electrical connection extends at least partially through the flavor cartridge 180. Restated, the authentication assembly 150 may be configured to generate the indication ("electrical signal") indicating that the flavor cartridge 180 is inserted into the vapor cartridge 140 based on the flavor cartridge 180 establishing and/or bridging an electrical connection between the at least two electrically conductive instruments 152-1 to 152-2 of the authentication assembly 150.

In some example embodiments, including the example embodiments described below with regard to FIGS. 5A-5B, the authentication assembly 150 may be configured to generate the indication ("electrical signal"), indicating that the flavor cartridge 180 is inserted into the vapor cartridge 140, based on the flavor cartridge 180 physically displacing an electrically conductive instrument. The physically displaced electrically conductive instrument may close ("establish") an electrical circuit. As a result, the electrical signal may be generated as an electrical current that passes through the closed electrical circuit in the vapor cartridge 140, based on the electrically conductive instrument being displaced by the flavor cartridge 180. In such example embodiments, the electrically conductive instrument may be configured to operate as an electrical switch that may be actuated by the flavor cartridge 180, based on the flavor cartridge 180 being at least partially inserted into the vapor cartridge 140.

As shown in FIG. 1B, the authentication assembly 150 may include a set of electrically conductive instruments 152-1 to 152-2. As described further below, the electrically conductive instruments may include one or more various types of instruments, including one or more plate instruments (also referred to herein as electrically conductive plates), blade instruments (also referred to herein as electrically conductive blades), spike instruments (also referred to herein as electrically conductive spikes and/or projection instruments), some combination thereof, or the like. An electrically conductive instrument may be at least partially comprised of an electrically conductive material. While the authentication assembly 150 included in the example embodiments illustrated in FIG. 1B includes two electrically conductive instruments 152-1 to 152-2, it will be understood that the authentication assembly 150 may include more than two electrically conductive instruments.

The set of electrically conductive instruments 152-1 to 152-2 extend into the channel space 104 that is at least partially defined by the channel structure 142. In some example embodiments, the electrically conductive instruments 152-1 to 152-2 may extend at least partially through the structure and/or inner surface of the channel structure 142 and into the portion of the channel space 104 directly defined by the channel structure 142. In the example embodiments illustrated in FIG. 1B, the electrically conductive instruments 152-1 to 152-2 are positioned proximate to the first end of the channel structure 142, such that the electrically conductive instruments 152-1 to 152-2 extend into a portion of the channel space 104 that is between the channel structure 142 and the vapor generator 144.

The electrically conductive instruments 152-1 to 152-2 are spaced apart (e.g., "isolated from direct contact with each other") according to gap space 190. The gap space 190 may be equal to or less than the diameter of the channel space 104. The flavor cartridge 180 may have an outer diameter that is equal to or greater than the gap space 190. As a result, and as shown in FIG. 1B, the electrically conductive instruments 152-1 to 152-2 may be configured to independently (e.g., "separately") and directly contact the flavor cartridge 180 as the flavor cartridge 180 is inserted into the vapor cartridge 140 through the channel space 104.

As described further, the flavor cartridge 180 may include an electrically conductive material. The electrically conductive instruments 152-1 to 152-2, based on independently and directly contacting the flavor cartridge 180, may independently and directly contact the conductive material included in the flavor cartridge 180. Such direct contact may include at least partially impinging into an interior of the flavor cartridge 180.

Based on independently and directly contacting the conductive material included in the flavor cartridge 180, the electrically conductive instruments 152-1 to 152-2 may establish an electrical connection between the electrically conductive instruments 152-1 to 152-2, where the electrical connection extends through the conductive material of the flavor cartridge 180. Thus, the electrical connection is established based on the conductive material being inserted through the channel space 104 and directly and independently contacting the electrically conductive instruments 152-1 to 152-2.

Establishing the electrical connection may include establishing a closed electrical circuit that includes an electrical power supply and extends through the electrical connection, such that an electrical current is caused to flow through the closed electrical circuit based on the electrical connection being established.

Still referring to FIG. 1B, the electrically conductive instruments 152-1 to 152-2 are each connected to separate electrical leads 154-1 to 154-2, respectively.

The electrical leads 154-1 to 154-2 are connected to separate, independent electrical connectors ("electrical interfaces") 156-1 to 156-2. In some example embodiments, one or more connectors of the electrical connectors 156-1 to 156-2 may be at least partially integrated into interface 160-2. As described further below, one or more of the electrical connectors 156-1 to 156-4 described herein may be a spring loaded connector, commonly known as a "pogo pin connector," or may be an interface configured to connect with a pogo pin connector (e.g., one or more electrical connectors of the below-described electrical connectors 116-1 to 116-4 may be a pogo pin connector).

In some example embodiments, one or more of the electrical connectors 156-1 and 156-2 include one or more of a cathode connector element and an anode connector element. If and/or when interfaces 160-1 and 160-2 are coupled together, the coupled interfaces 160-1, 160-2 may electrically couple electrical connectors 156-1, 156-2 and 116-1, 116-2 together, respectively.

If and/or when interfaces 160-1, 160-2 are coupled together, one or more electrical circuits through the vapor generator 144 and a power supply 112 in the base 110 may be established. The established electrical circuits may include at least the heating element 148, the control circuitry 114 in the base 110, and the power supply 112 in the base 110, such that the elements in the established electrical circuits are electrically coupled to each other. The electrical circuit may include electrical leads 154-3 and 115-3, control circuitry 114, power supply 112, and electrical connectors 156-3 and 116-3, such that the elements in the electrical circuit are electrically coupled to each other.

As described further below, the electrical connectors 156-1 to 156-2 may be electrically connected to the power supply 112. As a result, the electrically conductive instruments 152-1 to 152-2 may be configured to, based on independently and directly contacting a conductive material included in the flavor cartridge 180, establish a closed electrical circuit that extends between the power supply and the electrically conductive instruments 152-1 and 152-2 and further between the electrically conductive instruments 152-1 and 152-2 through the conductive material of the flavor cartridge 180. The closed electrical circuit may extend from the power supply 112, through electrical connector 156-1, through electrical lead 154-1, through electrically conductive instrument 152-1, through the instance of electrically conductive material of the flavor cartridge 180, through the electrically conductive instrument 152-2, through electrical lead 154-2, and through the electrical connector 156-2 to the power supply. Thus, the closed electrical circuit may be selectively established based on the flavor cartridge 180 being inserted through the channel structure 142 such that the electrically conductive instruments 152-1 to 152-2 independently and directly contact the conductive material included in the flavor cartridge 180.

Referring to FIGS. 1A-1B, the base 110 may include an outer housing 111, extending in a longitudinal direction, a sensor 113 responsive to air drawn into the non-combustible vaping device 100 via air inlet port 151, at least one power supply 112, and control circuitry 114. The power supply 112 may include a rechargeable battery. The sensor 113 may be one or more of a pressure sensor, a microelectromechanical system (MEMS) sensor, some combination thereof, or the like. In some example embodiments, the base 110 may include one or more elements not shown in FIGS. 1A-1B. For example, the base 110 may include one or more interface devices, including a display interface, a tactile ("button") interface, a communication interface (e.g., transceiver, communication port, some combination thereof, or the like), a power interface (e.g., power port), some combination thereof, or the like.

In some example embodiments, the power supply 112 includes a battery arranged in the non-combustible vaping device 100 such that the anode is downstream of the cathode. The heating element 148 of the vapor cartridge 140 may be coupled to the power supply 112 by at least the electrical leads 154-3, the electrical connectors 156-3 and 116-3, electrical lead 115-3, and control circuitry 114.

The power supply 112 may be a Lithium-ion battery or one of its variants, for example a Lithium-ion polymer battery. Alternatively, the power supply 112 may be a nickel-metal hydride battery, a nickel cadmium battery, a lithium-manganese battery, a lithium-cobalt battery or a fuel cell. The non-combustible vaping device 100 may be usable by an adult vaper until the energy in the power supply 112 is depleted or in the case of lithium polymer battery, a minimum voltage cut-off level is achieved.

Further, the power supply 112 may be rechargeable and may include circuitry configured to allow the battery to be chargeable by an external charging device. To recharge the power supply 112, a Universal Serial Bus (USB) charger or other suitable charger assembly may be used.

Upon a connection between the vapor cartridge 140 and the base 110 being completed, the at least one power supply 112 may be electrically connected with the heating element 148 of the vapor generator 144 upon actuation of the sensor 113.

The sensor 113 may be configured to sense an air pressure drop and initiate application of voltage from the power supply 112 to the heating element 148. In addition, the at least one air inlet port 151 may be located adjacent to the sensor 113, such that the sensor 113 may sense air flow indicative of vapor being drawn through the opening 102 of the vapor cartridge 140. The sensor 113 may activate the power supply 112.

In some example embodiments, the base 110 is configured such that the air inlet port 151 is at least partially established by the coupling of the vapor cartridge 140 to the base 110. For example, as described further below with reference to at least FIGS. 7A-8D, the base 110 may include, in addition to an air inlet port 151 that is in direct fluid communication with the sensor 113, one or more channel structures in a portion of an outer housing 111 of the base 110. The base 110 may be configured such that the vapor cartridge 140, upon coupling with the base 110, encloses the channel structures in the outer housing 111 to establish one or more conduits, bounded by the housings 111 and 141 of the base 110 and vapor cartridge 140, respectively, that extend from an ambient environment to the air inlet port 151, where the air inlet port is obscured from (e.g., isolated from direct exposure to) the ambient environment by the vapor cartridge 140. Air may be drawn to the sensor 113 via the established conduit and the air inlet port 151.

In some example embodiments, the control circuitry 114 may control the supply of electrical power from the power supply 112 to the heating element 148 responsive to the air pressure drop sensed by sensor 113. In some example embodiments, the control circuitry 114 may include a maximum, time-period limiter. In some example embodiments, the control circuitry 114 may include a manually operable switch for an adult vaper to manually initiate vaping. The time-period of the electric current supply to the heating element 148 may be pre-set depending on the amount of pre-vapor formulation desired to be vaporized. In some example embodiments, the control circuitry 114 may control the supply of electrical power to the heating element 148 as long as the sensor 113 detects a pressure drop.

To control the supply of electrical power to a heating element 148, the control circuitry 114 may execute one or more instances of computer-executable program code. The control circuitry 114 may include a processor and a memory. The memory may be a computer-readable storage medium storing computer-executable code.

The control circuitry 114 may include processing circuitry including, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. In some example embodiments, the control circuitry 114 may be at least one of an application-specific integrated circuit (ASIC) and an ASIC chip.

The control circuitry 114 may be configured as a special purpose machine by executing computer-readable program code stored on a storage device. The program code may include program or computer-readable instructions, software elements, software modules, data files, data structures, and/or the like, capable of being implemented by one or more hardware devices, such as one or more instances of the control circuitry 114 mentioned above. Examples of program code include both machine code produced by a compiler and higher level program code that is executed using an interpreter.

The control circuitry 114 may include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a USB flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired communication interface, a wireless communication interface, and/or any other like medium.

In some example embodiments, the non-combustible vaping device 100 includes a communication interface via which at least the control circuitry 114 may communicate with a remotely-located external device. The communication interface may include a wireless communication interface, a wired communication interface, some combination thereof, or the like. For example, the non-combustible vaping device 100 may include a USB interface, and the control circuitry 114 may be configured to communicate with a remotely-located external device, via a communication connection at least partially implemented by the USB interface and a USB cable coupled with both the USB interface and the remotely-located external device. In another example, the non-combustible vaping device 100 may include a wireless communication transceiver, and the control circuitry 114 may be configured to communicate with a remotely-located external device via at least a wireless communication connection established with the remotely-located device via at least the wireless communication transceiver. A wireless communication transceiver may include an ad hoc wireless communication (e.g., BLUETOOTH) transceiver.

The control circuitry 114 may be a special purpose machine configured to execute the computer-executable code to control the supply of electrical power to the heating element 148. Controlling the supply of electrical power to the heating element 148 may be referred to herein interchangeably as activating the heating element 148.

In some example embodiments, the control circuitry 114 may be configured to selectively and/or adjustably control (e.g., enable and/or disable) the supply of electrical power to the vapor generator 144, thereby selectively controlling and/or adjustably controlling the forming of a generated vapor, also referred to herein as selectively controlling the implementation of one or more instances of vapor generation by at least the vapor cartridge 140, based on a determination of whether an electrical current that extends between the electrically conductive instruments 152-1 and 152-2, via the conductive material of the flavor cartridge 180, is present and/or meets one or more threshold parameters. Such a determination may be referred to herein as a detection, and/or "initial detection," that the flavor cartridge 180 is inserted into the vapor cartridge 140.

The control circuitry 114 may be configured to enable vapor generation by the vapor generator 144, in response to data generated by sensor 113, for at least a particular quantity of instances of vapor generation and/or a particular duration of time associated with the flavor cartridge 180, based on the control circuitry 114 determining that the electrical current that extends between the electrically conductive instruments 152-1 and 152-2, via the conductive material of the flavor cartridge 180, is present.

As referred to herein, a particular quantity of instances of vapor generation, a particular cumulative duration of vapor generation, and/or a particular duration of time ("period of elapsed time") associated with a flavor cartridge 180 may be referred to herein as a "remaining count" associated with the flavor cartridge 180. In some example embodiments, in response to the flavor cartridge 180 being detected as being inserted into the vapor cartridge 140, based on detection of the aforementioned electrical current at control circuitry 114, the control circuitry 114 may selectively enable the supply of electrical power from power supply 112 to the vapor generator 144 and may further determine an initial "remaining count" associated with the flavor cartridge 180. The initial remaining count associated with the flavor cartridge 180 may be referred to as the maximum remaining count associated with the flavor cartridge 180. For example, in response to a flavor cartridge 180 initially being inserted into the vapor cartridge 140, a maximum quantity of instances of vapor generation, a maximum cumulative duration of vapor generation, and/or a maximum period of time associated with the inserted flavor cartridge 180 may be determined.

Subsequently to the control circuitry 114 initially detecting the flavor cartridge 180 and enabling the vapor generator 144, the control circuitry 114 may "decrement" (e.g., "count down") the remaining count associated with the inserted flavor cartridge 180 until the value of the remaining count is depleted and/or is decremented below the value of a threshold remaining count value.

If and/or when the remaining count is a particular quantity of instances of vapor generation, the control circuitry 114 may decrement the quantity (e.g., reduce the quantity) in response to each successive implementation of an instance of vapor generation by the vapor cartridge 140. Restated, in response to vaping commands being received at the control circuitry 114, simultaneously with the supply of electrical power from power supply 112 to the vapor generator 144 remaining enabled, the control circuitry 114 may cause electrical power to be supplied to the vapor generator 144 to cause implementation of an instance of vapor generation by at least the vapor cartridge 140 and may further decrement the quantity of instances of vapor generation associated with the inserted flavor cartridge 180.

If and/or when the remaining count is a cumulative duration of vapor generations implemented by the vapor cartridge 140 subsequent to the insertion of the flavor cartridge 180, the control circuitry 114 may decrement the magnitude of the cumulative duration, in response to each successive implementation of an instance of vapor generation by the vapor cartridge 140, by an amount equal to the duration of time during which vapor is generated by the vapor cartridge during the given instance of vapor generation.

If and/or when the remaining count is a particular duration of elapsed time, the control circuitry 114 may decrement the elapsed time (e.g., initiate a countdown of the elapsed time from the initial duration) in response to an occurrence of an event. Such an event may be the initial detection of the flavor cartridge 180 in the vapor cartridge 140, an implementation of a first instance of vapor generation subsequent to the initial detection, some combination thereof, or the like.

Based on a determination that the remaining count associated with the flavor cartridge 180 has been decremented below a particular threshold value (e.g., a particular quantity of instances of vapor generation, a particular cumulative duration of vapor generations, and/or a particular amount of remaining time), and/or based on a determination of an absence of an electrical current between the electrically conductive instruments 152-1 and 152-2, via the conductive material of the flavor cartridge 180, the control circuitry 114 may selectively disable ("inhibit") vapor generation by the vapor generator 144. Enabling and disabling vapor generation by the vapor generator 144 may include enabling or disabling ("inhibiting") the supply of electrical power to the vapor generator 144, respectively, in response to one or more signals generated by the sensor 113.

In some example embodiments, the determined initial remaining count value is an initially-determined threshold value, and the value of the quantity of instances of vapor generation subsequent to the insertion of the flavor cartridge 180, the cumulative duration of vapor generations subsequent to the insertion of the flavor cartridge 180, and/or the duration of elapsed time subsequent to the insertion of the flavor cartridge 180 may be recorded, tracked, incremented, counted-up, or the like. Upon the recorded value being determined to at least reach the initially-determined threshold value, the control circuitry 114 may selectively disable ("inhibit") vapor generation by the vapor generator 144.

If and/or when the vapor generator 144 is "disabled" by the control circuitry 114, the control circuitry 114 may inhibit the supply of electrical power from the power supply 112 to the vapor generator 144, even in response to the receipt of a vaping command at the control circuitry, until the control circuitry 114 re-enables the vapor generator 144.

Accordingly, the generation of a generated vapor that may be converted into a flavored vapor may be selectively and/or adjustably controlled to ensure that the flavored vapor is generated according to a particular flavor cartridge 180 that is inserted into the vapor cartridge 140. Thus, the consistency and reliability of flavored vapor generation provided by the non-combustible vaping device 100 may be more reliably assured and controlled.

As referred to herein, a particular quantity of successively inserted flavor cartridges 180, a particular cumulative duration of vapor generation, and/or a particular duration of time ("period of elapsed time") associated with a vapor cartridge 140 may be referred to herein as a "remaining count" associated with the vapor cartridge 140. In some example embodiments, in response to the vapor cartridge 140 being detected as being coupled to base 110, the control circuitry 114 may selectively enable the supply of electrical power from power supply 112 to the vapor generator 144 and may further determine an initial "remaining count" associated with the vapor cartridge 140. The initial remaining count associated with the vapor cartridge 140 may be referred to as the maximum remaining count associated with the vapor cartridge 140. For example, in response to a vapor cartridge 140 initially being coupled to the base 110, a maximum quantity of successively inserted flavor cartridges 180 (e.g., 20 flavor cartridges 180 and/or a maximum duration of time ("period of elapsed time") associated with a vapor cartridge 140 may be determined.

Subsequently to the control circuitry 114 initially detecting the coupled vapor cartridge 140 and enabling the vapor generator 144, the control circuitry 114 may "decrement" (e.g., "count down") the remaining count associated with the coupled vapor cartridge 140 until the value of the remaining count is depleted and/or is decremented below the value of a particular threshold remaining count value associated with the remaining count of the vapor cartridge 140. The particular threshold remaining count value associated with the remaining count of the vapor cartridge 140 may be different from a particular threshold remaining count value associated with a remaining count of the flavor cartridge 180.

If and/or when the remaining count is a particular quantity of successively inserted flavor cartridges, the control circuitry 114 may decrement the quantity (e.g., reduce the quantity) in response to each successive detected insertion of a flavor cartridge 180 into the vapor cartridge 140.

If and/or when the remaining count is a cumulative duration of vapor generations implemented by the vapor cartridge 140, the control circuitry 114 may decrement the magnitude of the cumulative duration, in response to each successive implementation of an instance of vapor generation by the vapor cartridge 140, by an amount equal to the duration of time during which vapor is generated by the vapor cartridge during the given instance of vapor generation.

Based on a determination that the remaining count associated with the vapor cartridge 140 has been decremented below a particular threshold value, the control circuitry 114 may selectively disable ("inhibit") vapor generation by the vapor generator 144. The control circuitry 114 may inhibit vapor by the vapor generator 144 even if the vapor cartridge 140 is decoupled and later re-coupled. Restated, the control circuitry 114 may inhibit vapor generation support by the base 110 for the presently-coupled vapor cartridge 140, such that vapor generation support is re-enabled in response to the coupling of a new vapor cartridge 140 to the base 110 (e.g., the presently-coupled vapor cartridge 140 being swapped for a new vapor cartridge 140).

In some example embodiments, the determined initial remaining count value is an initially-determined threshold value, and the value of the quantity of insertions of flavor cartridges 180 subsequent to the coupling of the vapor cartridge 140, the cumulative duration of vapor generations subsequent to the coupling of the vapor cartridge 140 may be recorded, tracked, incremented, counted-up, or the like. Upon the recorded value being determined to at least reach the initially-determined threshold value, the control circuitry 114 may selectively disable ("inhibit") vapor generation by the vapor generator 144.

If and/or when the vapor generator 144 is "disabled" by the control circuitry 114, the control circuitry 114 may inhibit the supply of electrical power from the power supply 112 to the vapor generator 144, even in response to the receipt of a vaping command at the control circuitry, until the control circuitry 114 re-enables the vapor generator 144.

Accordingly, the generation of a generated vapor that may be converted into a flavored vapor may be selectively and/or adjustably controlled to ensure that the flavored vapor is generated according to a particular vapor cartridge 140 that is coupled to the base 110. Thus, the consistency and reliability of flavored vapor generation provided by the non-combustible vaping device 100 may be more reliably assured and controlled.

In some example embodiments, the control circuitry 114 may selectively disable ("inhibit") vapor generation by the vapor generator 144 in response to a determination that a device is coupled with one or more interfaces of the base 110. For example, if and/or when the base 110 includes a USB interface configured to send and/or receive data and/or electrical power from an external source, the control circuitry 114 may selectively disable vapor generation by the vapor generator 144 in response to a determination that a USB cable is inserted ("coupled") into the USB interface of the base 110. The control circuitry 114 may selectively enable vapor generation by the vapor generator 144 in response to a determination that the USB cable is decoupled from the USB interface of the base 110.

Referring to FIG. 1B, in some example embodiments, the vapor cartridge 140 may include a computing device 160 and interface 156-4, and the base 110 may include interface 116-4 and lead 115-4 that communicatively couples the interface 116-4 to the control circuitry 114.

The computing device 160, which may include a memory device and may include a processor device, may be configured to store information ("association information") associating particular electrical properties (e.g., current, voltage, some combination thereof, or the like) of an electrical current flowing between the electrically conductive instruments 152-1 and 152-2 through the flavor cartridge 180 with a particular set of one or more properties associated with the flavor cartridge 180. Such properties may be include a particular flavor cartridge "type" associated with the flavor cartridge 180, a particular one or more flavorants associated with the flavor cartridge 180, a particular initial "remaining count" associated with the flavor cartridge 180, some combination thereof, or the like.

Such association information may be used by the control circuitry 114 to adjustably control the supply of electrical power to the vapor generator 144 to adjustably control the generation of vapor according to the one or more properties associated with the flavor cartridge 180.

In some example embodiments, the computing device 160 may store association information in a database (e.g., a look-up table), where the association information includes an association between various electrical current properties and corresponding sets of flavor cartridge properties. In response to detecting an electrical current flowing between the electrically conductive instruments 152-1 and 152-2 (e.g., detecting a current in lead 154-1 as shown in FIG. 1B), the computing device 160 may determine one or more properties of the detected electrical current and may access the database to identify a set of flavor cartridge properties (e.g., a particular flavor cartridge "type") associated with the determined properties of the electrical current.

In some example embodiments, the computing device 160 may communicate the set of flavor cartridge properties (e.g., communicate the flavor cartridge "type") to the control circuitry 114 via interfaces 156-4 and 116-4 and lead 115-4, as the interfaces 156-4 and 116-4 may be communicatively coupled based on interfaces 160-1 and 160-2 being coupled together. The control circuitry 114 may process the received flavor cartridge property information and may identify and select a particular vapor generator control scheme associated with the flavor cartridge property information. Such a determination may be made by accessing a database (e.g., look-up table) that associates flavor cartridge property information (e.g., flavor cartridge "types") and corresponding vapor generator control schemes. The control circuitry 114 may then control the vapor generator 144 accordingly.

In some example embodiments, the computing device 160 may be configured to identify and select the one or more vapor generator control schemes based on processing the detected electrical current. The computing device 160 may then communicate the determined one or more vapor generator control schemes to the control circuitry 114, and the control circuitry 114 may control the supply of electrical power to the vapor generator 144 based on the received vapor generator control schemes.

In some example embodiments, the functionality of the computing device 160 is incorporated into the control circuitry 114, such that the computing device 160 and interfaces 116-4 and 156-4 and lead 115-4 are absent from the non-combustible vaping device 100. The control circuitry 114 may be configured to process a detected electrical current, determine one or more vapor generator control parameters based on the processing, and control the vapor generator 144 accordingly.

In some example embodiments, the control circuitry 114 is configured to determine whether an electrical current is detected in an electric circuit that includes the authentication assembly 150. Because the at least two electrically conductive instruments 152-1 to 152-2 of the authentication assembly 150 are spaced apart ("isolated from direct contact") by a gap space 190, the control circuitry 114 may determine, based on a detected presence of an electrical current through an electric circuit that includes the authentication assembly 150, that the at least two electrically conductive instruments 152-1 to 152-2 are electrically coupled ("electrically connected") together through a conductive material in the gap space 190, such that the gap space 190 is electrically bridged by the conductive material. Such a conductive material in the gap space 190 may be determined to be an electrically conductive material included in a flavor cartridge 180 inserted into the channel space 104 at least partially defined by the channel structure 142.

Accordingly, based on detecting an electrical current in the electric circuit that includes the authentication assembly 150, a determination ("initial detection") may be made that an authenticated flavor cartridge 180 (e.g., "appropriate" flavor cartridge) has been inserted into the channel space of the non-combustible vaping device.

In some example embodiments, the control circuitry 114 is configured to, in response to a determination that an electrical current is not present in the electric circuit, determine that an authenticated flavor cartridge 180 has not been inserted into the channel space 104. In response, the control circuitry 114 may deactivate ("disable") the vapor generator 144 and/or maintain the vapor generator 144 in a deactivated ("disabled") state, such that the non-combustible vaping device 100 is inhibited from generating a generated vapor.

As referred to herein, a detection of an electrical current in the electric circuit that includes the authentication assembly 150 may include detecting an electrical current having a magnitude that at least meets a particular threshold electrical current. As a result, the probability of false determinations at may be reduced.

In some example embodiments, the control circuitry 114 and/or the computing device 160 are configured to, alone or in combination and in response to a determination that the electrical current is detected in the electric circuit that includes the authentication assembly 150, determine a "type" associated with the authenticated flavor cartridge 180. In some example embodiments, the control circuitry 114 and/or the computing device 160 are configured to, alone or in combination, determine the "type" associated with the authenticated flavor cartridge 180. Such a determination may include processing the electrical current detected in the electric circuit and determining one or more properties associated with the detected electrical current.

In some example embodiments, a determination of a particular flavor cartridge type may be made based on a determination that a magnitude of the detected electrical current is within a particular range of electrical current values that is associated with a particular flavor cartridge type. In some example embodiments, a set of ranges of electrical current values and corresponding flavor cartridge types may be stored in a database, including a look-up table. Such a database may be stored in the control circuitry 114, the computing device 160, and/or a separate memory device that may be included in the non-combustible vaping device 100 and/or may be located externally to the non-combustible vaping device 100 (e.g., a computing device communicatively coupled to the non-combustible vaping device 100 via a wireless network connection).

In some example embodiments, the control circuitry 114 and/or the computing device 160 are configured to, alone or in combination and based on processing a detected electrical current to determine a value of the magnitude of the detected electrical current, access a database that may be stored at the control circuitry 114, computing device 160, and/or a separate memory device to determine which range of values, if any, includes the value of the detected electrical current. Based on identifying a particular range that includes a value of the detected electrical current, the database may be accessed to identify a particular flavor cartridge type that is associated with the identified particular range.

As referred to herein, a flavor cartridge type may include an indication of one or more particular properties associated with a flavor cartridge 180, including a particular flavor associated with the flavor cartridge 180, an amount of flavor material included in the flavor cartridge 180, a size and/or shape of flavor material in the flavor cartridge 180, a presence and/or configuration of multiple flavor materials in the flavor cartridge 180, a filter presence and/or size in the flavor cartridge 180, an indication of whether the flavor cartridge 180 includes a flavor matrix and/or an outlet-end insert, an initial remaining count associated with the flavor cartridge 180, some combination thereof, or the like.

In some example embodiments, the control circuitry 114 and/or the computing device 160 are configured to, alone or in combination and based upon determining a particular type associated with the authenticated flavor cartridge 180, to identify and select a particular vapor generator control scheme associated with the particular flavor cartridge type.

A control scheme associated with a particular flavor cartridge type may be included in the above-noted database in which the particular flavor cartridge type is associated with a particular value or range of values of one or more properties of a detected electrical current. Thus, based on identifying a particular flavor cartridge 180, a particular control scheme associated with the particular flavor cartridge type may be identified by accessing the database.

As referred to herein, a control scheme may include a set and/or sequence of control signals and/or control logic that may be used to control the supply of electrical power to a vapor generator 144 of the non-combustible vaping device 100 to cause one or more instances of generated vapor to be generated. The generation of an individual instance of generated vapor may be referred to herein as an "instance of vapor generation."

The control scheme may specify one or more various parameters associated with a set of vapor generation operations to be performed by the vapor generator 144 (e.g., instances of vapor generations to be implemented by the vapor generator 144) based on electrical power supplied according to the control circuitry 114. Such parameters may include a magnitude of generated vapor to be generated by the vapor generator 144 in response to each vaping command, a magnitude of a duration of elapsed time during which the vapor generator 144 is to generate vapor, a remaining count associated with the inserted flavor cartridge 180, some combination thereof, or the like. The period of elapsed time may extend from the time at which the electrical current is detected and/or the time at which the vapor generator 144 is first controlled to generate a generated vapor after the electrical current is detected.

A control scheme may include an expiration condition that indicates one or more parameters according to which the vapor generator 144 is to be subsequently deactivated ("disabled") by the control circuitry 114 after being activated and controlled to generate vapor according to the control scheme. An expiration condition may include a threshold value of the remaining count associated with the flavor cartridge 180 and/or a threshold value of the remaining count associated with the vapor cartridge 140. The threshold value of the remaining count associated with the flavor cartridge 180 may be a threshold magnitude of a remaining period of elapsed time, a particular quantity of instances of vapor generation that may be permitted to occur subsequent to the initial detection of the inserted flavor cartridge 180, some combination thereof, or the like. A threshold value of the remaining count associated with the vapor cartridge may include a threshold quantity of successive insertions of flavor cartridges into the vapor cartridge, a threshold remaining cumulative duration of vapor generations implemented by the vapor cartridge, some combination thereof, or the like. Upon determining that a value of the remaining count (e.g., remaining time and/or quantity of instances of vapor generation) is less than the threshold value, an expiration condition of the control scheme may be determined to be reached. The vapor generator 144 may be deactivated ("disabled") by the control circuitry 114 upon determination that the expiration condition has been reached.

In some example embodiments, the control circuitry 114 may determine whether an expiration condition is reached based at least in part upon a determination of whether a previously-inserted flavor cartridge 180 is subsequently removed from the vapor cartridge 140 for at least a threshold period of elapsed time. Such a threshold period of elapsed time may be, for example, a period of six seconds. For example, the control circuitry 114 may, in response to a determination that the flavor cartridge 180 has been removed and subsequently re-inserted into the vapor cartridge 140 within a period of less than six seconds, decline to determine that an expiration condition is reached and may continue to decrement the remaining count associated with the flavor cartridge 180 as if the flavor cartridge 180 had not been removed. In another example, the control circuitry 114 may, in response to a determination that the flavor cartridge 180 has been removed from the vapor cartridge 140 for at least six seconds, determine that an expiration condition is reached.

A vaping command may include a signal received at the control circuitry 114 based on adult vaper interaction with an interface of the non-combustible vaping device 100, based on sensor data received from one or more sensors 113 in the non-combustible vaping device 100, some combination thereof, or the like.

In some example embodiments the control circuitry 114 may control the vapor generator 144 according to a base (e.g., "default") control scheme that is selected based on the detection of the electrical current in the electric circuit.

In some example embodiments, the control circuitry 114 may activate ("enable") the vapor generator 144 and control the vapor generator 144 according to the selected control scheme. Such control may include the control circuitry 114 controlling the supply of electrical power from the power supply 112 to the vapor generator 144, to cause the vapor generator 144 to generate a particular amount of generated vapor over a particular magnitude of a duration ("implement an instance of vapor generation"), based on a determination that vapor is to be generated. Such a determination may be made based on a determination that a vaping command is received from an interface of the non-combustible vaping device 100 based on adult vaper interaction therewith, a determination that sensor data received from a sensor 113 of the non-combustible vaping device 100 includes data values (e.g., airflow magnitude, pressure change magnitude, or the like) that at least meet one or more threshold data values, some combination thereof or the like.

In some example embodiments, the control circuitry 114 is configured to cause a supply of electrical power to be supplied from the power supply 112 to the vapor generator 144 for at least a threshold period of elapsed time. In some example embodiments, sensor data ("sensor signals") may be received from sensor 113 at the control circuitry 114 over a period of time that is less than the threshold period of elapsed time during which electrical power is supplied from the power supply 112 to the vapor generator 144. For example, in response to receiving a sensor signal corresponding to at least a threshold data value from the sensor 113, the control circuitry 114 may cause electrical power to be supplied from the power supply 112 to the vapor generator 144 for at least a threshold period of elapsed time, even though the sensor signal corresponding to at least the threshold data value may cease to be received at the control circuitry 114 before the threshold period of elapsed time is completed. As a result, the control circuitry 114 may continue to cause electrical power to be supplied to the vapor generator 144 for a period of time subsequent to the control circuitry 114 ceasing to receive sensor signals corresponding to at least the threshold data value.

Controlling a vapor generator 144 according to a selected control scheme may include maintaining the vapor generator 144 in an "active state," wherein the vapor generator 144 may be controlled to generate vapor, until one or more expiration conditions associated with the selected control scheme are determined to be reached (e.g., are determined to have occurred).

In some example embodiments, the control circuitry 114 is configured to, based on a determination that an expiration condition associated with the selected control scheme is reached, deactivate ("disable") the vapor generator 144 to inhibit vapor generation by the vapor generator 144.

In view of at least the above, the generation of the generated vapor may be selectively and/or adjustably controlled based on whether an authenticated flavor cartridge 180 (e.g., a flavor cartridge 180 including the instance of electrically conductive material) is inserted into the vapor cartridge 140. Accordingly, the generation of a generated vapor that may be converted into a flavored vapor may be controlled to ensure that the flavored vapor is generated according to an authenticated flavor cartridge 180. Thus, the consistency and reliability of flavored vapor generation may be more reliably assured and controlled.

In further view of at least the above, the generation of the generated vapor may be selectively and/or adjustably controlled according to particular flavor cartridge "types" of authenticated flavor cartridges 180 (e.g., flavor cartridges 180 including different types of electrically conductive material that result in electrical currents having different properties) that may be inserted into the vapor cartridge 140. Accordingly, the generation of a generated vapor that may be converted into a flavored vapor may be selectively and/or adjustably controlled to ensure that the flavored vapor is generated according to a particular "flavor cartridge type" of the flavor cartridge 180 that is inserted into the vapor cartridge 140. Thus, the consistency and reliability of flavored vapor generation across a range of types of appropriate flavor cartridges 180 may be more reliably assured and controlled.

As described further below, the base 110 may include one or more interfaces via which the control circuitry 114 may be configured to display information associated with one or more portions of the non-combustible vaping device 100. For example, the base 110 may include a display interface device (e.g., a graphical user interface or "GUI") via which the control circuitry 114 may present a graphical indication of 1) whether the vapor cartridge 140 is coupled to the base 110, 2) whether a flavor cartridge 180 is inserted into the vapor cartridge 140, 3) whether a flavor cartridge 180 that is inserted into the vapor cartridge 140 is "authenticated," such that vapor generation by the vapor cartridge 140 is enabled, 4) an amount of electrical power stored in the power supply 112, 5) an amount of pre-vapor formulation held in the vapor cartridge 140, and/or 6) a magnitude of the remaining count associated with a presently-inserted flavor cartridge 180.

As also described further below, in some example embodiments, the base 110 may include an interface (e.g., a tactile interface, a display interface, an audio interface, some combination thereof, or the like) via which an adult vaper may interact with the base 110 to control one or more functional aspects of the non-combustible vaping device 100.

For example, in some example embodiments, the control circuitry 114 may be configured to control the supply of electrical power to the vapor generator 144 of the vapor cartridge 140, to cause an instance of vapor generation to occur, based on receiving a control signal from an interface of the base 110, where the control signal is generated at the interface based on adult vaper interaction with the interface.

In another example, the control circuitry 114 may be configured to control the instances of information that are presented ("displayed") on a display interface of the base 110 based on adult vaper interaction with a tactile interface of the base 110. The control circuitry 114 may switch between different displays of information (referred to herein as "graphical displays") based on successive interactions between an adult vaper and the tactile interface of the base 110, e.g., switching in a continuous loop ("cycling") between a power graphical display ("PGD"), a vapor cartridge graphical display ("VCGD"), a flavor cartridge graphical display ("FCGD"), some combination thereof, or the like in a particular sequence.

Figures 1C, 1D, 1E:
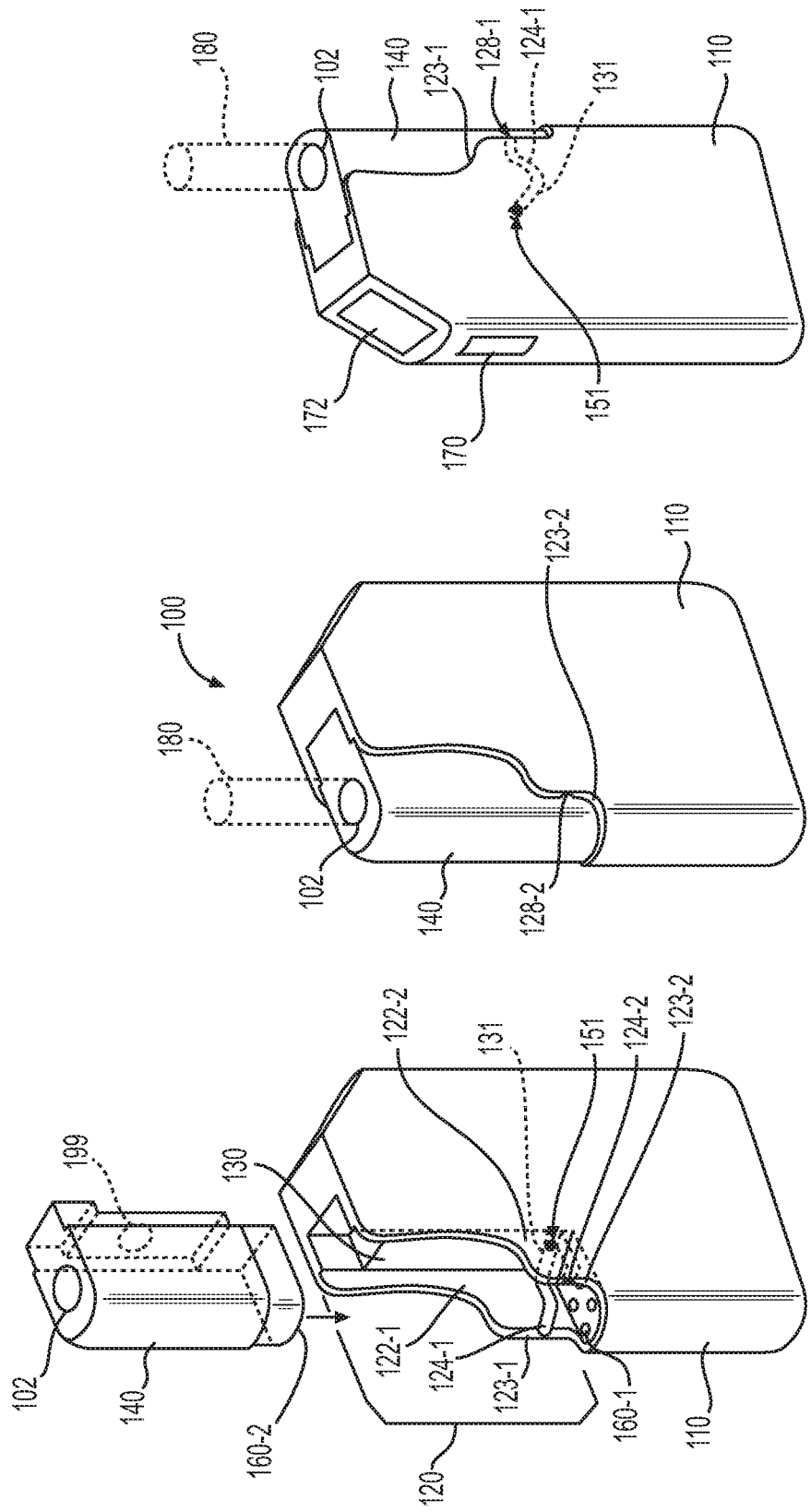
FIG. 1C is a perspective view of a decoupled vapor cartridge and base that may be coupled to form a non-combustible vaping device, according to some example embodiments.
FIG. 1D and FIG. 1E are each a perspective view of a non-combustible vaping device formed from the coupling of the vapor cartridge and base shown in FIG. 1C.

FIG. 1C is a perspective view of a decoupled vapor cartridge and base that may be coupled to form a non-combustible vaping device, according to some example embodiments. FIG. 1D and FIG. 1E are each a perspective view of a non-combustible vaping device formed from the coupling of the vapor cartridge and base shown in FIG. 1C.

As shown via the use of common reference labels between FIGS. 1A-1B and FIGS. 1C-1E, the vapor cartridge 140 and base 110 shown in FIGS. 1C-1E may include some or all of the elements of the vapor cartridge 140 and base 110 shown in FIGS. 1A-1B, respectively. Similarly, the vapor cartridge 140 and base 110 shown in FIGS. 1A-1B may include some or all of the elements of the vapor cartridge 140 and base 110 shown in FIGS. 1C-1E, respectively.

In some example embodiments, including the example embodiments shown in FIGS. 1C-1E, the base 110 of a non-combustible vaping device 100 may include a set of structural elements that collectively define a cavity 120 into which a vapor cartridge 140 may be received to be coupled with the base 110. The structural elements may be configured to conform to the housing elements of the vapor cartridge 140 to cause the vapor cartridge 140 to be particularly aligned in relation to the base 110, such that the interface 160-2 of the vapor cartridge 140 is successfully connected to the interface 160-1 of the base 110. As described above, each interface of the interface 160-1 and the interface 160-2 may include one or more electrical connectors that is a pogo pin connector.

As shown in FIGS. 1C-1E, the base 110 includes a set of guide walls 122-1, 122-2, and 130 that at least partially define sidewalls of the cavity 120. As further shown in FIGS. 1C-1D, and as further described below with reference to FIGS. 6A-6D, each guide wall 122-1 and 122-2 may include a channel 124-1 and 124-2 that extends along a surface of the respective guide wall, from separate, respective outer edges 123-1 and 123-2 of the guide walls 122-1 and 122-2, to separate ends of a channel 131 extending along the guide wall 130 of the base 110. The channel 131 may extend over the aforementioned air inlet port 151. As a result, the channels 124-1, 124-2, and 131 may collectively define a set of channels that extend from the air inlet port 151 to separate outlets 128-1 and 128-2 at separate outer edges 123-1 and 123-2 of the guide walls 122-1 and 122-2.

As shown in FIG. 1D and FIG. 1E, if and/or when the vapor cartridge 140 is coupled to the base 110, the guide walls 122-1, 122-2 and 130 may at least partially align and enclose one or more portions of the vapor cartridge 140 housing (e.g., housing 141 as shown in FIGS. 1A-1B), such that the vapor cartridge 140 housing encloses the channels 124-1, 124-2, and 131, with the exception of the outlets 128-1 and 128-2 of the channels 124-1 and 124-2 at the separate, respective outer edges 123-1 and 123-2 of the guide walls 122-1 and 122-2. As a result, and as shown in FIG. 1D and FIG. 1E, the vapor cartridge 140 and base 110 collectively establish one or more conduits that extend, from the outer edges 123-1 and 123-2 of the guide walls 122-1 and 122-2 to the air inlet port 151, where the air inlet port 151 is in fluid communication with the aforementioned sensor 113 of the base 110.

In some example embodiments, and as shown in the example embodiments illustrated in FIG. 1E, the base 110 may include one or more interfaces 170 and 172 via which information and/or commands may be communicated between the base 110 and an adult vaper. For example, as shown in FIG. 1E, the base 110 may include a tactile interface 170 (e.g., a button interface) and a display interface 172. The display interface 172 may include a light emitting diode (LED) display that is configured to present one or more graphical displays (GUIs) that provide one or more instances of information associated with the non-combustible vaping device 100. The base 110 may be configured to adjust and/or change the display on the interface 172 based on adult vaper interaction with the tactile interface 170. For example, as described further below, the base 110 may be configured to cycle through a sequence of graphical displays, each graphical display presenting a different set of information associated with the non-combustible vaping device 100, based on successive interactions with (e.g., "clicks" of) the tactile interface 170.

Still referring to FIGS. 1C-1E and further referring back to FIGS. 1A-1B, the vapor cartridge 140 may, in some example embodiments, include a reservoir refill port 199 that is in fluid communication with the pre-vapor formulation reservoir 146 and enables pre-vapor formulation to be supplied to the pre-vapor formulation reservoir 146 via the port 199, thereby enabling the pre-vapor formulation reservoir 146 to be re-filled upon depletion with a similar or different pre-vapor formulation in relation to the pre-vapor formulation that has been depleted from the pre-vapor formulation reservoir 146. As further shown in FIG. 1C, the vapor cartridge 140 may include the reservoir refill port 199 on a portion of the outer housing 141 that is configured to be enclosed (e.g., encompassed, obscured, isolated from exposure, some combination thereof, or the like) based on the vapor cartridge 140 being coupled to the base 110, such that the reservoir refill port 199 is obscured if and/or when the vapor cartridge 140 is coupled to the base 110. However, it will be understood that the reservoir refill port 199 may be on any portion of the outer housing 141, including one or more portions of the outer housing 141 that are configured to be exposed based on the vapor cartridge 140 being coupled to the base 110. In some example embodiments, the reservoir refill port 199 may be absent from the vapor cartridge 140, such that the vapor cartridge 140 includes a non-refillable pre-vapor formulation reservoir 146.

The pre-vapor formulation, as described herein, is a material or combination of materials that may be transformed into a vapor. For example, the pre-vapor formulation may be a liquid, solid and/or gel formulation including, but not limited to, water, beads, solvents, active ingredients, ethanol, plant extracts, natural or artificial flavors, and/or vapor formers such as glycerin and propylene glycol. The pre-vapor formulation may include those described in U.S. Patent Application Publication No. 2015/0020823 to Lipowicz et al. filed Jul. 16, 2014 and U.S. Patent Application Publication No. 2015/0313275 to Anderson et al. filed Jan. 21, 2015, the entire contents of each of which is incorporated herein by reference thereto.

In some example embodiments, the pre-vapor formulation is one or more of propylene glycol, glycerin and combinations thereof.

The pre-vapor formulation may include nicotine or may exclude nicotine. The pre-vapor formulation may include one or more tobacco flavors. The pre-vapor formulation may include one or more flavors that are separate from one or more tobacco flavors.

In some example embodiments, a pre-vapor formulation that includes nicotine may also include one or more acids. The one or more acids may be one or more of pyruvic acid, formic acid, oxalic acid, glycolic acid, acetic acid, isovaleric acid, valeric acid, propionic acid, octanoic acid, lactic acid, levulinic acid, sorbic acid, malic acid, tartaric acid, succinic acid, citric acid, benzoic acid, oleic acid, aconitic acid, butyric acid, cinnamic acid, decanoic acid, 3,7-dimethyl-6-octenoic acid, 1-glutamic acid, heptanoic acid, hexanoic acid, 3-hexenoic acid, trans-2-hexenoic acid, isobutyric acid, lauric acid, 2-methylbutyric acid, 2-methylvaleric acid, myristic acid, nonanoic acid, palmitic acid, 4-penenoic acid, phenylacetic acid, 3-phenylpropionic acid, hydrochloric acid, phosphoric acid, sulfuric acid and combinations thereof.

The pre-vapor formulation reservoir 146, in some example embodiments, may include a storage medium that may hold the pre-vapor formulation. The storage medium may be a fibrous material including at least one of cotton, polyethylene, polyester, rayon and combinations thereof. The fibers may have a diameter ranging in size from about 6 microns to about 15 microns (e.g., about 8 microns to about 12 microns or about 9 microns to about 11 microns). The storage medium may be a sintered, porous or foamed material. Also, the fibers may be sized to be irrespirable and may have a cross-section that has a Y-shape, cross shape, clover shape or any other suitable shape. In some example embodiments, the pre-vapor formulation reservoir 146 may include a filled tank lacking any storage medium and containing only pre-vapor formulation.

The pre-vapor formulation reservoir 146 may be sized and configured to hold enough pre-vapor formulation such that the vapor cartridge 140 may be configured for vaping for at least about 200 seconds. The non-combustible vaping device 100 may be configured to allow each vaping to last a maximum of about 5 seconds.

The vapor generator 144 may include a dispensing interface that enables pre-vapor formulation to be communicated from the pre-vapor formulation reservoir 146 to the heating element 148. The dispensing interface may include a wick. The dispensing interface may include filaments (or threads) having a capacity to draw the pre-vapor formulation. For example, a dispensing interface may be a wick that is a bundle of glass (or ceramic) filaments, a bundle including a group of windings of glass filaments, some combination thereof, or the like, all of which arrangements may be capable of drawing pre-vapor formulation via capillary action by interstitial spacings between the filaments. In some example embodiments, the dispensing interface may include one to eight filament strands, each strand comprising a plurality of glass filaments twisted together. The end portions of the dispensing interface may be flexible and foldable into the confines of the pre-vapor formulation reservoir 146. The filaments may have a cross-section that is generally cross-shaped, clover-shaped, Y-shaped, or in any other suitable shape.

The dispensing interface may include any suitable material or combination of materials, also referred to herein as wicking materials. Examples of suitable materials may be, but not limited to, glass, ceramic- or graphite-based materials. The dispensing interface may have any suitable capillary drawing action to accommodate pre-vapor formulations having different physical properties such as density, viscosity, surface tension and vapor pressure.

In some example embodiments, the heating element 148 may include a wire coil. The wire coil may at least partially surround the dispensing interface. The wire may be a metal wire and/or the wire coil may extend fully or partially along the length of the dispensing interface. The wire coil may further extend fully or partially around the circumference of the dispensing interface. In some example embodiments, the wire coil may be isolated from direct contact with the dispensing interface.

The heating element 148 may be formed of any suitable electrically resistive materials. Examples of suitable electrically resistive materials may include, but not limited to, titanium, zirconium, tantalum and metals from the platinum group. Examples of suitable metal alloys include, but not limited to, stainless steel, nickel, cobalt, chromium, aluminum-titanium-zirconium, hafnium, niobium, molybdenum, tantalum, tungsten, tin, gallium, manganese and iron-containing alloys, and super-alloys based on nickel, iron, cobalt, stainless steel. For example, the heating element 34 may be formed of nickel aluminide, a material with a layer of alumina on the surface, iron aluminide and other composite materials, the electrically resistive material may optionally be embedded in, encapsulated or coated with an insulating material or vice-versa, depending on the kinetics of energy transfer and the external physicochemical properties required. The heating element 148 may include at least one material selected from the group consisting of stainless steel, copper, copper alloys, nickel-chromium alloys, super alloys and combinations thereof. In some example embodiments, the heating element 148 may be formed of nickel-chromium alloys or iron-chromium alloys. In some example embodiments, the heating element 148 may be a ceramic heater having an electrically resistive layer on an outside surface thereof.

The heating element 148 may heat a pre-vapor formulation in the dispensing interface by thermal conduction. Alternatively, heat from the heating element 148 may be conducted to the pre-vapor formulation by means of a heat conductive element or the heating element 148 may transfer heat to the incoming ambient air that is drawn through the vapor cartridge 140 during vaping, which in turn heats the pre-vapor formulation by convection.

It should be appreciated that, instead of using a dispensing interface, the vapor generator 144 may include a heating element 148 that is a porous material which incorporates a resistance heater formed of a material having a high electrical resistance capable of generating heat quickly.

In some example embodiments, one or more portions of the vapor cartridge 140 may be replaceable. Such one or more portions may include one or more of the vapor cartridge 140 and the flavor cartridge 180. In other words, once one of the flavorant of the flavor cartridge 180 or the pre-vapor formulation of the pre-vapor formulation reservoir 146 is depleted, only the flavor cartridge 180 or the vapor cartridge 140 may be replaced, respectively. In some example embodiments, the entire non-combustible vaping device 100 may be disposed once one of the pre-vapor formulation reservoir 146 or the flavor cartridge 180 is depleted.

Flavor Cartridge

FIG. 2A, FIG. 2B, FIG. 2C, and FIG. 2D are each a cross-sectional view of a flavor cartridge according to some example embodiments.

Figure 2C:
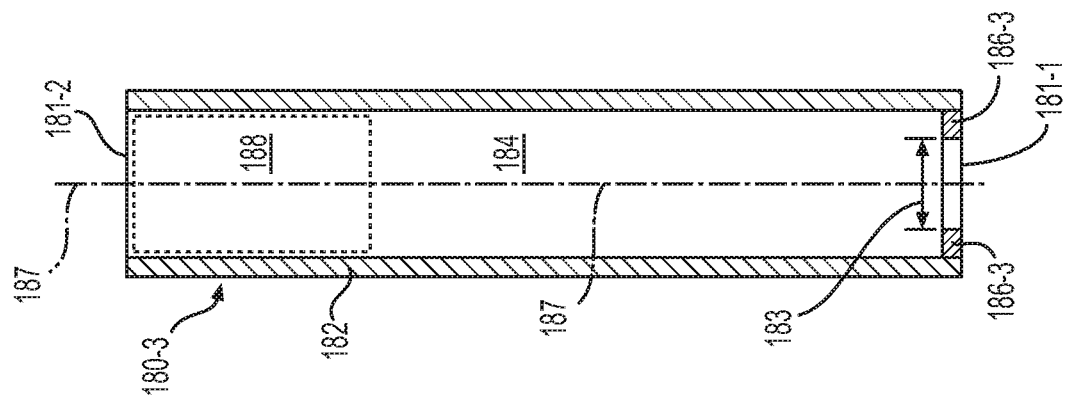
FIG. 2A, FIG. 2B, FIG. 2C, and FIG. 2D are each a cross-sectional view of a flavor cartridge according to some example embodiments.
Figure 2B:
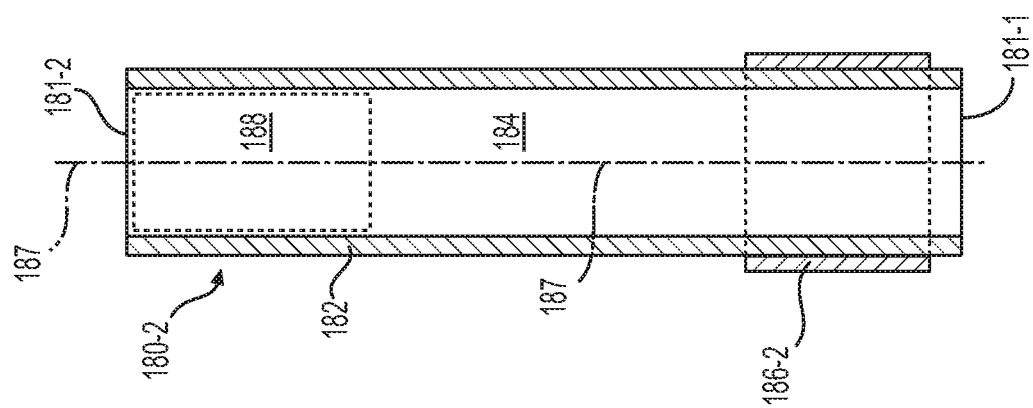
Figure 2A:
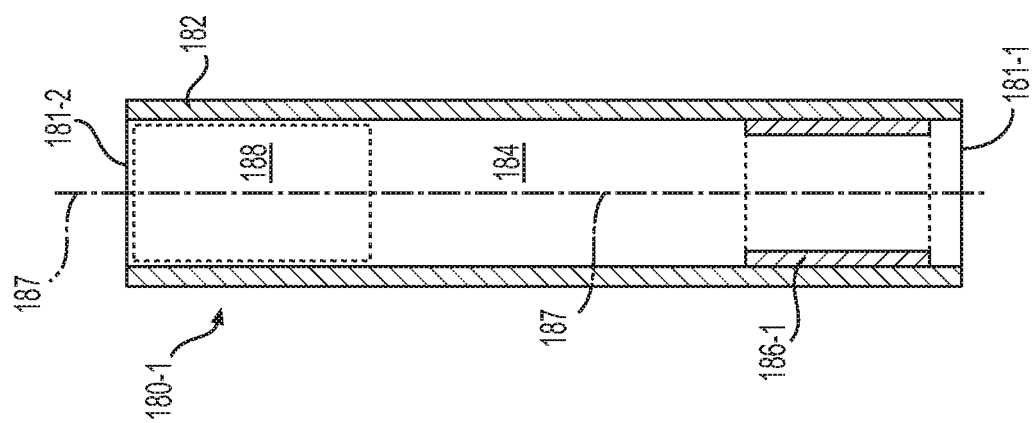

The flavor cartridges 180-1 to 180-3 illustrated in FIGS. 2A-2C may be included in any of the embodiments of flavor cartridges included herein, including the flavor cartridge 180 illustrated in FIGS. 1A-1B.

Referring to FIGS. 2A-2C, the flavor cartridges 180-1 to 180-3 each include a tip-end opening 181-1 and an outlet-end opening 181-2. The flavor cartridges 180-1 to 180-3 are each configured to receive a vapor, including a generated vapor, through the tip-end opening 181-1 and into an interior of the flavor cartridges 180-1 to 180-3. The flavor cartridges 180-1 to 180-3 are each further configured to direct a vapor, including a flavored vapor formed through flavorant elution into the generated vapor, out of the respective flavor cartridge via the outlet end opening 181-2.

Still referring to FIGS. 2A-2C, the flavor cartridges 180-1 to 180-3 each may include a flavor material 184 holding a flavorant and a containment structure 182 at least partially enclosing the flavor material 184 within the interior of the respective flavor cartridge. As shown in FIGS. 2A-2C, the containment structure 182 may extend coaxially with a longitudinal axis of the flavor material 184. The containment structure 182 may enclose side portions of the flavor cartridge 180 to define openings 181-1, 181-2 at opposite ends of the flavor cartridge 180. The containment structure 182 is also referred to herein as an outer housing of the flavor cartridge 180, an "outer shell" of the flavor cartridge 180, some combination thereof, or the like. In some example embodiments, the containment structure 182 may be referred to as an outer surface area of the flavor material 184.

The flavor material 184 may be a porous structure in which one or more flavorants are included. In some example embodiments, the flavor material 184 is a collection of flavor materials. In some example embodiments, the flavor material 184 includes one or more botanical materials. In some example embodiments, the flavor material 184 includes one or more types of tobacco. In some example embodiments, a flavor cartridge 180 includes one or more types of tobacco as the flavor material 184. A flavor material 184 that includes tobacco may be referred to herein as a tobacco flavor material.

In some example embodiments, a flavor cartridge 180 that includes a flavor material 184 that includes tobacco may be referred to as a tobacco element. In some example embodiments, the flavor cartridge 180 is a tobacco rod that holds a flavor material 184 that is one or more types of tobacco (also referred to as a tobacco flavor material 184). The tobacco rod may be configured to be at least partially combusted such that at least a portion of the flavor material 184 is combusted and directed out of an end of the tobacco rod. A tobacco element may include one or more of a cigarette, cigar, cigarillo, some combination thereof, or the like.

In some example embodiments, including the example embodiments shown in FIG. 2A-2C, the flavor cartridges 180-1 to 180-3 each may include a filter element 188. The filter element 188 may be configured to filter one or more instances of particular matter from a vapor. In some example embodiments, a flavor cartridge 180 that includes a flavor material 184 that is a tobacco rod may include a filter element 188 that is configured to filter one or more instances of particular matter from a vapor that includes one or more products of combustion of at least the tobacco flavor material included in the flavor material 184.

The filter element 188 may, in some example embodiments, include a hollow acetate tube (HAT) filter. The filter element 188 may be configured to provide reduced filtration efficiency, relative to filter elements included in some example embodiments, such that a loss of vapor to the filter element 188 is reduced, relative to vapor loss to filter elements in some example embodiments. The containment structure 182 may enclose side portions of the filter element 188 to direct vapor exiting the flavor material 184 to pass through the filter element 188 to outlet-end opening 181-2.

In some example embodiments, the containment structure 182 includes an instance of tipping paper. The containment structure 182, as shown in the example embodiments of FIG. 2A-2C, may overlap an outer surface area of the filter element 188 and an outer surface area of the flavor material 184.

Referring to FIGS. 2A-2C, the flavor cartridges 180-1 to 180-3 each may include multiple separate instances of flavor materials 184 that each hold a different flavorant. For example, the flavor material 184 may include a tobacco flavor material and a separate non-tobacco flavor material, where the separate instances of flavor material are stacked sequentially along the longitudinal axis 187.

Still referring to FIGS. 2A-2C, the flavor cartridges 180-1 to 180-3 each may be a tobacco rod (e.g., a cigarette, cigar, cigarillo, some combination thereof, or the like) that may be inserted into the channel space of the non-combustible vaping device 100 shown in FIG. 1. In some example embodiments, at least the vapor cartridge 140 is configured to provide a flavored vapor based on generating and directing a generated vapor through the flavor cartridge 180 such that the generated vapor elutes flavorant from the flavor material 184 included in the flavor cartridge 180 to form the flavored vapor independently of and/or without any combustion of the flavor material 184. The vapor cartridge 140 may thus be configured to form a flavored vapor based on flavorant elution from flavor material 184 included in the flavor cartridge 180 without combustion of the flavor material 184.

Still referring to FIGS. 2A-2C, in some example embodiments, the flavor cartridges 180-1 to 180-3 may each include an instance of electrically conductive material that extends at least partially around the flavor material 184. As described herein, an instance of electrically conductive material may include one or more electrically conductive materials. For example, as described herein, an instance of electrically conductive material in a flavor cartridge 180 may include aluminum. In another example, as described herein, an instance of electrically conductive material in a flavor cartridge 180 may include a conductive ink material.

In FIGS. 2A-2C, the instances of electrically conductive material 186-1 to 186-3 are each illustrated as a "band" of electrically conductive material that extends at least partially around the flavor material 184, but it will be understood that the example embodiments are not limited thereto. For example, in the example embodiments shown in FIG. 2A, a flavor cartridge 180-1 may include an instance of electrically conductive material 186-1 that is a "patch" structure and is between a portion of the flavor material 184 and a portion of the containment structure 182. As noted above, the containment structure 182 may be referred to herein as an "outer shell." The instance of electrically conductive material 186-1 to 186-3 may, in some example embodiments, be a continuous band of electrically conductive material that extends around an entirety of the flavor material 184. In some example embodiments, the instance of electrically conductive material 186-1 to 186-3 may extend around a limited portion of the flavor material 184, including a limited portion of the circumference of the flavor material 184.

As shown in FIGS. 2A-2B, in some example embodiments, the instance of electrically conductive material may extend coaxially with the longitudinal axis of the flavor cartridges 180-1 and 180-2. For example, as shown in FIGS. 2A-2B, the instance of electrically conductive material 186-1 to 186-2 may be an element extending coaxially with the respective longitudinal axes 187 of the flavor cartridges 180-1 and 180-2. Such an element may be a partially cylindrical element and/or a full cylindrical element that extends coaxially with the longitudinal axes of the flavor cartridges 180-1 and 180-2.

In some example embodiments, an instance of electrically conductive material extends along a limited portion of the longitudinal axis 187 of the flavor cartridge 180. For example, as shown in FIGS. 2A-2B, the instances of electrically conductive material 186-1 to 186-2 may extend, coaxially with longitudinal axis 187, along a limited portion of the tip-end proximate portion of the flavor cartridges 180-1 and 180-2. In some example embodiments, an instance of electrically conductive material may extend along an entirety of the longitudinal axes 187 of the flavor cartridges 180-1 and 180-2, between the tip-end opening 181-1 and the outlet-end opening 181-2.

Referring to FIG. 2A, a flavor cartridge 180-1 may include an instance of electrically conductive material 186-1 that is between the flavor material 184 and the containment structure 182. As shown in FIG. 2A, the instance of electrically conductive material 186-1 extends along at least a portion of the outer surface area of the flavor material 184 and is further between the outer surface area of the flavor material 184 and the inner surface area of the containment structure 182. As a result, the containment structure 182 isolates the instance of electrically conductive material 186-1 from being directly exposed to an external (e.g., "ambient") environment.

In some example embodiments, an instance of electrically conductive material is configured to establish an electrical connection between (e.g., "electrically connect") at least two separate electrically conductive instruments, based on the at least two separate electrically conductive instruments independently and directly contacting the instance of electrically conductive material.

Because the containment structure 182 isolates the instance of electrically conductive material 186-1 from direct exposure to the external environment, the flavor cartridge 180-1 shown in FIG. 2A is configured to enable the electrical connection between the at least two separate electrically conductive instruments, based on each separate electrically conductive instrument at least partially impinging into an interior of the flavor cartridge 180-1 to directly contact the instance of electrically conductive material 186-1.

For example, the flavor cartridge 180-1 may be configured to enable the electrical connection between at least two separate electrically conductive instruments that include separate, respective electrically conductive blades configured to cut into ("pierce") at least a portion of the flavor cartridge 180-1 to directly contact the instance of electrically conductive material of the instance of electrically conductive material 186-1.

The containment structure 182 may be a material (e.g., paper, plastic, some combination thereof, or the like) that is configured to be cut and/or pierced by an electrically conductive instrument, such that at least a portion of the electrically conductive instrument may extend through at least a portion of the containment structure 182 to directly contact the instance of electrically conductive material 186-1. In addition, the instance of electrically conductive material 186-1 and/or the flavor material 184 may be configured to be cut and/or pierced, such that at least a portion of the electrically conductive instrument may extend through at least a portion of the instance of electrically conductive material 186-1 and/or the flavor material 184.

In some example embodiments, if and/or when the flavor cartridge 180-1 of FIG. 2A is inserted into a channel space into which at least two electrically conductive instruments extend, the electrically conductive instruments may pierce and/or cut through at least the containment structure 182 as the flavor cartridge 180-1 is inserted, tip end 182-1 first, through the channel space. As the electrically conductive instruments extend through the containment structure 182 and directly contact the instance of electrically conductive material 186-1 at two separate locations of the instance of electrically conductive material 186-1, the instance of electrically conductive material 186 may establish an electrical connection between the at least two electrically conductive instruments, such that an electrical current may pass between the electrically conductive instruments through the instance of electrically conductive material 186.

As the flavor cartridge 180-1 is extended further through the channel space, the electrically conductive instruments, initially directly contacting the instance of electrically conductive material 186-1 at a tip end of the instance of electrically conductive material 186-1, may move, relative to the instance of electrically conductive material 186-1, through an outlet end of the instance of electrically conductive material 186-1, such that the electrically conductive instruments pass out of direct contact with the instance of electrically conductive material 186-1.

In some example embodiments, if and/or when the instance of electrically conductive material 186-1 is configured to be pierced and/or cut by the electrically conductive instruments, the instance of electrically conductive material 186-1 may be configured to be severed ("cut") into multiple, separate pieces by the electrically conductive instruments, based on the flavor cartridge 180-1 being inserted through a channel space into which the electrically conductive instruments extend.

As a result, based on the instance of electrically conductive material 186-1 being severed, the instance of electrically conductive material 186-1 may be restricted from establishing an electrical connection between the electrically conductive instruments if and/or when the flavor cartridge 180-1 subsequently moves through the channel space again (e.g., is removed from the channel space and/or is re-inserted into the channel space subsequently from being initially inserted sufficiently through the channel space to enable the electrically conductive instruments to sever the instance of electrically conductive material 186-1 of electrically conductive material).

Referring to FIG. 2B, a flavor cartridge 180-2 may include an instance of electrically conductive material 186-2 that is on an outer surface area of the containment structure 182. As shown in FIG. 2B, the instance of electrically conductive material 186-2 may be a band of electrically conductive material that extends along at least a portion of the outer surface area of the containment structure 182.

In some example embodiments, the flavor cartridge 180-2 is configured to enable the instance of electrically conductive material 186-2 to electrically connect at least two separate electrically conductive instruments, based on direct contact between the separate electrically conductive instruments and the instance of electrically conductive material, on an outer surface (e.g., "outer surface area") of the containment structure 182. As a result, the flavor cartridge 180-2 is configured to electrically connect the electrically conductive instruments across an exterior of the containment structure, such that the electrical connection is isolated from extending through an interior of the flavor cartridge 180-2, and without at least the containment structure 182 being pierced and/or cut by the electrically conductive instruments. The instance of electrically conductive material 186-2 may be configured to be pierced and/or cut by an electrically conductive instrument, as described above with reference to the instance of electrically conductive material 186-1 in FIG. 2A. The containment structure 182 may be configured to resist being pierced and/or cut by an electrically conductive instrument.

Referring to FIG. 2C, a flavor cartridge 180-3 may include an instance of electrically conductive material 186-3 that is at a tip end of the flavor cartridge 180-3. The instance of electrically conductive material may include a disc. Such a disc may be a cylindrical disc that includes at least one gap space 183. Such an instance of electrically conductive material 186-3 may be configured to directly contact at least two electrically conductive instruments and establish an electrical connection therebetween via the instance of electrically conductive material 186.

As shown in FIG. 2C, the instance of electrically conductive material 186-3 may be a cylindrical disc that extends, orthogonally to the longitudinal axis 187 of the flavor cartridge 180-3, over the tip end surface of the flavor material 184 at the tip end of the flavor cartridge 180-3. The instance of electrically conductive material 186-3 shown in FIG. 2C includes ("defines") a gap space 183 that exposes the interior of the flavor cartridge 180-3 through a tip end of the flavor material 184. The flavor cartridge 180-3 shown in FIG. 2C is configured to receive generated vapor into the interior of the flavor cartridge 180-3 through the gap space 183 of the instance of electrically conductive material 186-3.

In the example embodiments shown in FIG. 2C, the instance of electrically conductive material 186-3 defines a gap space 183 that is centered on the longitudinal axis 187. In some example embodiments, the instance of electrically conductive material 186-3 defines one or more gap spaces ("gaps") that are not centered on the longitudinal axis 187. In some example embodiments, the instance of electrically conductive material 186-3 defines a plurality of gap spaces 183.

In some example embodiments, the instance of electrically conductive material 186-3 is configured to directly contact one or more electrically conductive instruments, based on the flavor cartridge 180-3 moving, along the longitudinal axis 187 and leading by the tip-end opening 181-1, towards the one or more electrically conductive instruments, such that the one or more electrically conductive instruments directly contact an outer surface 188-3 of the instance of electrically conductive material 186-3. The instance of electrically conductive material 186-3 may be configured to be at least partially pierced by one or more electrically conductive instruments to be directly contacted by the electrically conductive instruments.

Referring back to FIGS. 2A-2C generally, in some example embodiments, a flavor cartridge 180 may include one or more instances of electrically conductive material 186-1 to 186-3. In some example embodiments, the one or more instances of electrically conductive material may include an instance of electrically conductive material that extends over both 1) a side surface of the flavor material 184 that extends coaxially with the longitudinal axis of the flavor cartridge 180 and 2) an end surface of the flavor material 184 that extends orthogonally to the longitudinal axis 187 of the flavor cartridge 180. Such an instance of electrically conductive material may, for example, include a combination of the "band" instance of electrically conductive material 186-1 shown in FIG. 2A and the "disc" instance of electrically conductive material 186-2 shown at FIG. 2C, where the resulting combination is a continuous band of electrically conductive material that extends both coaxially with the longitudinal axis 187 of the flavor cartridge 180 and at least partially orthogonally with the longitudinal axis 187 of the flavor cartridge 180. Such a band of electrically conductive material may be configured to establish an electrical connection between a first electrically conductive instrument that contacts an end of the flavor cartridge 180 (e.g., the tip end) and a side of the flavor cartridge 180 (e.g., an outer surface of the containment structure 182).

Figure 2D:
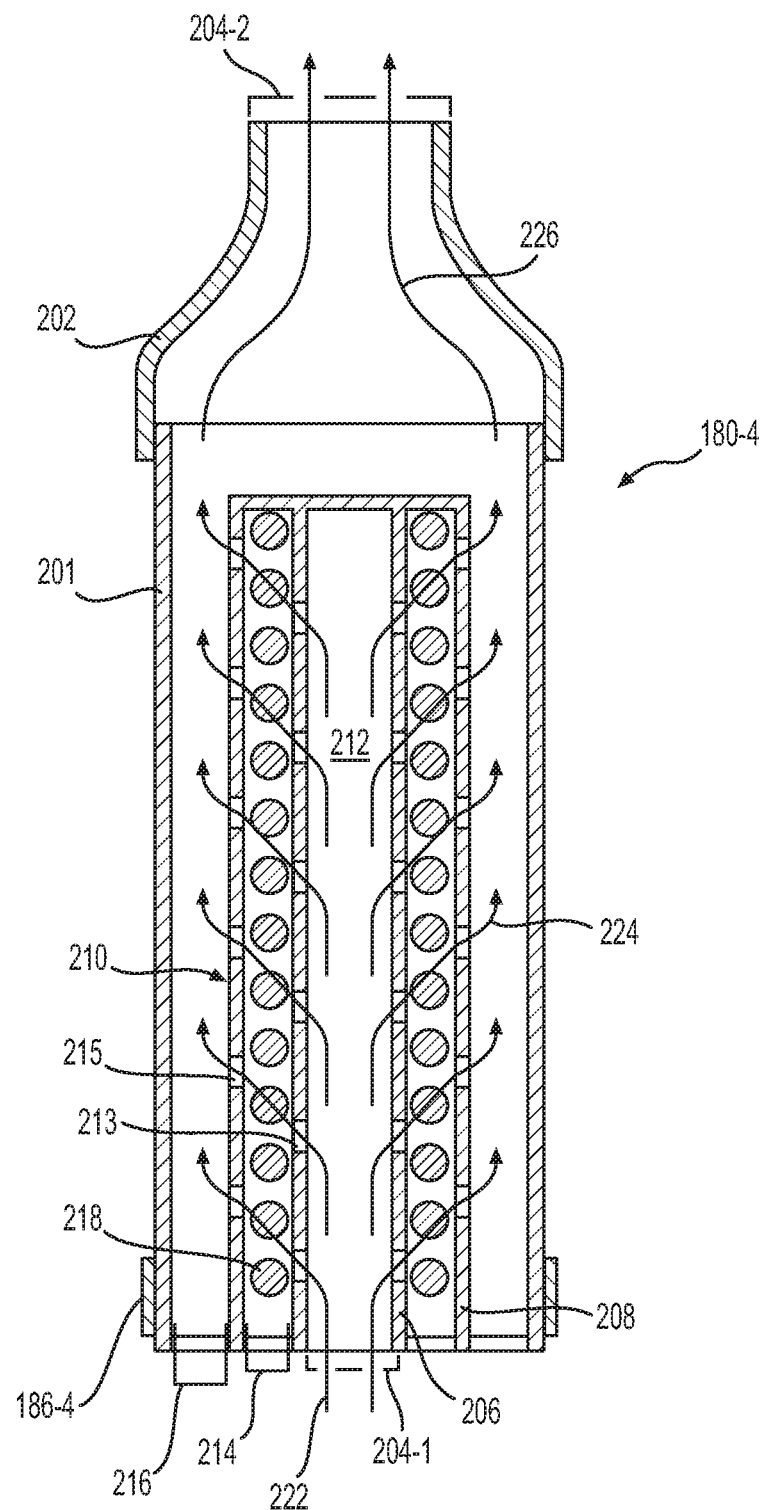

Referring now to FIG. 2D, in some example embodiments a flavor cartridge 180-4 may include a flavor housing and a flavor matrix within the flavor housing, where the flavor housing further includes a plurality of perforations configured to direct air to flow in fluid communication with the flavor matrix. Furthermore, as shown in FIG. 2D, in some example embodiments a flavor cartridge 180 may include an outlet-end insert.

The flavor cartridge 180-4 shown in FIG. 2D includes an outer housing 201 and an outlet-end insert 202 coupled to an outlet end of the outer housing 201. The flavor cartridge 180-4 is configured to receive a generated vapor 222 into a tip end of the outer housing, convert the generated vapor 222 into a flavored vapor 224, and enable the flavored vapor 224 to exit the flavor cartridge 180-4 as flavored vapor 226 via the outlet-end insert 202.

As shown in FIG. 2D, the outer housing 201 encloses a flavor housing 210 that defines a central channel 212 and an inner annular space 214. The flavor housing 210 further defines an outer annular space 216 between the flavor housing 210 and the outer housing 201.

The flavor housing 210 includes an inner structure 206 and an outer structure 208. The inner structure 206 defines a central channel 212 that extends into the interior of the flavor cartridge 180 from a tip-end opening 204-1 at the tip end of the flavor cartridge 180-4 in FIG. 2D, where the tip-end opening 204-1 is also defined by at least one of the inner structure 206 and the outer housing 201. The outer structure 208 extends around the inner structure 206, such that the inner structure 206 and the outer structure 208 collectively define an inner annular space 214.

As shown in FIG. 2D, the flavor housing 210 includes a flavor matrix 218 within the inner annular space 214. As shown in FIG. 2D, a flavor matrix 218 may include a set ("plurality") of pellets. The pellets may be made of or include, for example, at least one of starch, cellulosic material, cellulose-based material or polymer and cellulose blend, and one or more fibers. The pellets may include (e.g., may be infused with) one or more flavorants. A concentration of flavorant in the pellets may be about a %, "a" being, for example, about 1% to about 40%, or for example about 1% to about 7%. In example embodiments, "a" may range between about 3% and about 7%, with intervals of about 0.5%. Accordingly, "a" may be equal to about 3%, 3.5%, 4%, 4.5%, 5%, 5.5%, 6%, 6.5% and 7%. In some example embodiments, the flavor matrix 218 may include multiple separate sets ("pluralities") of pellets, where each separate set of pellets includes a separate set of one or more flavorants therein.

In example embodiments, the flavor matrix 218 includes a plurality of pellets that are aggregated together via pressure. For example, there may not be a ligand or gel to coalesce or aggregate the plurality of pellets. The pellets may be made of or include, for example, starch, cellulosic material, cellulose-based material or polymer and cellulose blend, and/or fibers. In some example embodiments, a ligand or gel may be present in the flavor matrix 218 to coalesce or aggregate the plurality of pellets. The gel may be made via, for example, a gelling polymer. Examples of a gelling polymer may be water soluble carbohydrates such as, for example, agar, hydroxyethyl cellulose and gelan.

As further shown in FIG. 2D, the inner structure 206 includes a plurality of perforations 213 that enable the interior of the inner annular space 214, and thus the flavor matrix 218, to be in fluid communication with the central channel 212.

As further shown in FIG. 2D, the outer structure 208 includes a plurality of perforations 215 that enable the interior of the inner annular space 214, and thus the flavor matrix 218, to be in fluid communication with the outer annular space 216. In addition, the outer annular space 216 is in fluid communication with the outlet-end insert 202.

As shown in FIG. 2D, the outlet-end insert 202 defines an outlet-end opening 204-2 in the flavor cartridge 180-4. The outlet-end opening 204-2 is in fluid communication with the outer annular space 216.

Still referring to FIG. 2D, in some example embodiments, the flavor cartridge 180-4 is configured to receive generated vapor 222 from a vapor generator into the central channel 212 via the tip-end opening 204-1. As shown in FIG. 2D, the generated vapor 222 may be directed to pass from the central channel 212 to the outer annular space 216 via perforations 213, the inner annular space 214, and perforations 215. Based on directing the generated vapor 222 to pass into the outer annular space 216 via the inner annular space 214 in which the flavor matrix 218 is located, the flavor cartridge 180 is configured to generate a flavored vapor 224 from the generated vapor 222, based on the entrainment of flavorants from the flavor matrix 218 into the generated vapor 222 passing through the inner annular space 214.

The flavor cartridge 180-4 may be further configured to direct the flavored vapor 224 entering the outer annular space 216 to flow through the outlet-end insert 202 to exit the flavor cartridge 180-4 via the outlet-end opening 204-2. Based on air being drawn through the outlet-end opening 204-2 and out of the flavor cartridge 180-4, the generated vapor 22 may be drawn into the central channel 212 and through the inner annular space 214 to generate the flavored vapor 224.

In some example embodiments, the internal configuration of a flavor cartridge 180-4 that includes a flavor matrix may be different from the configuration shown in FIG. 2D. For example, in some example embodiments, the outer annular space 216 may be open, at the tip end, to the exterior environment, such that the tip-end opening 204-1 is an annular opening at a tip end of the outer annular space 216. In addition, the central channel 212 may be in fluid communication with the outlet-end insert 202 and may be isolated from direct fluid communication with the exterior environment via the tip end of the central channel (i.e., the tip-end opening 204-1 shown in FIG. 2D may be absent from the tip end of the central channel 212. As a result, the flavor cartridge 180-4 may be configured to receive generated vapor 222 into the outer annular space 216 via the annular tip-end opening 204-1 and may further direct the generated vapor 222 into the central channel 212 via the inner annular space 214 to cause a flavored vapor to be generated and to enter the central channel, where the flavored vapor 224 may be directed from the central channel 212 to the outlet-end opening 204-2.

In some example embodiments, the inner structure 206 and outer structure 208 may be absent, and the flavor matrix 218 may extend partially or entirely through the inner diameter of the outer housing 201, such that generated vapor 222 received into the interior of the flavor cartridge 180-4 is directed to flow through the flavor matrix 218 to reach the outlet-end opening 204-2.

Still referring to FIG. 2D, a flavor cartridge 180-4 that includes a flavor matrix and/or an outlet-end insert may include an instance of electrically conductive material 186-4 that is configured to establish an electrical connection between at least two separate electrically conductive instruments contacting the instance of electrically conductive material 186-4, based on the flavor cartridge 180-4 being inserted into a channel space of a vapor cartridge that includes the at least two separate electrically conductive instruments. Thus, the flavor cartridge 180-4 may be configured to enable a non-combustible vaping device 100 to detect the presence ("insertion") of the flavor cartridge 180-4 in the channel space of the non-combustible vaping device 100.

In FIG. 2D, the instance of electrically conductive material 186-4 is shown as extending at least partially around an outer surface of the outer housing 201 and along a longitudinal axis of the flavor cartridge 180, but it will be understood that the instance of electrically conductive material 186-4 may extend on one or more various surfaces of a flavor cartridge 180-4 that includes a flavor matrix and/or an outlet-end insert, including along a tip-end surface of the flavor cartridge 180-4, along an inner surface of the outer housing 201, some combination thereof, or the like.

Authentication Assembly with Bridging Conductive Instruments

FIG. 3A, FIG. 3B, and FIG. 3C are each a perspective view of an authentication assembly configured to establish an electrical connection through at least a portion of a flavor cartridge, according to some example embodiments.

As shown in FIGS. 3A-3C, an authentication assembly 150 may include one or more sets ("pluralities") of electrically conductive instruments having one or more shapes and configurations. Various sets of electrically conductive instruments may be configured to directly contact an instance of electrically conductive material, of a flavor cartridge 180, via various operations and interactions, as described below.

As described herein, a set of electrically conductive instruments that are configured to establish an electrical connection there between via at least a portion of a flavor cartridge, such that the electrically conductive instruments are electrically connected to each other via an electrically conductive material of the flavor cartridge, may be referred to herein as "bridging conductive instruments."

Referring first to FIG. 3A, in some example embodiments, an authentication assembly 150 includes a plurality of plate instruments that are configured to directly contact an instance of electrically conductive material that extends along an outer side surface of a flavor cartridge 180, at least partially coaxially with the longitudinal axis of the flavor cartridge 180, via flush contact between surfaces of the separate plate instruments and separate, respective surface portions of the instance of electrically conductive material.

In particular, FIG. 3A illustrates an authentication assembly 150 that includes two separate electrically conductive instruments 152-1 to 152-2 that are plate instruments having separate, respective surfaces 153-1 to 153-2. As shown in FIG. 3A, the plate instruments may be curved such that the surfaces 153-1 to 153-2 have curvatures that approximate and/or match the curvature of an outer surface of a flavor cartridge 180. However, it will be understood that a plate instrument may have one or more various curvatures, and a plate instrument may include a planar surface that is configured to engage in flush contact with a portion of an instance of electrically conductive material in a flavor cartridge 180. A plate instrument may be configured to directly contact a portion of an instance of electrically conductive material based on flush contact between the surface of the plate instrument with a surface of the portion of the instance of electrically conductive material. In FIG. 3A, for example, the electrically conductive instruments 152-1 to 152-2 are configured to directly contact a given instance of electrically conductive material, of a flavor cartridge 180 that is inserted through the gap space 300 between the electrically conductive instruments 152-1 to 152-2, such that the separate, respective surfaces 153-1 to 153-2 of the electrically conductive instruments 152-1 to 152-2 directly contact separate surface portions of the instance of electrically conductive material of the flavor cartridge, thereby establishing an electrical connection between the electrically conductive instruments 152-1 to 152-2 through the instance of electrically conductive material.

As shown in FIG. 3A, the electrically conductive instruments 152-1 to 152-2 are spaced apart by a gap space 300. The gap space 300 may be equal to or less than an outer diameter of the flavor cartridge 180 that may be inserted through the gap space 300. If and/or when the outer diameter of the flavor cartridge 180 is greater than the gap space 300, the electrically conductive instruments 152-1 to 152-2 may be coupled to one or more respective springs that enable the electrically conductive instruments 152-1 to 152-2 to be pushed outward by the flavor cartridge 180, thereby enabling the electrically conductive instruments 152-1 to 152-2 to exert a spring force on the instance of electrically conductive material to ensure good electrical contact between the electrically conductive instruments 152-1 to 152-2 and the instance of electrically conductive material.

Referring now to FIG. 3B, in some example embodiments, an authentication assembly 150 includes a plurality of plate instruments that are configured to directly contact an instance of electrically conductive material that extends along an outer end surface of a flavor cartridge 180, at least partially orthogonally with the longitudinal axis of the flavor cartridge 180, via flush contact between surfaces of the separate plate instruments and separate, respective surface portions of the instance of electrically conductive material.

In particular, FIG. 3B illustrates an authentication assembly 150 that includes two separate electrically conductive instruments 152-1 to 152-2 on a cylindrical support structure 302. As shown in FIG. 3B, separate electrical leads 154-1 to 154-2 may extend through the support structure 302 to separate electrically conductive instruments 152-1 to 152-2, respectively. The support structure 302 may be at least partially electrically insulating, such that the separate electrically conductive instruments 152-1 to 152-2 are at least partially isolated from being electrically connected to each other through the support structure 302.

In FIG. 3B, the electrically conductive instruments 152-1 to 152-2 may be plate instruments as described above with reference to FIG. 3A, where the electrically conductive instruments 152-1 to 152-2 in FIG. 3B are configured to each directly contact, via flush contact of surfaces, separate surface portions of an instance of electrically conductive material that extends at least partially around a tip-end surface of a flavor cartridge 180 that is inserted into a channel space of a non-combustible vaping device 100. The authentication assembly 150 shown in FIG. 3B may be located at a tip end of the channel space 104, such that the flavor cartridge 180 is inserted towards flush contact with the electrically conductive instruments 152-1 to 152-2 if and/or when the flavor cartridge 180 is inserted into the channel space 104.

As further shown in FIG. 3B, the support structure 302 may include at least one gap space 304 such that the authentication assembly 150 may be located between the vapor generator 144 and the flavor cartridge 180 and may direct generated vapor to pass from the vapor generator 144 to the flavor cartridge 180. As noted in FIG. 2C, the flavor cartridge 180 that includes an instance of electrically conductive material 186-3 at the tip end at which the tip-end opening 181-1 is located thereof may itself include a gap space 183 that directs the generated vapor into an interior of the flavor cartridge 180.

Referring now to FIG. 3C, in some example embodiments, an authentication assembly 150 includes a plurality of spike instruments that are configured to directly contact an instance of electrically conductive material that extends along an outer end surface of a flavor cartridge 180, at least partially orthogonally with the longitudinal axis of the flavor cartridge 180, via at least partially impinging and/or piercing separate, respective portions of the instance of electrically conductive material. As shown in FIG. 2C, such an instance of electrically conductive material may be a disc, cylindrical disc, some combination thereof, or the like.

In particular, FIG. 3C illustrates an authentication assembly 150 that includes two separate electrically conductive instruments 152-1 to 152-2 on a cylindrical support structure 302. As shown in FIG. 3C, separate electrical leads 154-1 to 154-2 may extend through the support structure 302 to separate electrically conductive instruments 152-1 to 152-2, respectively. The support structure 302 may be at least partially electrically insulating, such that the separate electrically conductive instruments 152-1 to 152-2 are at least partially isolated from being electrically connected to each other through the support structure 302.

In FIG. 3C, the electrically conductive instruments 152-1 to 152-2 may be spike instruments, where the electrically conductive instruments 152-1 to 152-2 in FIG. 3C are configured to each directly contact, via impinging and/or piercing, separate portions of an instance of electrically conductive material that extends at least partially around a tip-end surface of a flavor cartridge 180 that is inserted into a channel space of a non-combustible vaping device 100.

The authentication assembly 150 shown in FIG. 3C may be located at a tip end of the channel space 104, such that the flavor cartridge 180 is inserted towards flush contact with the electrically conductive instruments 152-1 to 152-2 if and/or when the flavor cartridge 180 is inserted into the channel space 104.

As further shown in FIG. 3C, the support structure 302 may include at least one gap space 304 such that the authentication assembly 150 may be located between the vapor generator 144 and the flavor cartridge 180 and may direct generated vapor to pass from the vapor generator 144 to the flavor cartridge 180. As noted in FIG. 2C, the flavor cartridge 180 that includes an instance of electrically conductive material 186-3 at the tip end (at which the tip-end opening 181-1 is located) thereof may itself include a gap space 183 that directs the generated vapor into an interior of the flavor cartridge 180.

FIG. 4A, FIG. 4B, and FIG. 4C are each a cross-sectional view of a vapor cartridge of a non-combustible vaping device illustrating an insertion of a flavor cartridge through a channel space of the vapor cartridge according to some example embodiments.

Referring generally to FIGS. 4A-4C, in some example embodiments, an authentication assembly 150 may include a set ("plurality") of electrically conductive instruments 152-1 to 152-2 that include at least one blade instrument. A blade instrument may be configured to directly contact at least a portion of an instance of electrically conductive material based on piercing and/or cutting through one or more portions of a flavor cartridge 180 as the flavor cartridge 180 is moved through a channel space 104 of the non-combustible vaping device 100. The blade instrument may be configured to pierce and/or cut through a limited portion of the flavor cartridge. For example, if and/or when the flavor cartridge 180 includes an instance of electrically conductive material 186-2 that extends along an outer surface of a containment structure 182 as shown in FIG. 2B, a blade instrument of the authentication assembly 150 may be configured to cut through the instance of electrically conductive material 186-2 and may be configured to not cut through the containment structure 182. In another example, as shown in FIGS. 4A-4C, if and/or when the flavor cartridge 180 includes an instance of electrically conductive material 186-1 that is isolated from exposure by the containment structure 182 as shown in FIG. 2A, a blade instrument of the authentication assembly 150 may be configured to cut through at least the containment structure 182. A blade instrument may be configured to not cut through the instance of electrically conductive material of a flavor cartridge 180 but instead simply impinge upon a surface of the instance of electrically conductive material.

FIGS. 4A-4C illustrate an authentication assembly 150, included in the vapor cartridge 140 shown in FIGS. 1A-1B, wherein the authentication assembly 150 includes electrically conductive instruments 152-1 to 152-2 that are each blade instruments, such that each of the electrically conductive instruments 152-1 to 152-2 are configured to cut through at least the containment structure 182 and the instance of electrically conductive material 186-1 of the flavor cartridge shown in FIG. 2A.

It will be understood that, in some example embodiments, separate electrically conductive instruments in a set thereof, of an authentication assembly 150, may be different types of instruments (e.g., blade, plate, spike, some combination thereof, or the like). For example, an authentication assembly 150 may include an electrically conductive instrument 152-1 that is a plate instrument extending along a longitudinal axis of a channel space 104 and an electrically conductive instrument 152-2 that is a spike instrument extending orthogonally to the longitudinal axis of the channel space 104.

As shown in FIGS. 4A-4C, the authentication assembly 150 in some example embodiments may include electrically conductive instruments 152-1 to 152-2 that extend into the channel space 104 via gaps in a channel structure 142 that at least partially defines the channel space 104. As shown, the electrically conductive instruments 152-1 to 152-2 may each extend a particular intrusion distance 404 into the channel space 104, such that the gap space 402 between the electrically conductive instruments 152-1 to 152-2 is less than the diameter 400 of the channel space 104. As further shown in FIGS. 4A-4C, the channel structure 142 may be configured to receive, into the channel space 104, a flavor cartridge 180 having an outer diameter that corresponds to the diameter 400 of the channel space 104. Thus, the gap space 402 between the electrically conductive instruments 152-1 to 152-2 is less than the outer diameter of the flavor cartridge 180.

As shown in FIGS. 4A-4C, the flavor cartridge 180 that is inserted into the channel space 104 may be at least partially similar to the flavor cartridge 180 shown in FIG. 2A, wherein the flavor cartridge 180 includes an instance of electrically conductive material 186-1 that is isolated from exposure by the containment structure 182 of the flavor cartridge 180. As further shown in FIGS. 4A-4C, the diameter of the instance of electrically conductive material 186-1 may be greater than the magnitude of the gap space 402.

Referring to FIG. 4A, the flavor cartridge 180 including the instance of electrically conductive material 186-1 may be inserted into the channel space 104 at least partially defined by the channel structure 142, via an outlet-end opening of the channel structure 142, so that the flavor cartridge is moved through the channel space 104 towards the electrically conductive instruments 152-1 to 152-2. In FIG. 4A, the electrically conductive instruments 152-1 to 152-2 are isolated from being electrically connected to each other by at least the gap space 402 therebetween. As a result, an electrical current between the electrically conductive instruments 152-1 to 152-2 across the gap space 402 is inhibited.

Referring now to FIG. 4B, if and/or when the flavor cartridge 180 is moved sufficiently far through the channel space 104 to reach the electrically conductive instruments 152-1 to 152-2, the electrically conductive instruments 152-1 to 152-2 may cut through the containment structure 182, the instance of electrically conductive material 186-1, and at least a portion of the flavor material 184 as the flavor cartridge 180 continues to move through the channel space 104 past the electrically conductive instruments 152-1 to 152-2.

As shown in FIG. 4B, if and/or when the electrically conductive instruments 152-1 to 152-2 begin to cut through the flavor cartridge 180 and further begin to cut through the instance of electrically conductive material 186-1, the electrically conductive instruments 152-1 to 152-2 may become electrically connected to each other through the instance of electrically conductive material 186-1.

As a result, and as further shown in FIG. 4B, an electrical connection 408 that electrically bridges the gap space 402 between the electrically conductive instruments 152-1 to 152-2 is established by the instance of electrically conductive material 186-1.

Furthermore, and as shown in FIG. 4B, if and/or when the electrical leads 154-1 to 154-2 are respectively coupled to a power supply (not shown in FIGS. 4A-4B), such that a potential difference exists between the electrically conductive instruments 152-1 to 152-2, the establishment of the electrical connection 408 may result in the inducement of an electrical current 410 that passes at least between the electrically conductive instruments 152-1 to 152-2 via the instance of electrically conductive material 186-1 and further passes along the electrical leads 154-1 and 154-2.

In some example embodiments, at least a portion of a non-combustible vaping device 100 that includes the authentication assembly 150 shown in FIGS. 4A-4C may be configured to detect the induced electrical current 410. The portion of the non-combustible vaping device 100 that includes the authentication assembly 150 may further be configured to determine, based on detecting the induced electrical current 410, that the flavor cartridge 180 is present within the channel space 104 of the vapor cartridge 140. The portion of the non-combustible vaping device 100 may further be configured to selectively and/or adjustably control the supply of electrical power to a vapor generator 144 based on determining that the flavor cartridge 180 is present within the channel space 104 of the vapor cartridge 140. As a result, the non-combustible vaping device 100 that includes the authentication assembly 150 shown in FIGS. 4A-4C may be configured to selectively and/or adjustably control vapor generation by a vapor generator 144 thereof based on the establishment of the electrical connection 408 between the electrically conductive instruments 152-1 to 152-2 through the instance of electrically conductive material 186-1 of the flavor cartridge 180.

Referring now to FIG. 4C, in some example embodiments the instance of electrically conductive material 186-1 in a flavor cartridge 180 extends along only a limited portion of the longitudinal axis of the flavor cartridge 180. As a result, as the flavor cartridge 180 is moved further through the channel space 104 and past the electrically conductive instruments 152-1 to 152-2, the electrically conductive instruments 152-1 to 152-2 may cut through an entirety of the longitudinal distance of the instance of electrically conductive material 186-1, such that the instance of electrically conductive material 186-1 is detached from direct contact with the electrically conductive instruments 152-1 to 152-2 as the flavor cartridge 180 is moved further through the channel space 104. As a result, the electrically conductive instruments 152-1 to 152-2 may become electrically disconnected from each other, as the flavor material 184 may insulate the separation 412 between the electrically conductive instruments 152-1 to 152-2 through the flavor cartridge 180. Thus, the electrical current 410 may cease.

In addition, as the flavor cartridge 180 is moved further through the channel space 104 and past the electrically conductive instruments 152-1 to 152-2, the electrically conductive instruments 152-1 to 152-2 may cut through an entirety of the longitudinal distance of the instance of electrically conductive material 186-1, thereby severing the instance of electrically conductive material 186-1 into at least two (e.g., a plurality) of separate pieces. As a result, the flavor cartridge 180 may be precluded from enabling the electrical connection 408 from being re-established if and/or when the flavor cartridge 180 is moved back through the channel space 104 and/or re-inserted into the channel space. For example, if and/or when the instance of electrically conductive material 186-1 is a band that extends continuously around the flavor material 184 in the flavor cartridge 180, the electrically conductive instruments 152-1 to 152-2 may sever the band into separate instances, such that the instance of electrically conductive material 186-1 is inhibited from re-establishing an electrical connection between the electrically conductive instruments 152-1 to 152-2.

Authentication Assembly with Displaceable Instrument

FIG. 5A and FIG. 5B are each a cross-sectional view of a vapor cartridge of a non-combustible vaping device illustrating an insertion of a flavor cartridge through a channel space of the vapor cartridge according to some example embodiments.

Referring generally to FIGS. 5A-5B, in some example embodiments, an authentication assembly 550 may include a set ("plurality") of electrically conductive instruments 582 and 584 that include at least one physically-displaceable electrically conductive instrument. A physically-displaceable electrically conductive instrument, also referred to herein as simply a "displaceable instrument," may be configured to be physically displaced (e.g., moved, bent, flexed, some combination thereof, or the like) based on direct contact with a portion of a flavor cartridge 580 as the flavor cartridge 580 is moved through a channel space 504 of the vapor cartridge 540 of a non-combustible vaping device 500. The displaceable instrument may be configured to be physically displaced by the flavor cartridge 580 such that the displaceable instrument comes into contact with another electrically conductive instrument (e.g., a fixed instrument) to establish a closed electrical circuit.

As a result of the closed electrical circuit being formed through at least the displaceable instrument and the contacted electrically conductive instrument, an electrical signal may pass through the closed electrical circuit. For example, the closed electrical circuit may include a power supply and a control circuitry, and establishing the closed electrical circuit may include inducing an electrical current through the closed electrical circuit, such that the control circuitry detects the electrical current and determines that the flavor cartridge 580 is inserted in the vapor cartridge 540 based on detecting the electrical current.

FIGS. 5A-5B illustrate a vapor cartridge 540 that includes an authentication assembly 550. The authentication assembly 550 includes a set of electrically conductive instruments that includes a displaceable instrument 582 and a fixed instrument 584. The displaceable instrument 582 is coupled to an electrical connector 552-3 and the fixed instrument 584 is coupled to an electrical connector 552-2. If and/or when the vapor cartridge 540 is coupled to base 510 to establish the non-combustible vaping device 500, the electrical connectors 552-2 and 552-3 may be connected to corresponding electrical connectors 514-2 and 514-3 of the base 510. As shown in FIGS. 5A-5B, the electrical connectors 514-2 and 514-3 may be electrically coupled to a power supply 512 and an instance of control circuitry 513 in the base 510. Thus, the authentication assembly 550, in combination with electrical connectors 552-2 to 552-3, electrical connectors 514-2 to 514-3, power supply 512, and control circuitry 513 may collectively establish an electrical circuit.

The control circuitry 513 may be configured to determine whether a flavor cartridge 580 is inserted into the vapor cartridge 540 based on a determination of whether an electrical current (e.g., an electrical current having at least a threshold magnitude) is detected in the aforementioned electrical circuit. The control circuitry 513 may be configured to selectively control the supply of electrical power from the power supply 512 to the vapor generator 544 of the vapor cartridge 540, via electrical connectors 514-1 and 552-1, based on the determination.

In some example embodiments, one or more electrical connectors, of the electrical connectors 514-1 to 514-3 and/or 552-1 to 552-3, may be a pogo pin connector. For example, electrical connectors 514-1 to 514-3 may each be a pogo pin connector. In another example, electrical connectors 552-1 to 552-3 may each be a pogo pin connector.

Referring now to FIG. 5A, the authentication assembly 550 may be configured to establish a gap space between the displaceable instrument 582 and the fixed instrument 584 in the absence of a flavor cartridge 580 being inserted into the vapor cartridge 540, such that the aforementioned electrical circuit is opened and an electrical current having at least the threshold magnitude is inhibited. Such a configuration, as shown in FIG. 5A, may be referred to as a "rest state" of one or more portions of the authentication assembly 550. In contrast, the configuration shown in FIG. 5B and described further below may be referred to as a "displaced state" of one or more portions of the authentication assembly 550.

Vapor cartridge 540 includes a channel structure 542 that at least partially defines a channel space 504 extending between an opening 502 in the housing of the vapor cartridge 540 to a vapor generator 544 in the vapor cartridge 540. As shown in FIG. 5A, the channel structure 542 may have an inner diameter 590 that establishes a diameter of the channel space 504. The inner diameter 590 of the channel structure 542 may correspond to (e.g., may match within a particular margin) an outer diameter of the flavor cartridge 580.

As further shown in FIG. 5A, the channel structure 542 includes a thick side portion 581 that includes a cavity 589 and a portal 586 collectively extending there through, such that at least the portal 586 defines an opening in the inner surface of the channel structure 542 and the channel space 504 at least partially defined by the channel structure 542 is in fluid communication with the exterior of the channel structure 542 through the portal 586 and the cavity 589.

In some example embodiments, the displaceable instrument 582 includes a displaceable portion 588 that extends through the cavity 589 and further through the portal 586 to at least partially extend into the channel space 504 via the opening in the inner surface of the channel structure 542 that is at least partially defined by the portal 586. As shown in FIG. 5A, for example, the displaceable portion has an approximate "V" shape, the vertex of which extends through the portal 586 an into the channel space 504 by at least an impingement distance 593.

As further shown in FIG. 5A, the distance 592 between the displaceable portion 588 extending into the channel space 504 and a distal portion of the inner surface of the channel structure 542 (e.g., a constricted diameter of the channel space 504 caused by the impingement of the displaceable portion 588 into the channel space 504 via portal 586) may be less than the inner diameter 590 of the channel structure 542.

As indicated above, the inner diameter 590 may correspond to the outer diameter of the flavor cartridge 580. As a result, the distance 592 may be less than the outer diameter of the flavor cartridge 580, and the inner diameter 590 may correspond to a sum of distance 592 and impingement distance 593.

In some example embodiments, the displaceable instrument 582 may be configured to be in a "rest state" if and/or when a flavor cartridge 580 is absent from being in direct contact with the displaceable instrument 582. FIG. 5A illustrates a displaceable instrument 582 that is in a rest state, and FIG. 5B illustrates a displaceable instrument 582 that is in a "displaced state" based on being contacted by a flavor cartridge 580 inserted into the vapor cartridge 540.

As shown in FIG. 5A, the displaceable instrument 582 may be configured to be physically separated from the fixed instrument 584, based on the displaceable instrument 582 being in a rest state. As shown, the tip 599 of the displaceable instrument 582 is separated from the fixed instrument 584 by a gap space 594. As a result, based on the displaceable instrument 582 being in a rest state, as shown in FIG. 5A, the displaceable instrument 582 may be isolated from being directly connected to the fixed instrument 584, and thus isolated from being directly electrically connected to the fixed instrument 584, based on the gap space 594 therebetween. The magnitude ("distance") of the gap space 594 may, in some example embodiments, correspond to the magnitude of the impingement distance 593. In some example embodiments, the magnitudes of the gap space 594 and the impingement distance 593 may be different.

In some example embodiments, including the example embodiments shown in FIGS. 5A-5B, the displaceable instrument 582 is configured to be at least partially displaced, based on the flavor cartridge 580 directly contacting at least the displaceable portion 588, such that the displaceable instrument 582 directly contacts the fixed instrument 584, thereby establishing a direct electrical connection between the displaceable instrument 582 and the fixed instrument 584 and further closing the aforementioned electrical circuit that includes at least the authentication assembly 550, the power supply 512, and the control circuitry 513.

In some example embodiments, at least a portion of the displaceable instrument 582 is fixed to a portion of the vapor cartridge 540. For example, in the example embodiments shown in FIGS. 5A and 5B, the displaceable instrument 582 includes a fixed portion 587 and the aforementioned displaceable portion 588, where the fixed portion 587 is fixed to the channel structure 542 and the displaceable portion 588 is configured to be displaced by the flavor cartridge 580. In some example embodiments, the displaceable instrument 582 may be configured to be entirely displaceable. For example, the displaceable instrument 582 may be coupled to a hinge and/or spring instrument, such that the displaceable instrument 582 is configured to be entirely displaced by the flavor cartridge 580.

Referring now to FIG. 5B, if and/or when a flavor cartridge 580 is inserted into the vapor cartridge 540 through the opening 502, such that the flavor cartridge 580 is inserted through the channel space 504, the flavor cartridge 580 may directly contact at least the displaceable portion 588 of the displaceable instrument 582 that extends at least the impingement distance 593 into the channel space 504.

As mentioned above, the outer diameter of the flavor cartridge 580 may correspond to the inner diameter 590 of the channel structure 542 (i.e., the outer diameter of the channel space 504), such that the distance between the displaceable portion 588 extending into the channel space 504 and the distal inner surface of the channel structure 542 (i.e., distance 592) is less than the outer diameter of the flavor cartridge 580. As a result, based on being inserted into the channel space 504, the flavor cartridge 580 may directly contact the displaceable portion 588.

To continue moving through the channel space 504 towards the vapor generator 544, the flavor cartridge 580 may displace the displaceable portion 588, by at least the impingement distance 593, so that the displaceable portion 588 is displaced out of the channel space 504 via the portal 586 and the diameter of the channel space 504 between the flavor cartridge 580 and the vapor generator 544 is widened to a diameter that corresponds with the outer diameter of the flavor cartridge 580 (e.g., diameter 590).

Based on the displaceable portion 588 being displaced by the flavor cartridge 580 at least partially out of the channel space 504 (e.g., displaced by displacement distance 595, the tip 599 of the displaceable instrument 582 may be caused to close the gap space 594 between the tip 599 in the rest state and the fixed instrument 584, such that the tip 599 directly contacts the fixed instrument 582.

Based on the displaceable instrument 582 directly contacting the fixed instrument 582, the aforementioned electrical circuit that includes at least the authentication assembly 550, the power supply 512, and the control circuitry 513 may be closed. As a result, an electrical current 598 may be induced in the electrical circuit, where the electrical current 598 passes through at least the directly contacted displaceable instrument 582 and the fixed instrument 584. The control circuitry 513 may detect the electrical current and may determine, based on detecting the electrical current, that a flavor cartridge 580 is inserted into the vapor cartridge 540. The control circuitry 513 may selectively activate the vapor generator 544 (e.g., enable the supply of electrical power from the power supply 512 to the vapor generator 544) based on the determination, such that vapor generation by the vapor generator 544 is selectively enabled or disabled based on a determination, at control circuitry 513, of whether a flavor cartridge 580 is inserted into the vapor cartridge 540, as indicated by the presence or absence of an electrical current through the displaceable instrument 582 and the fixed instrument 584.

Thus, the displaceable instrument 582 and the fixed instrument 584 may selectively directly contact each other, such that the displaceable instrument 582 and the fixed instrument 584 are electrically connected to each other, based on the displaceable instrument 582 being displaced by the flavor cartridge 580 at least partially through the portal 586 of the channel structure 542.

In some example embodiments, the displaceable instrument 582 and the fixed instrument 584 are included in an electrical circuit that includes, in addition to the control circuitry 513 and the power supply 512, the vapor generator 544. The control circuitry 513 may be configured to determine whether the flavor cartridge 580 is inserted into the vapor cartridge 540 via another, separate authentication assembly (e.g., one or more assemblies of the authentication assemblies shown in FIGS. 3A-4C), while the authentication assembly 550 is configured to function as an electrical switch that selectively closes or opens the electrical circuit via which electrical power may be supplied from the power supply 512 to the vapor generator 544 based on whether the flavor cartridge 580 is inserted into, or absent from, the vapor cartridge 540, respectively.

In some example embodiments, an authentication assembly that enables the control circuitry 513 to determine whether a flavor cartridge 580 is inserted into the vapor cartridge 540 is absent from vapor cartridge 540, and an authentication assembly 550 that is present in the vapor cartridge 540 is configured to function as an electrical switch to selectively enable or disable a supply of electrical power from the power supply 512 to the vapor generator 544 based on whether a flavor cartridge 580 is inserted into the vapor cartridge 540.

As shown in FIGS. 5A-5B, the cavity 589 may be shaped to conform to the shape of the displaceable portion 588, but example embodiments will be understood to not be limited to such embodiments of the cavity 589.

In some example embodiments, the control circuitry 513 is configured to selectively enable or disable vapor generation by the vapor cartridge 540 based on a determination of whether a flavor cartridge 580 is inserted sufficiently into the channel space 504 to preclude vapor generated by the vapor generator 544 from bypassing through the channel space 504 externally to the flavor cartridge 580 (e.g., the flavor cartridge 580 is sufficiently inserted into the channel space 504 such that the channel structure 542 directs an entirety of vapor generated by the vapor generator 544 to pass through an interior of the flavor cartridge 580). For example, the non-combustible vaping device 500 may include a sensor device configured to determine whether air is being drawn through the channel space 504 towards the opening 502, and the control circuitry 513 may be configured to selectively control the supply of electrical power from the power supply 512 to the vapor generator 544, to cause the vapor generator 544 to generate vapor, based on a determination that the sensor has detected at least a threshold flow rate of air through the channel space 504 towards the opening 502.

The sensor device may be configured to be selectively precluded from determining that at least the threshold flow rate of air through the channel space 504 towards the opening 502 occurs based on whether at least a portion of the air flow passes through the channel space 504 by bypassing an interior of a flavor cartridge 580 inserted into the channel space 504. For example, if and/or when the flavor cartridge 580 is absent from the channel space 504, and at least the threshold amount of air flow passes through the channel space 504, the control circuitry 513 may be precluded from causing the vapor generator 544 to generate vapor in response to the air flow, as the sensor may be precluded from detecting at least the threshold amount of air flow as a result of the absence of the flavor cartridge 580.

Base Sensor Inlet Port and Conduit

Figure 6A:
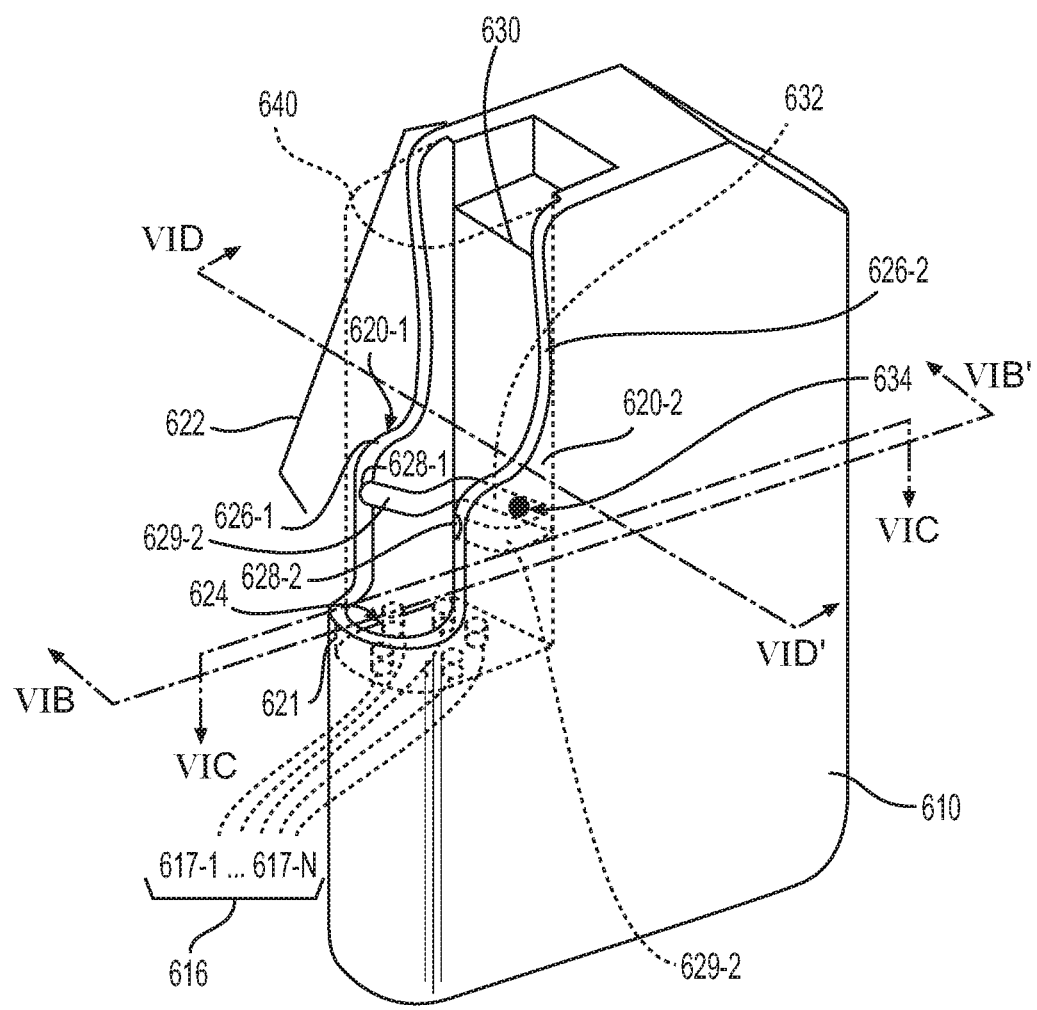
FIG. 6A is a perspective view of a base of a non-combustible vaping device according to some example embodiments.

FIG. 6A is a perspective view of a base of a non-combustible vaping device according to some example embodiments. FIG. 6B is a cross-sectional view of the base of FIG. 6A along line VIB-VIB'. FIG. 6C is a cross-sectional view of the base of FIG. 6A along line VIC-VIC'. FIG. 6D is a cross-sectional view of the base of FIG. 6A along line VID-VID'.

As shown in FIGS. 6A-6D, a base 610 that is configured to couple with a vapor cartridge 640 to form a non-combustible vaping device may include one or more structural elements, referred to herein as "guide walls," that at least partially define a cavity (also referred to herein as interface "slot") into which the vapor cartridge 640 may be inserted to be aligned with and coupled with the base 610.

Base 610 includes an outer housing 611 that further includes at least guide walls 620-1, 620-2, 621, and 630-1 and base surface 624. The guide walls 620-1, 620-2, 621, and 630 are configured to guide and hold opposing sidewalls of a vapor cartridge in alignment with the base surface 624 of base 610, so that an interface of the vapor cartridge 640 is aligned with the interface 616 of the base 610.

As further shown, the base surface 624 that establishes a base of the cavity 622 further includes base interface 616. Base interface 616, which may correspond to the interface 160-1 shown in FIGS. 1A-1B, includes a set of one or more electrical connectors 617-1 to 617-N that are each configured to couple with a separate corresponding electrical connector of an interface of the vapor cartridge 640. One or more connectors of connectors 617-1 to 617-N may be a pogo pin connector.

In some example embodiments, the interface 616 may include a plurality of sets of connectors 617-1 to 617-N that are each configured to conduct separate sets of signals between the base 610 and a coupled vapor cartridge 640. For example, in the example embodiments illustrated in FIGS. 6A-6D, interface 616 includes five pogo pin connectors 617-1 to 617-5 (e.g., 617-1 to 617-N where N=5). A first set of two connectors of the five connectors (e.g., connectors 617-1 and 617-2) may be configured to supply electrical power to one or more elements of the vapor cartridge 640 (e.g., supply electrical power from power supply 612 to a vapor generator of the vapor cartridge 640, as shown in FIGS. 1A-1B). Another set of two connectors of the five connectors (e.g., connectors 617-3 and 617-4) may be configured to communicate data between elements of the base 610 and elements of the vapor cartridge 640 (e.g., communicate information indicating a pre-vapor formulation flavor type of pre-vapor formulation held in the vapor cartridge 640, amount of remaining pre-vapor formulation held in the vapor cartridge 640, a make and model associated with the vapor cartridge 640, a state of the vapor cartridge 640, some combination thereof, or the like to the control circuitry 614). The final set of one connector of the five connectors (e.g., connector 617-5) may be configured to communicate, from an authentication assembly in the vapor cartridge 640 (e.g., authentication assembly 150 as shown in FIG. 1B) to the control circuitry 614 to enable the control circuitry 614 to determine whether a flavor cartridge (e.g., flavor cartridge 180 as shown in FIGS. 1A-1B) is inserted into the vapor cartridge 640, thereby enabling the control circuitry 614 to selectively enable or disable vapor generation by a vapor generator of the vapor cartridge 640 based on such a determination.

In some example embodiments, as shown in FIGS. 6A-6D, the guide walls 620-1, 620-2 and 630 each include a separate channel structure that extends along a surface of the respective guide wall.

Guide wall 630 includes a channel 632 that extends along a surface of the guide wall 630. As shown, an air inlet port 634 that extends through the base housing 611 to be in fluid communication with a sensor 613 of the base may extend through a base of the channel 632. As a result, the sensor 613 within an interior of the base 610 may be in fluid communication with the channel 632 that extends along a portion of the outer housing of the base 610.

Guide walls 620-1 and 620-2 each include a separate respective channel 629-1 and 629-2 that extends along an inner surface of the respective guide wall 620-1 and 620-2. Each channel 629-1 and 629-2 extends from an inner edge of the respective guide wall 620-1 and 620-2, the inner edge intersecting the guide wall 630, to an outer edge 626-1 and 626-2 of the respective guide wall 620-1 and 620-2. As further shown in FIGS. 6A-6D, each channel 629-1 and 629-2 has an outlet 628-1 and 628-2 at and end that intersects the edge 626-1 and 62-2 of the respective guide wall 620-1 and 620-1. As also shown in FIGS. 6A-6D, each channel 629-1 and 629-2 is connected to a separate end of the channel 632 at the respective inner edges of guide walls 620-1 and 620-2.

As a result, channel 629-1 and a portion of channel 632 form a continuous channel extending from the outlet 628-1 to the air inlet port 634, and channel 629-2 and a separate portion of channel 632 form a continuous channel extending from the outlet 628-2 to the air inlet port 634.

In some example embodiments, if and/or when a vapor cartridge 640 is inserted into the cavity 622, such that the vapor cartridge 640 is aligned and coupled with the interface 616, one or more outer housing surfaces of the vapor cartridge 640 may enclose the channels 629-1, 629-2, and 632 of the base 610m, leaving the outlets 628-1 and 628-2 exposed to the external ("ambient") environment.

As a result, based on the vapor cartridge 640 being coupled with interface 616, the aforementioned channels may be enclosed to form a first conduit that extends continuously from outlet 628-1 to the air inlet port 634 and a second conduit that extends continuously from outlet 628-2 to the air inlet port 634. Therefore, the sensor 613 may remain in fluid communication with the external environment via the first and second conduits that are formed by the outer housing of the base 610 and the outer housing of the vapor cartridge 640.

The sensor 613 may be, similarly to the sensor 113 described above with reference to FIGS. 1A-1B, a pressure sensor that is configured to enable the control circuitry 614 of the base 110 to determine that at least a threshold magnitude of air is being drawn into the vapor cartridge 640. For example, the vapor cartridge 640 may include one or more air inlet ports (shown in FIGS. 1A-1B) via which air may be drawn into the vapor cartridge 640, and the air inlet ports may be located at particular positions on the outer housing of the vapor cartridge 640 that are proximate to the locations of the outlets 628-1 and 628-2 if and/or when the vapor cartridge 640 is coupled to interface 616.

As a result, if and/or when air is drawn into the vapor cartridge 640 via the air inlet ports of the vapor cartridge 640, concurrently with the vapor cartridge 640 being coupled to the interface 616, the ambient pressure proximate to the outlets 628-1 and/or 628-2 may change, and such a change may be detected by the sensor 613 that is in fluid communication with the outlets 628-1 and 628-2.

For example, a pressure change proximate to the outlet 628-1 and/or outlet 628-2 may result in a pressure change at the air inlet port 634 and thus at the sensor 613, as the air inlet port 634 is in fluid communication with the outlets 628-1 and 628-2. The control circuitry 614 of the base 610 may determine that air is being drawn into the vapor cartridge 640 based on determining that the sensor 613 has detecting a change in pressure. The control circuitry 614 may be configured to selectively control a supply of electrical power from power supply 612 to a vapor generator in the vapor cartridge 640, via one or more connectors 617-1 to 617-N of the interface 616, based on such a determination.

Still referring to FIGS. 6A-6D, in some example embodiments, the base 610 may include one or more interfaces 670 and 672 via which information and/or commands may be communicated between the base 610 and an adult vaper. For example, as shown in FIG. 6E, the base 610 may include a tactile interface 670 (e.g., a button interface) and a display interface 672. The display interface 672 may include a light emitting diode (LED) display that is configured to present one or more graphical displays (GUIs) that provide one or more instances of information associated with the non-combustible vaping device 600. The base 610 may be configured to adjust and/or change the display on the interface 672 based on adult vaper interaction with the tactile interface 670. For example, as described further below, the base 610 may be configured to cycle through a sequence of graphical displays, each graphical display presenting a different set of information, based on successive interactions with (e.g., "clicks" of) the tactile interface 670.

Display Interface

FIG. 7A, FIG. 7B, FIG. 7C, FIG. 7D, FIG. 7E, FIG. 7F, FIG. 7G, and FIG. 7H illustrate graphical displays that may be displayed by a display interface of a non-combustible vaping device, according to some example embodiments. The display interface 710 of the base 700, as shown in FIGS. 7A-7H, may be a display interface of any of the bases according to any of the example embodiments included herein, including the display interface 172 shown in FIGS. 1C-1E and the display interface 672 shown in FIGS. 6B-6D.

Referring generally to FIGS. 7A-7H, in some example embodiments, a display interface 710 may be controlled to cycle through a sequence of separate graphical displays, based on adult vaper interaction with one or more interfaces of the base 700 (e.g., a tactile interface), to provide separate instances of information in separate graphical displays. The display interface 710 may be controlled, by a control circuitry of the base 700, to cycle through the sequence of graphical displays based on successive adult vaper interactions with an interface of the base 700.

Still referring generally to FIGS. 7A-7H, each separate graphical display presented by the display interface 710 may include a sequence indicator icon 712 that indicates which particular graphical display, of a sequence of graphical displays, is presently being displayed. For example, in the example embodiments shown in FIGS. 7A-7H, the display interface 710 may cycle through three separate graphical displays that display three separate sets of information, and each graphical display may include the sequence indicator icon 712 that includes three separate icons 713-1, 713-2, and 713-3 that each represent a separate graphical display in the sequence, and wherein a particular icon 713-1, 713-2, or 713-3 that represents the presently-displayed graphical display is altered in relation to the other icons 713-1, 713-2, or 713-3 in order to provide an indication of which particular graphical display is presently being displayed via the display interface 710.

Figure 7A:
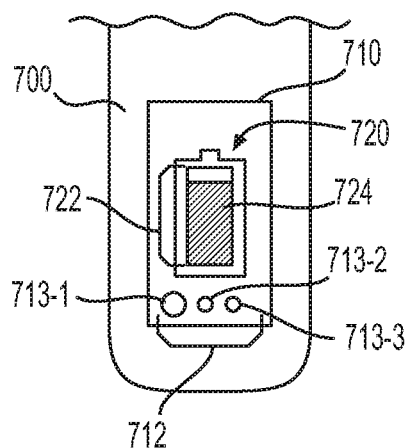
FIG. 7A, FIG. 7B, FIG. 7C, FIG. 7D, FIG. 7E, FIG. 7F, FIG. 7G, and FIG. 7H illustrate graphical displays that may be displayed by a display interface of a non-combustible vaping device, according to some example embodiments.
Figure 7B:
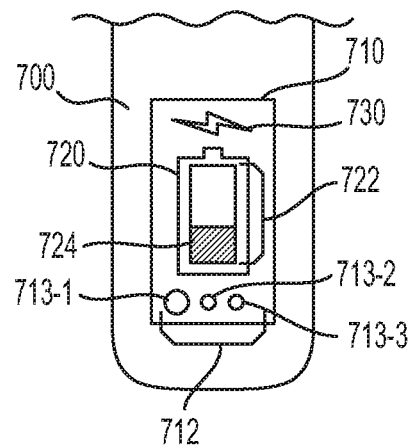

Referring now to FIG. 7A-7B, the display interface 710 may be configured to display a power graphical display ("PGD"), of a sequence of graphical displays, that indicates a state of a power supply included in the base 700. The power graphical display may indicate an amount of electrical power stored in the power supply, indicate whether the power supply is storing sufficient electrical power to support an instance of vapor generation, indicate whether the power supply is being charged/re-charged, some combination thereof, or the like.

As shown in FIGS. 7A-7B, the power graphical display may be a first graphical display of a three-display sequence. Thus, the power graphical display includes a display of the sequence indicator icon 712 wherein a first icon 713-1, of the sequence of three icons 713-1, 713-2, and 713-3 that represents the three separate graphical displays of the sequence, is changed relative to the other icons in order to convey that the presently-displayed graphical display is the first graphical display of the sequence. As shown, the first icon 713-1 is enlarged, relative to icons 713-2 and 713-3, when the power graphical display is displayed on interface 710, thereby conveying that the power graphical display is being displayed.

Still referring to FIGS. 7A-7B, the power graphical display includes a graphical representation 720 of the power supply in which a stored power meter 722 is displayed to provide an indication of the relative ("proportional") amount of stored power in the power supply of the base 700, relative to the electrical power storage capacity of the power supply.

FIG. 7A illustrates a graphical representation 720 wherein the stored power icon 724 fills nearly the entirety of the meter 722, thereby indicating that the power supply of the base 700 has nearly a full charge of electrical power.

As electrical power is consumed, expended, depleted, or the like, the size of the stored power icon 724 may shrink, such that the stored power icon 724 occupies a smaller and smaller proportion of the meter 722. For example, as shown in FIG. 7B, the stored power icon 724 occupies a relatively small portion of the meter 722, thereby indicating that the power supply of the base 700 is holding a relatively small amount of electrical charge, relative to the storage capacity of the power supply.

The stored power icon 724 may change color and/or fill pattern based on the size of the stored power icon 724 in relation to the meter 722. For example, the stored power icon 724 may be green if and/or when the stored power icon 724 fills at least a high threshold proportion of the meter 722 (e.g., ≥50%). In another example, the stored power icon 724 may be yellow if and/or when the stored power icon 724 fills at least a low threshold proportion of the meter 722 but less than the high threshold proportion of the meter 722 (e.g., <50% and ≥25%). In another example, the stored power icon 724 may be red if and/or when the stored power icon 724 fills less than the lower threshold proportion of the meter 722 (e.g., <25%).

As further shown in FIG. 7B, the power graphical display may selectively display a charging icon 730 based on whether the power supply of the base 700 is presently being charged/re-charged with electrical power. In some example embodiments the stored power icon 724 may be altered based on whether the charging icon 730 is being displayed. For example, the stored power icon 724 may be an animation sequence wherein the icon is repeatedly changing size relative to the meter 722 and/or is changing color, based on the charging icon 730 being displayed.

In some example embodiments, the stored power icon 724 may indicate a quantity of instances of vapor generation that may be supported by the power supply of the base 700 with the amount of power stored therein. For example, the stored power icon 724 may be displayed as a set of segments, wherein each separate segment of the stored power icon 724 represents an individual instance of vapor generation that may be supported by the stored electrical power. With the occurrence of each successive instance of vapor generation supported by the power supply, one or more segments may be successively removed from icon 724, causing the stored power icon 724 to shrink in size relative to the meter 722. If and/or when the power supply does not store sufficient power to support an instance of vapor generation, the stored power icon 724 may include no such segments, a particular symbol (e.g., a red X symbol) indicating insufficient stored power, some combination thereof, or the like.

Figure 7C:
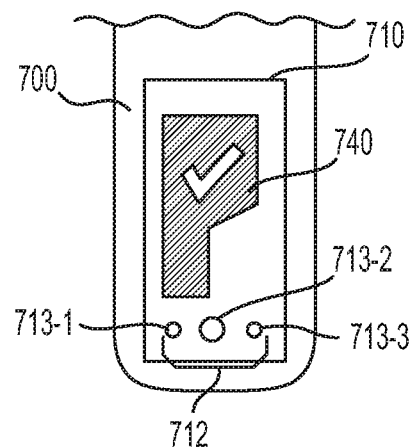

Referring now to FIG. 7C, the display interface 710 may be configured to display a vapor cartridge graphical display ("VCGD"), of a sequence of graphical displays, that indicates a state of a vapor cartridge coupled to the base 700. The vapor cartridge graphical display may indicate whether a vapor cartridge is coupled to the base 700, whether the vapor cartridge holds sufficient pre-vapor formulation (e.g., at least a threshold amount of pre-vapor formulation) to enable the vapor cartridge to support at least a threshold quantity of instances of vapor generation (e.g., generate at least one instance of vapor), some combination thereof, or the like.

As shown in FIG. 7C, the vapor cartridge graphical display may be a second graphical display of a three-display sequence. Thus, the vapor cartridge graphical display includes a display of the sequence indicator icon 712 wherein a second icon 713-2, of the sequence of three icons 713-1, 713-2, and 713-3 that represents the three separate graphical displays of the sequence, is changed relative to the other icons in order to convey that the presently-displayed graphical display is the second graphical display of the sequence. As shown, the second icon 713-2 is enlarged, relative to icons 713-1 and 713-3, when the vapor cartridge graphical display is displayed on interface 710, thereby conveying that the vapor cartridge graphical display is being displayed.

Still referring to FIG. 7C, the vapor cartridge graphical display may include a vapor cartridge icon 740 that indicates whether the base 700 is coupled to a vapor cartridge that is configured to support at least one instance of vapor generation. A vapor cartridge that is configured to support at least one instance of vapor generation may be a vapor cartridge that stores at least a threshold amount of pre-vapor formulation therein.

In FIG. 7C, the icon 740 indicates that the base 700 is coupled to a vapor cartridge that is configured to support at least one instance of vapor generation. The icon 740 shown in FIG. 7C does not indicate a particular quantity of instances of vapor generation that may be supported by the amount of pre-vapor formulation held in the coupled vapor cartridge. However, it will be understood that, in some example embodiments, the icon 740 may display an indication of the particular quantity of instances of vapor generation that may be supported by the amount of pre-vapor formulation held in the coupled vapor cartridge.

If and/or when the base 700 is not coupled to a vapor cartridge, icon 740 may present a graphical indication that the base 700 is not coupled to a vapor cartridge. If and/or when the base 700 is coupled to a vapor cartridge that is not configured to support at least a threshold quantity of instances of vapor generation, the icon 740 may present a graphical indication that the base 700 is coupled to a vapor cartridge that is not configured to support at least a threshold quantity of instances of vapor generation.

Figure 7D:
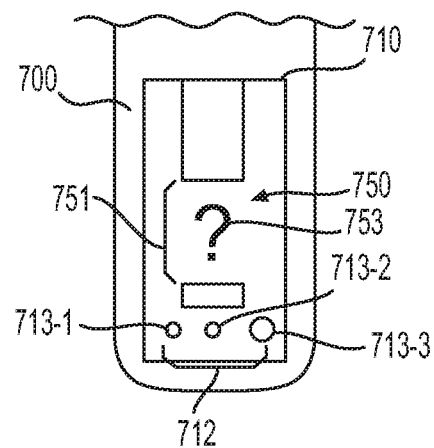

In some example embodiments, if and/or when the remaining count associated with the vapor cartridge is depleted (e.g., the expiration condition is reached), icon 740 may present an indication that vapor generation is disabled in association with the presently-coupled vapor cartridge. Upon the removal of the vapor cartridge and the coupling of a new vapor cartridge to the base 700, the vapor cartridge graphical display may revert to a graphical indication of a vapor cartridge configured to support at least one instance of vapor generation, for example as shown in FIG. 7D.

Referring now to FIGS. 7D-7H, the display interface 710 may be configured to display a flavor cartridge graphical display ("FCGD"), of a sequence of graphical displays, that indicates a state of a flavor cartridge inserted into a vapor cartridge that is coupled to the base 700. The flavor cartridge graphical display may indicate whether a flavor cartridge is inserted into the vapor cartridge that is coupled to the base 700 (such a vapor cartridge that is coupled to the base 700 being referred to herein as a "coupled vapor cartridge"), a quantity of instances of vapor generation that may be supported by the presently-inserted flavor cartridge, a quantity of remaining time during which one or more instances of vapor generation that may be supported by the presently-inserted flavor cartridge, some combination thereof, or the like.

As shown in FIGS. 7D-7H, the flavor cartridge graphical display may be a third graphical display of a three-display sequence. Thus, the flavor cartridge graphical display includes a display of the sequence indicator icon 712 wherein a third icon 713-3, of the sequence of three icons 713-1, 713-2, and 713-3 that represents the three separate graphical displays of the sequence, is changed relative to the other icons in order to convey that the presently-displayed graphical display is the third graphical display of the sequence. As shown, the third icon 713-3 is enlarged, relative to icons 713-1 and 713-2, when the flavor cartridge graphical display is displayed on interface 710, thereby conveying that the flavor cartridge graphical display is being displayed.

Referring generally to FIGS. 7D-7H, the flavor cartridge graphical display may include a graphical icon 750 that is a representation of a flavor cartridge. The icon 750 may thus visually resemble the appearance of a flavor cartridge. The icon 750 includes a remaining count meter 751 that may indicate a quantity of instances of vapor generation remaining until vapor generation is disabled with the presently-inserted flavor cartridge and/or a magnitude of time remaining until vapor generation is disabled with the presently-inserted flavor cartridge. The remaining count meter 751 may be referred to herein as a "remaining count meter," a "remaining count icon," some combination thereof, or the like.

As shown in FIG. 7D, the remaining count meter 751 may present a "missing flavor cartridge" icon 753 if and/or when the control circuitry in the base 700 determines that a flavor cartridge is not inserted into the coupled vapor cartridge and/or is unable to determine that a flavor cartridge is inserted into the coupled vapor cartridge. The remaining count meter 751 may also present the "missing flavor cartridge" icon 753 if a vapor cartridge is not presently coupled to the base 700.

Figure 7E:
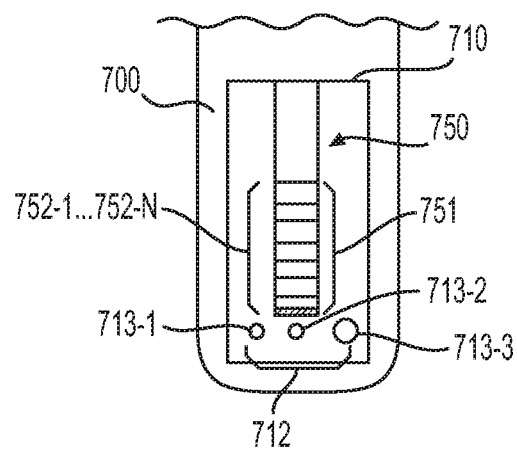

As shown in FIG. 7E, if and/or when a flavor cartridge is newly-inserted into the coupled vapor cartridge, and prior to any subsequent instance of vapor generation, the remaining count meter 751 may present a set of vapor generation sub-icons 752-1 to 752-N that collectively fill out the representation of the flavor cartridge in icon 750. Each sub-icon may be a representation of a separate portion of an initial remaining count associated with a presently-inserted flavor cartridge. As a result, the displayed sub-icons 752-1 to 752-N ("N" being an integer greater than 0) provide a graphical representation of the present magnitude of the remaining count associated with the presently-inserted flavor cartridge.

Figure 7F:
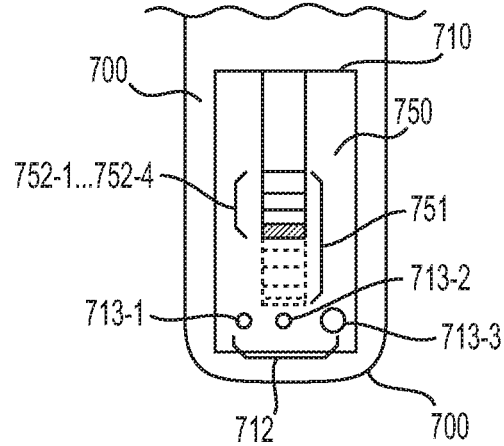
Figure 7G:
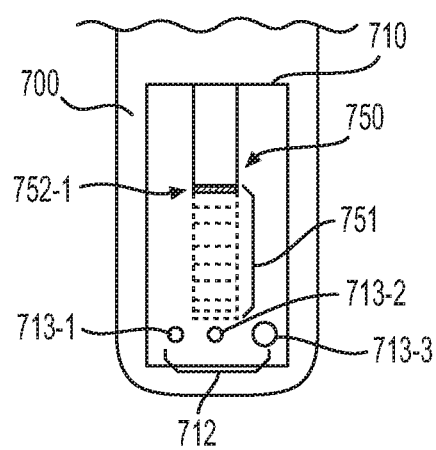

In an example, each sub icon 752-1 to 752-N may represent one or more remaining instances of vapor generation that may be supported by the base 700 while the presently-inserted flavor cartridge remains inserted in the coupled vapor cartridge until vapor generation by the coupled vapor cartridge is disabled by the control circuitry of the base 700. As shown in FIGS. 7F-7G, the quantity of sub-icons 752-1 to 752-N may decrease (e.g., may be decremented) with successive decrementing of the remaining count (e.g., successive instances of vapor generation, a countdown of remaining elapsed time, or the like), until the value of the remaining count is depleted below a threshold value. As shown in FIGS. 7E-7G, a leading sub-icon 752-N of the remaining sub-icons 752-1 to 752-N may be displayed to have a different appearance (e.g., different color and/or animation sequence).

In some example embodiments, each sub-icon 752-1 to 752-N may represent a remaining count that itself represents a combination of remaining time and remaining instances of vapor generation, while the presently-inserted flavor cartridge remains inserted in the coupled vapor cartridge, until vapor generation by the coupled vapor cartridge is disabled by the control circuitry of the base 700. The sub-icons 752-1 to 752-N may be decremented based on a combination of elapsed time and quantity of instances of vapor generation.

Figure 7H:
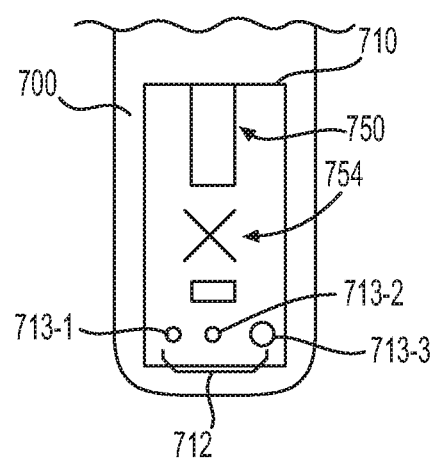

As shown in FIG. 7H, if and/or when the remaining count is depleted (e.g., the expiration condition is reached), the flavor cartridge graphical display may present an indication that vapor generation is disabled in association with the presently-inserted flavor cartridge. As shown in FIG. 7H, for example, icon 751 includes a flavor cartridge exhausted icon 754 that indicates that vapor generation has been disabled due to the expiration condition associated with the inserted flavor cartridge being reached. Upon the removal of the flavor cartridge and the insertion of a new flavor cartridge into the coupled vapor cartridge, the flavor cartridge graphical display may revert to a graphical indication of a full ("initial") remaining count, for example as shown in FIG. 7E.

Operations

Figure 8:
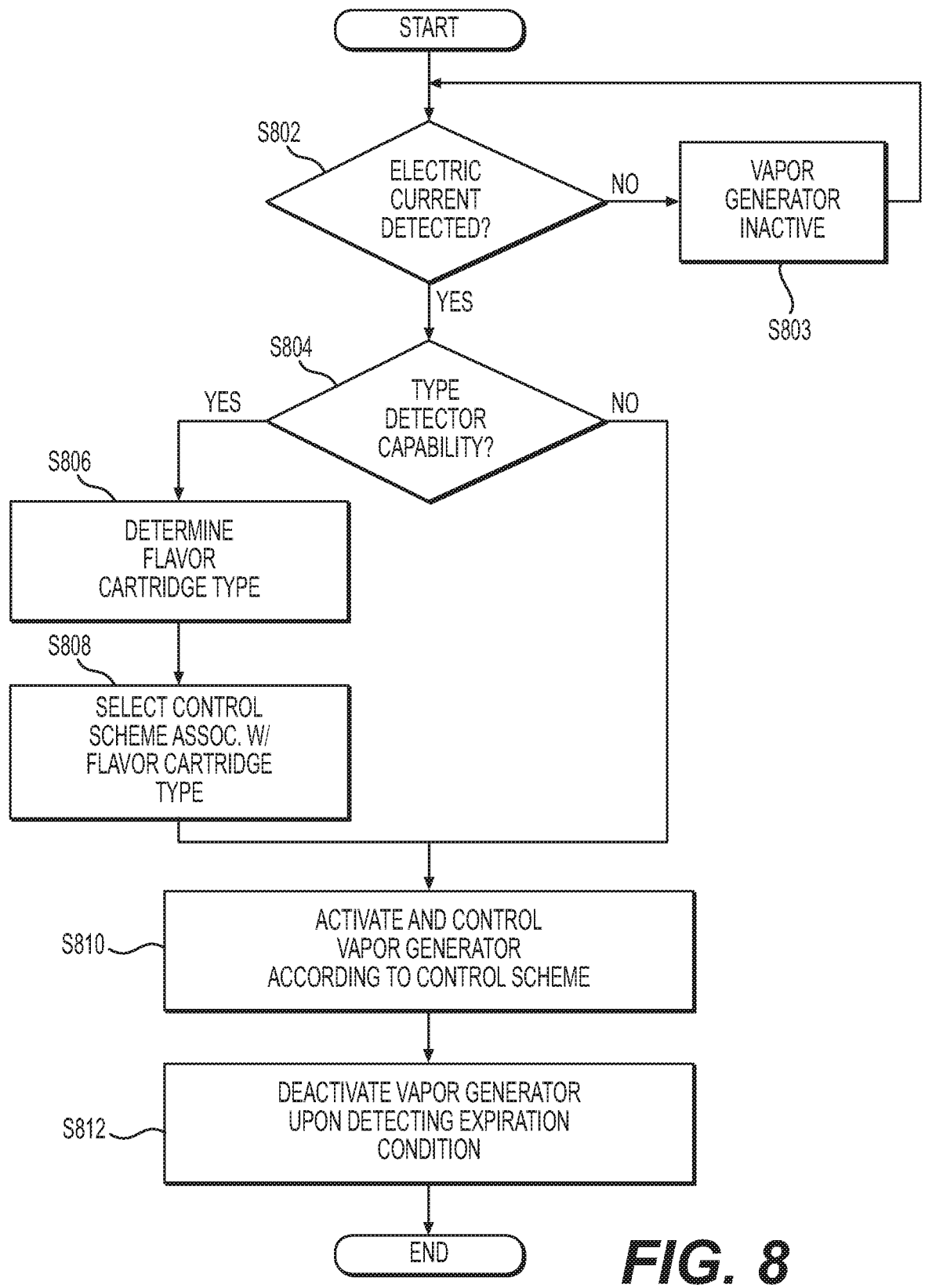
FIG. 8 is a flowchart illustrating controlling vapor generation by a non-combustible vaping device, according to some example embodiments.

FIG. 8 is a flowchart illustrating controlling vapor generation by a non-combustible vaping device, according to some example embodiments.

One or more of the operations illustrated in FIG. 8 may be implemented by control circuitry included in one or more portions of the non-combustible vaping device, including at least one of the control circuitry 114 and the computing device 160 illustrated in FIG. 1B. As indicated above, the control circuitry 114 and/or the computing device 160 may include a memory (e.g., a non-transitory computer-readable storage medium, "memory device," or the like) storing a program of instructions and a processor ("processing circuitry") configured to execute the stored program of instructions to implement one or more operations. In some example embodiments, the control circuitry 114 is configured to implement the functionality of the computing device 160 as described above.

At S802, a determination is made regarding whether an electrical current is detected in an electric circuit that includes the authentication assembly. Because the at least two electrically conductive instruments of the authentication assembly are spaced apart ("isolated from direct contact") by a gap space, a presence of an electrical current through an electric circuit that includes the authentication assembly indicates that the at least two electrically conductive instruments are electrically coupled ("electrically connected") together through a conductive material in the gap space, such that the gap space is electrically bridged by the conductive material. Such a conductive material in the gap space may be determined to be an instance of electrically conductive material included in a flavor cartridge inserted into the channel space at least partially defined by the channel structure.

Accordingly, based on detecting an electrical current in the electric circuit that includes the authentication assembly, a determination may be made that an authenticated flavor cartridge (e.g., "appropriate" flavor cartridge) has been inserted into the channel space of the non-combustible vaping device.

In some example embodiments, if and/or when the control circuitry implementing operation S802 is included in a non-combustible vaping device that includes an authentication assembly that includes a displaceable instrument configured to be displaced by a flavor cartridge inserted into a vapor cartridge of the non-combustible vaping device, the electric current may be detected based on the displaceable instrument being displaced by the flavor cartridge to close an electrical circuit, the closed electrical circuit being detectable by the control circuitry based on an electrical current being induced in the closed electrical circuit.

As shown at S803, in response to a determination that an electrical current is not present in the electric circuit, a determination may be made that an authenticated flavor cartridge has not been inserted into the channel space, and the vapor generator may be deactivated and/or maintained in a deactivated state, such that the non-combustible vaping device is inhibited from generating a vapor.

As referred to herein, a detection of an electrical current in the electric circuit that includes the authentication assembly may include detecting an electrical current having a magnitude that at least meets a particular threshold electrical current. As a result, the probability of false determinations at may be reduced.

At S804 and S806, in response to a determination that the electrical current is detected at S802, and based on the control circuitry, alone or in combination with computing device, being configured to determine a "type" associated with the authenticated flavor cartridge, the "type" associated with the authenticated flavor cartridge may be determined. Such a determination may include processing the electrical current detected at S802 and determining one or more properties associated with the detected electrical current. Such one or more properties may include determining an initial remaining count (e.g., quantity of instances of vapor generation and/or duration of time) associated with the flavor cartridge.

In some example embodiments, a determination of a particular flavor cartridge type may be made based on a determination that a magnitude of the detected electrical current is within a particular range of electrical current values that is associated with a particular flavor cartridge type. In some example embodiments, a set of ranges of electrical current values and corresponding flavor cartridge types may be stored in a database, including a look-up table. Such a database may be stored in a memory. Such a memory may be included in the control circuitry and/or in a computing device.

For example, based on processing a detected electrical current to determine a value of the magnitude of the detected electrical current, the database may be accessed to determine which range of values, if any, includes the value of the detected electrical current. Based on identifying a particular range that includes a value of the detected electrical current, the database may be accessed to identify a particular flavor cartridge type that is associated with the identified particular range.

As referred to herein, a flavor cartridge type may include an indication of one or more particular properties associated with a flavor cartridge, including a particular flavor associated with the flavor cartridge, an amount of flavor material included in the flavor cartridge, a size and/or shape of flavor material in the flavor cartridge, a presence and/or configuration of multiple flavor materials in the flavor cartridge, a filter presence and/or size in the flavor cartridge, an indication of whether the flavor cartridge includes a flavor matrix and/or an outlet-end insert, some combination thereof, or the like.

At S808, based upon determining a particular type associated with the authenticated flavor cartridge, a particular vapor generator control scheme associated with the particular flavor cartridge type is identified and selected.

A control scheme associated with a particular flavor cartridge type may be included in the above-noted database in which the particular flavor cartridge type is associated with a particular value or range of values of one or more properties of a detected electrical current. Thus, based on identifying a particular flavor cartridge type at 806, a particular control scheme associated with the particular flavor cartridge type may be identified by accessing the database.

As referred to herein, a control scheme may include a set and/or sequence of control signals and/or control logic that may be used to control the supply of electrical power to a vapor generator of the non-combustible vaping device to cause one or more instances of vapor to be generated. The control scheme may include an initial remaining count associated with the authenticated flavor cartridge. The control scheme may include a remaining count associated with the coupled vapor cartridge. The remaining count associated with the coupled vapor cartridge may be an initial remaining count associated with the coupled vapor cartridge.

The control scheme may specify one or more various parameters associated with a set of vapor generation operations to be performed by the vapor generator based on electrical power supplied according to control circuitry control. Such parameters may include a magnitude of vapor to be generated by the vapor generator in response to each vaping command, a magnitude of a duration of elapsed time during which the vapor generator is to generate vapor, some combination thereof, or the like. The period of elapsed time may extend from the time at which the electrical current is detected at S802 and/or the time at which the vapor generator is first controlled to generate vapor after the electrical current is detected at S802.

A control scheme may include an expiration condition, associated with an initial remaining count of the control scheme, that indicates one or more parameters according to which the vapor generator is to be subsequently deactivated after being activated and controlled to generate vapor according to the control scheme. An expiration condition may include a threshold value of the remaining count associated with the flavor cartridge, a threshold value of the remaining count associated with the vapor cartridge, some combination thereof, or the like. A threshold value of the remaining count associated with the flavor cartridge may include a threshold magnitude of remaining duration of time during which the vapor generator may be activated, a threshold remaining cumulative duration of vapor generations implemented by the vapor cartridge, a threshold remaining quantity of instances of vapor to be generated by the vapor generator, some combination thereof, or the like. A threshold value of the remaining count associated with the vapor cartridge may include a threshold quantity of successive insertions of flavor cartridges into the vapor cartridge, a threshold remaining cumulative duration of vapor generations implemented by the vapor cartridge, some combination thereof, or the like.

A vaping command may include a command signal received at the control circuitry based on adult vaper interaction with an interface of the non-combustible vaping device, based on sensor data received from one or more sensors in the non-combustible vaping device, some combination thereof, or the like.

If, at S804, the control circuitry is not configured to determine a particular flavor cartridge type associated with the authenticated flavor cartridge, the vapor generator may be controlled according to a base (e.g., "default") control scheme that is selected based on the detection of the electrical current at S802.

At S810, the vapor generator is activated and controlled according to the selected control scheme. As indicated above, such control may include controlling the supply of electrical power to the vapor generator, to cause the vapor generator to generate a particular amount of generated vapor over a particular magnitude of a duration, based on a determination that vapor is to be generated. Such a determination may be made based on a determination that a vaping command is received from an interface of the non-combustible vaping device based on adult vaper interaction therewith, a determination that sensor data received from a sensor of the non-combustible vaping device includes data values (e.g., airflow magnitude, pressure change magnitude, or the like) that at least meet one or more threshold data values, some combination thereof or the like.

Controlling a vapor generator according to a selected control scheme may include maintaining the vapor generator in an "active state," wherein the vapor generator may be controlled to generate vapor, until one or more expiration conditions associated with the selected control scheme are determined to be reached.

At S812, based on a determination that an expiration condition associated with the selected control scheme is reached (e.g., the remaining count associated with the flavor cartridge and/or the remaining count associated with the vapor cartridge is less than a corresponding threshold value), the vapor generator may be deactivated (e.g., vapor generation by the vapor generator in the vapor cartridge may be selectively disabled).

Figure 9:
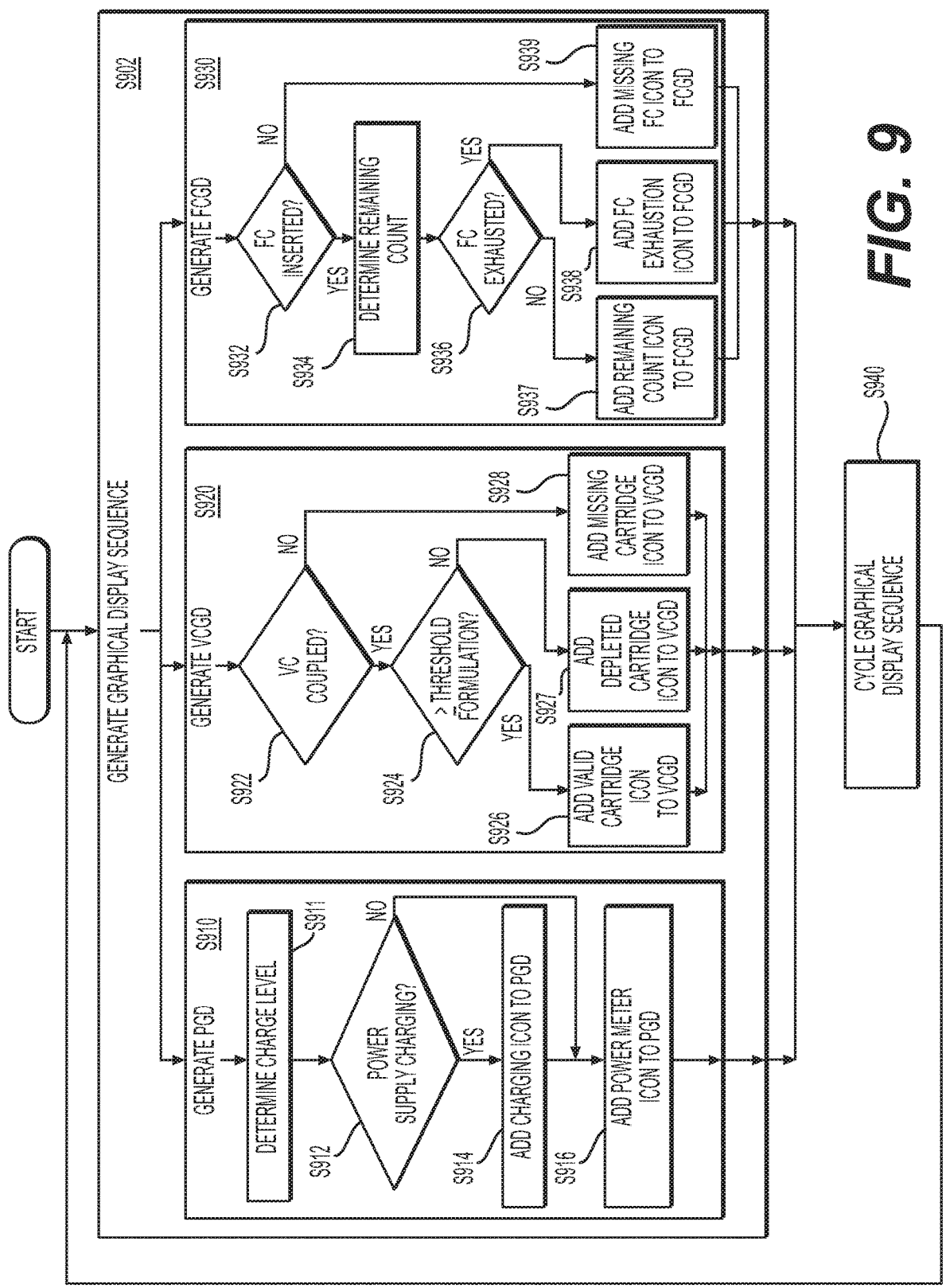
FIG. 9 is a flowchart illustrating generating and displaying a sequence of graphical displays by a non-combustible vaping device, according to some example embodiments.

FIG. 9 is a flowchart illustrating generating and displaying a sequence of graphical displays by a non-combustible vaping device, according to some example embodiments.

One or more of the operations illustrated in FIG. 9 may be implemented by control circuitry included in one or more portions of the non-combustible vaping device, including at least one of the control circuitry 114 and the computing device 160 illustrated in FIG. 1B. As indicated above, the control circuitry 114 and the computing device 160 may include a memory (e.g., a non-transitory computer-readable storage medium, "memory device," or the like) storing a program of instructions and a processor ("processing circuitry") configured to execute the stored program of instructions to implement one or more operations. In some example embodiments, the control circuitry 114 is configured to implement the functionality of the computing device 160 as described above.

At S902, a graphical display sequence corresponding to a non-combustible vaping device is generated. The graphical display sequence may include a sequence of graphical displays associated with different aspects of the non-combustible vaping device. As shown in FIG. 9, for example, the graphical display sequence may include a power graphical display ("PGD"), a vapor cartridge graphical display ("VCGD"), and a flavor cartridge graphical display ("FCGD"). Accordingly, as shown in FIG. 9, generating a graphical display sequence at S902 may include generating the PGD at S910, generating the VCGD at S920, and generating the FCGD at S930. The operations performed at S910, S920, and S930 may be performed in series in relation to each other, in parallel in relation to each other, some combination thereof, or the like.

At S911, generating the PGD may include determining an absolute amount and/or proportional amount of electrical power stored in a power supply of the base of the non-combustible vaping device. The amount of stored electrical power may be determined based on monitoring one or more aspects of the power supply, including an output voltage thereof, communicating with the power supply to receive electrical power storage information, or the like.

At S912, generating the PGD may include determining whether the power supply of the base of the non-combustible vaping device is presently being charged/re-charged. If so, as shown at S914, the PGD is caused to include at least a charging icon.

At S916, the PGD is caused to include a stored power meter and a stored power icon that indicates an amount of electrical power stored at the power supply of the base as a proportion of the electrical power storage capacity of the power supply.

In some example embodiments, the power supply icon may indicate the amount of stored electrical power as a set of increments or "segments" that each represent a separate, individual instance of vapor generation that may be supported by the stored electrical power, thereby providing an indication of the quantity of instances of vapor generation that may be supported by the stored electrical power.

At S922, generating the VCGD may include determining whether a vapor cartridge is presently coupled to the base of the non-combustible vaping device. Such a determination may include determining whether power and/or information is being communicated between the base and the vapor cartridge via one or more interfaces and/or electrical connectors thereof. If not, at S928, the VCGD is caused to include an icon indicating that the vapor cartridge is not coupled to the base.

At S924, generating the VCGD may include determining whether a coupled vapor cartridge is holding at least a threshold amount of pre-vapor formulation. Such a determination may be made based on communication between the base and the vapor cartridge. Such a determination may include determining whether an expiration condition associated with a remaining count of a presently-coupled vapor cartridge is reached. If not (e.g., if the expiration condition is determined to be reached), as shown at S927, the VCGD is caused to include an icon indicating that the vapor cartridge, though coupled to the base, has insufficient pre-vapor formulation to support vapor generation and/or an icon indicating that the vapor cartridge is depleted.

If so (e.g., if the expiration condition is determined to be not reached), as shown at S926, the VCGD is caused to include an icon indicating that a vapor cartridge that has sufficient vapor formulation to support vapor generation is coupled to the base. The icon may further indicate a quantity of instances of vapor generation that may be supported by the vapor cartridge, an amount of pre-vapor formulation held in the vapor cartridge, some combination thereof, or the like.

At S932, generating the FCGD may include determining whether a flavor cartridge is inserted into a coupled vapor cartridge. Such a determination may be made based on a determination whether an electrical signal is received at the base via an electrical circuit that includes an authentication assembly in the vapor cartridge. If not, as shown at S939, the FCGD is caused to include an icon indicating that no flavor cartridge is inserted in the vapor cartridge.

At S934, generating the FCGD may include determining a "remaining count" of the period of remaining elapsed time and/or quantity of remaining instances of vapor generation associated with a presently-inserted flavor cartridge. At S936, generating the FCGD may include determining whether an expiration condition associated with the presently-inserted flavor cartridge is reached (e.g., the determined "remaining count" is below a threshold value). As described above, a particular period of time and/or quantity of instances of vapor generation ("remaining count") may be associated with ("allocated to") a flavor cartridge upon the flavor cartridge being detected as being inserted into the vapor cartridge. The remaining count may be decremented with the elapse of time following the initial detection of the flavor cartridge, the elapse of time following an initial instance of vapor generation following the initial detection of the flavor cartridge, the occurrence of one or more instances of vapor generation following the initial detection of the flavor cartridge, some combination thereof, or the like.

If, at S936, the expiration condition is determined to be reached (e.g., the value of a present remaining count is decremented, from the value of the initial remaining count, below a threshold value), the FCGD is caused to include, at S938, an icon indicating that the flavor cartridge is exhausted and vapor generation is disabled.

If, at S934, the expiration condition associated with the presently-inserted flavor cartridge is determined to not be reached, the FCGD is caused to include, at S937, an icon indicating the remaining count. Such an icon may be the remaining count meter 751 that includes one or more sub-icons 752-1 to 752-N indicating a magnitude of the remaining count.

At S940, the generated graphical displays (e.g., the PGD, the VCGD, and the FCGD) may be displayed on a display interface according to a display sequence, wherein, the separate graphical displays may be separately and sequentially displayed in response to successive, sequential interactions by an adult vaper with an interface (e.g., tactile interface) of the non-combustible vaping device, and thus based on successive command signals received from the interface. In some example embodiments, the sequence of graphical displays may be displayed in a sequence wherein the separate graphical displayed are sequentially displayed on a display interface according to an automatic (e.g., without adult vaper intervention) display sequence wherein the displayed graphical display is switched to a separate graphical display in the sequence upon the elapse of a particular amount of elapsed time.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

We claim:

1. A vapor cartridge for a non-combustible vaping device, the vapor cartridge comprising:
   a channel structure having opposite, first and second ends, the channel structure at least partially defining a channel space extending at least between the first and second ends, the channel structure configured to receive a flavor cartridge into the channel space via the first end of the channel structure;
   a vapor generator at the second end of the channel structure, the vapor generator configured to heat a pre-vapor formulation to form a generated vapor and provide the generated vapor to the second end of the channel structure, the channel structure further configured to receive the flavor cartridge, such that the flavor cartridge is positioned in the channel structure to receive the generated vapor from the vapor generator; and
   a set of electrically conductive instruments extending into the channel space and isolated from direct contact with each other across a gap space in the channel space, the electrically conductive instruments configured to independently and directly contact an instance of electrically conductive material of the flavor cartridge based on the flavor cartridge being received into the channel space, such that the electrically conductive instruments are electrically connected to each other through the instance of electrically conductive material of the flavor cartridge that is received into the channel space.

2. The vapor cartridge of claim 1, wherein,
   at least one electrically conductive instrument of the set of electrically conductive instruments is configured to directly contact the instance of electrically conductive material based on at least partially impinging into an interior of the flavor cartridge.

3. The vapor cartridge of claim 2, wherein,
   the at least one electrically conductive instrument includes an electrically conductive blade, the electrically conductive blade configured to cut into at least a portion of the flavor cartridge to directly contact the instance of electrically conductive material of the flavor cartridge.

4. The vapor cartridge of claim 3, wherein,
the set of electrically conductive instruments includes a set of electrically conductive blades, the electrically conductive blades configured to cut into separate portions of the flavor cartridge to directly contact the instance of electrically conductive material of the flavor cartridge, such that the electrically conductive blades are electrically connected to each other through the instance of electrically conductive material of the flavor cartridge, the set of electrically conductive blades including the electrically conductive blade.

5. The vapor cartridge of claim 1, wherein,
at least one electrically conductive instrument of the set of electrically conductive instruments is an electrically conductive plate configured to establish contact with the instance of electrically conductive material.

6. The vapor cartridge of claim 1, wherein,
at least one electrically conductive instrument of the set of electrically conductive instruments is a projection instrument configured to puncture at least a portion of the flavor cartridge to directly contact the instance of electrically conductive material of the flavor cartridge.

7. The vapor cartridge of claim 1, further comprising:
a reservoir refill port in fluid communication with a pre-vapor formulation reservoir of the vapor generator, the reservoir refill port configured to enable the pre-vapor formulation reservoir to be filled with the pre-vapor formulation.

8. A non-combustible vaping device, comprising:
a vapor cartridge including,
   a channel structure having opposite, first and second ends, the channel structure at least partially defining a channel space extending at least between the first and second ends, the channel structure configured to receive a flavor cartridge via the first end of the channel structure,
   a vapor generator at the second end of the channel structure, the vapor generator configured to heat a pre-vapor formulation to form a generated vapor and provide the generated vapor to the second end of the channel structure, the channel structure further configured to receive the flavor cartridge, such that the flavor cartridge is positioned in the channel structure to receive the generated vapor from the vapor generator, and
   a set of electrically conductive instruments extending into the channel space snf isolated from direct contact with each other across a gap space in the channel space; and
a base including a power supply that is electrically coupled to the electrically conductive instruments,
wherein the electrically conductive instruments are configured to independently and directly contact an instance of electrically conductive material of the flavor cartridge based on the flavor cartridge being received into the channel space, such that the electrically conductive instruments establish an electrical circuit that is closed and extends at least between the electrically conductive instruments through the instance of electrically conductive material of the flavor cartridge that is received into the channel space.

9. The non-combustible vaping device of claim 8, wherein,
the base includes control circuitry configured to
   detect that the electrical circuit is closed,
   determine that the flavor cartridge is in a position that is proximate to the vapor generator, based on the detecting, and
   control the forming of the generated vapor by the vapor generator, based on the determining.

10. The non-combustible vaping device of claim 9, wherein,
the control circuitry is configured to
   monitor one or more properties of a current in the electrical circuit,
   determine that the flavor cartridge is associated with a particular flavor cartridge type, of a plurality of flavor cartridge types, based on the monitoring, and
   selectively control the forming of the generated vapor according to the particular flavor cartridge type.

11. The non-combustible vaping device of claim 8, wherein,
at least one electrically conductive instrument of the set of electrically conductive instruments is configured to directly contact the instance of electrically conductive material based on at least partially impinging into an interior of the flavor cartridge.

12. The non-combustible vaping device of claim 11, wherein,
the at least one electrically conductive instrument includes an electrically conductive blade, the electrically conductive blade configured to cut into at least a portion of the flavor cartridge to directly contact the instance of electrically conductive material of the flavor cartridge.

13. The non-combustible vaping device of claim 12, wherein,
the set of electrically conductive instruments includes a set of electrically conductive blades, the electrically conductive blades configured to cut into separate portions of the flavor cartridge to directly contact the instance of electrically conductive material of the flavor cartridge, such that the electrically conductive blades are electrically connected to each other through the instance of electrically conductive material of the flavor cartridge, the set of electrically conductive blades including the electrically conductive blade.

14. The non-combustible vaping device of claim 8, wherein,
at least one electrically conductive instrument of the set of electrically conductive instruments is a plate instrument configured to flush contact the instance of electrically conductive material.

15. The non-combustible vaping device of claim 8, wherein,
at least one electrically conductive instrument of the set of electrically conductive instruments is a projection instrument configured to puncture at least a portion of the flavor cartridge to directly contact the instance of electrically conductive material of the flavor cartridge.

16. The non-combustible vaping device of claim 8, wherein the vapor cartridge and the base are configured to be detachably coupled together.

17. The non-combustible vaping device of claim 16, wherein the base includes a plurality of sets of pogo pin connectors, each set of pogo pin connectors configured to couple with a corresponding set of electrical connectors of the vapor cartridge to
   supply electrical power from the power supply to the vapor cartridge, communicate data between the base and the vapor cartridge, or enable control circuitry of the base to detect the closed electrical circuit to determine that the flavor cartridge is inserted into the vapor cartridge.

18. The non-combustible vaping device of claim 8, wherein the power supply includes a rechargeable battery.

19. A vapor cartridge for a non-combustible vaping device, the vapor cartridge comprising:

a channel structure having opposite, first and second ends, the channel structure including an inner surface at least partially defining a channel space extending at least between the first and second ends, the channel structure configured to receive a flavor cartridge into the channel space via the first end of the channel structure, the channel structure further including a portal extending through a side portion of the channel structure and defining an opening in the inner surface of the channel structure;

a vapor generator at the second end of the channel structure, the vapor generator configured to heat a pre-vapor formulation to form a generated vapor and provide the generated vapor to the second end of the channel structure, the channel structure further configured to direct the flavor cartridge through the channel space towards the second end of the channel structure, such that the flavor cartridge is positioned to receive the generated vapor from the vapor generator; and a set of electrically conductive instruments extending into the channel space, the electrically conductive instruments including a displaceable instrument configured to extend at least partially through the portal of the channel structure into the channel space to constrict a diameter of a portion of the channel space to be less than an inner diameter of the channel space defined by the inner surface of the channel structure, the electrically conductive instruments configured to selectively directly contact each other, such that the electrically conductive instruments are electrically connected to each other, based on the displaceable instrument being displaced by the flavor cartridge at least partially through the portal of the channel structure to widen the constricted diameter of the portion of the channel space to a widened diameter that corresponds with an outer diameter of the flavor cartridge.

20. The vapor cartridge of claim 19, wherein, the displaceable instrument includes a fixed portion and a displaceable portion, the fixed portion fixed to a portion of the vapor cartridge, the displaceable portion configured to extend through the portal of the channel structure.

21. The vapor cartridge of claim 19, wherein, the set of electrically conductive instruments are configured to selectively establish a closed electrical circuit that includes the vapor generator, based on the displaceable instrument being displaced by the flavor cartridge at least partially through the portal of the channel structure, such that the set of electrically conductive instruments are configured to selectively enable vapor generation by the vapor generator according to whether the flavor cartridge is inserted into the vapor cartridge.

* * * * *